(12) United States Patent
Pope et al.

(10) Patent No.: US 6,800,095 B1
(45) Date of Patent: Oct. 5, 2004

(54) DIAMOND-SURFACED FEMORAL HEAD FOR USE IN A PROSTHETIC JOINT

(75) Inventors: Bill J. Pope, Springville, UT (US); Jeffery K. Taylor, Loomis, CA (US); Richard H. Dixon, Provo, UT (US); Clayton F. Gardinier, American Fork, UT (US); Louis M. Pope, Provo, UT (US); Dean C. Blackburn, Springville, UT (US); Michael A. Vail, Genola, UT (US); Kenneth M. Jensen, Springville, UT (US)

(73) Assignee: Diamicron, Inc., Orem, UT (US)

( * ) Notice: Subject to any disclaimer, the term of this patent is extended or adjusted under 35 U.S.C. 154(b) by 0 days.

(21) Appl. No.: 09/494,240

(22) Filed: Jan. 30, 2000

Related U.S. Application Data

(63) Continuation-in-part of application No. 09/457,226, filed on Dec. 8, 1999, now abandoned, which is a continuation of application No. 08/844,395, filed on Apr. 18, 1997, now Pat. No. 6,010,533, which is a continuation of application No. 08/631,877, filed on Apr. 16, 1996, now Pat. No. 5,645,601, which is a continuation of application No. 08/289,696, filed on Aug. 12, 1994, now abandoned.

(51) Int. Cl.[7] .................................................. A61F 2/30
(52) U.S. Cl. ..................... 623/23.11; 428/212; 428/336; 428/325; 428/408; 428/472; 623/22.4; 623/23.12; 623/23.36; 623/23.4; 623/23.42; 623/23.52; 623/23.53; 623/23.6
(58) Field of Search .......................... 623/22.4, 23.12, 623/23.11, 23.36, 23.4, 23.42, 23.52, 23.53, 23.6, 18, 11, 23.15, 23.56; 428/408, 325, 472, 336, 212; 427/2.26, 180, 189

(56) References Cited

U.S. PATENT DOCUMENTS

| | | | |
|---|---|---|---|
| 2,947,608 A | 8/1960 | Hall | 23/209.1 |
| 2,947,609 A | 8/1960 | Strong | 23/209.1 |
| 2,947,610 A | 8/1960 | Hall et al. | 23/209.1 |
| 2,947,611 A | 8/1960 | Bundy | 23/209.1 |
| 2,992,900 A | 7/1961 | Bovenkerk | 23/209.1 |
| 3,031,269 A | 4/1962 | Bovenkerk | 23/209.1 |
| 3,097,929 A | 7/1963 | Ragan | 25/156 |
| 3,102,536 A | 9/1963 | Rose et al. | 128/92 |
| 3,150,413 A | 9/1964 | Zeitlin et al. | 18/16.5 |
| 3,201,828 A | 8/1965 | Fryklung | 18/16.5 |
| 3,292,997 A | 12/1966 | Strong | 23/209.2 |
| 3,297,407 A | 1/1967 | Wentorf, Jr. | 23/209.1 |
| 3,407,445 A | 10/1968 | Strong | 18/34 |
| 3,423,177 A | 1/1969 | Bovenkerk | 23/209.1 |
| 3,488,153 A | 1/1970 | Bundy | 23/209.1 |
| 3,574,580 A | 4/1971 | Stromberg et al. | 51/307 |
| 3,584,318 A | 6/1971 | Scales et al. | 3/1 |

(List continued on next page.)

FOREIGN PATENT DOCUMENTS

| | | | |
|---|---|---|---|
| GB | 2 283 772 | 5/1995 | E21B/10/46 |
| GB | 2 290 326 | 12/1995 | E21B/10/46 |
| GB | 2 290 327 | 12/1995 | E21B/10/46 |
| GB | 2 290 328 | 12/1995 | E21B/10/46 |

OTHER PUBLICATIONS

"Glass Coating for Artificial Joints Allows Bone Bonding" article from Internet (3 pages).
"Protecting Artificial Joints" article from Internet (3 pages).
Baker, N., "Fixation and Prosthetic Joints" article from http://www.ncsu.edu website (1998).

Primary Examiner—Archene Turner
(74) Attorney, Agent, or Firm—Daniel P. McCarthy; Parsons Behle & Latimer

(57) ABSTRACT

Prosthetic joints, components for prosthetic joints, superhard bearing and articulation surfaces, diamond bearing and articulation surfaces, substrate surface topographical features, materials for making joints, bearing and articulation surfaces, and methods for manufacturing and finishing the same, and related information are disclosed, including a diamond-surfaced femoral head for use in a prosthetic joint.

43 Claims, 44 Drawing Sheets

Fig. 2A

U.S. PATENT DOCUMENTS

| | | | |
|---|---|---|---|
| 3,597,158 A | 8/1971 | Horton | 23/209.1 |
| 3,658,056 A | 4/1972 | Huggler et al. | 128/92 |
| 3,683,421 A | 8/1972 | Martinie | 3/1 |
| 3,702,573 A | 11/1972 | Nemeth | 76/101 |
| 3,723,995 A | 4/1973 | Baumann | 3/1 |
| 3,778,586 A | 12/1973 | Breton et al. | 219/76 |
| 3,816,085 A | 6/1974 | Hall | 51/307 |
| 3,819,814 A | 6/1974 | Pope | 423/446 |
| 3,852,045 A | 12/1974 | Wheeler et al. | 29/182 |
| 3,864,758 A | 2/1975 | Yakich | 3/1 |
| 3,871,031 A | 3/1975 | Boutin | 3/1 |
| 3,894,297 A | 7/1975 | Mittelmeier | 3/1 |
| 3,977,026 A | 8/1976 | Battault | 3/1.91 |
| 4,005,495 A | 2/1977 | Locke et al. | 3/1.91 |
| 4,031,570 A | 6/1977 | Frey | 3/1 |
| 4,055,862 A | 11/1977 | Farling | 3/1.91 |
| 4,058,856 A | 11/1977 | Doerre et al. | 3/1.91 |
| 4,089,933 A | 5/1978 | Vereschagin et al. | 423/446 |
| 4,104,344 A | 8/1978 | Pope et al. | 264/42 |
| 4,104,441 A | 8/1978 | Fedoseev et al. | 428/408 |
| 4,115,875 A | 9/1978 | Rambert et al. | 3/1.913 |
| 4,126,924 A | 11/1978 | Akins et al. | 29/423 |
| 4,163,769 A | 8/1979 | Pope et al. | 264/42 |
| 4,164,794 A | 8/1979 | Spector et al. | 3/1.912 |
| 4,166,292 A | 9/1979 | Bokros | 3/1.91 |
| 4,196,181 A | 4/1980 | Vereschagin et al. | 423/446 |
| 4,206,517 A | 6/1980 | Pappas et al. | 3/1.91 |
| 4,214,322 A | 7/1980 | Kraus | 3/1.91 |
| 4,231,762 A | 11/1980 | Hara et al. | 51/309 |
| 4,259,072 A | 3/1981 | Hirabayashi et al. | 433/173 |
| 4,260,397 A | 4/1981 | Bovenkerk | 51/307 |
| 4,289,123 A | 9/1981 | Dunn | 128/84 R |
| 4,311,490 A | 1/1982 | Bovenkerk et al. | 51/307 |
| D265,204 S | 6/1982 | Turchan et al. | D15/130 |
| 4,332,037 A | 6/1982 | Esformes et al. | 3/1.91 |
| 4,349,922 A | 9/1982 | Agee | 3/1.91 |
| 4,380,471 A | 4/1983 | Lee et al. | 419/11 |
| 4,454,612 A | 6/1984 | McDaniel et al. | 3/1.913 |
| 4,470,158 A | 9/1984 | Pappas et al. | 3/1.911 |
| 4,518,659 A | 5/1985 | Gigl et al. | 428/539.5 |
| 4,525,179 A | 6/1985 | Gigl | 51/309 |
| 4,534,934 A | 8/1985 | Cho | 419/6 |
| 4,535,486 A | 8/1985 | Roberts et al. | 623/22 |
| 4,547,910 A | 10/1985 | Roberts et al. | 623/18 |
| 4,592,433 A | 6/1986 | Dennis | 175/329 |
| 4,604,106 A | 8/1986 | Hall et al. | 51/293 |
| 4,610,699 A | 9/1986 | Yazu et al. | 51/309 |
| 4,618,269 A | 10/1986 | Badrak et al. | 384/95 |
| 4,651,374 A | 3/1987 | Turchan | 10/130 |
| 4,662,348 A | 5/1987 | Hall et al. | 125/30 R |
| 4,687,487 A | 8/1987 | Hintermann | 623/18 |
| 4,693,722 A | 9/1987 | Wall | 623/18 |
| 4,694,918 A | 9/1987 | Hall | 175/329 |
| 4,708,496 A | 11/1987 | McPherson | 384/303 |
| 4,714,473 A | 12/1987 | Bloebaum | 623/20 |
| 4,729,440 A * | 3/1988 | Hall | |
| 4,731,088 A | 3/1988 | Collier | 623/22 |
| 4,738,322 A | 4/1988 | Hall et al. | 175/329 |
| 4,756,631 A | 7/1988 | Jones | 384/95 |
| 4,759,350 A | 7/1988 | Dunn et al. | 128/92 |
| 4,761,844 A | 8/1988 | Turchan | 10/140 |
| 4,766,040 A | 8/1988 | Hillert et al. | 428/552 |
| 4,778,486 A | 10/1988 | Csillag et al. | 51/309 |
| 4,784,023 A | 11/1988 | Dennis | 76/108 A |
| 4,784,662 A | 11/1988 | Muller | 623/22 |
| 4,789,251 A | 12/1988 | McPherson et al. | 384/317 |
| 4,797,241 A | 1/1989 | Peterson et al. | 264/63 |
| 4,797,326 A | 1/1989 | Csillag | 428/552 |
| 4,808,185 A | 2/1989 | Penenberg et al. | 623/20 |
| 4,813,959 A | 3/1989 | Cremascoli | 623/22 |
| 4,822,355 A | 4/1989 | Bhuvaneshwar | 623/2 |
| 4,822,368 A | 4/1989 | Collier | 623/22 |
| 4,824,442 A | 4/1989 | Cerceau | 51/293 |
| 4,840,631 A | 6/1989 | Mathys | 623/22 |
| 4,842,605 A | 6/1989 | Sonnerat et al. | 623/22 |
| 4,846,839 A | 7/1989 | Noiles | 623/18 |
| 4,861,350 A | 8/1989 | Phaal et al. | 51/307 |
| 4,865,603 A | 9/1989 | Noiles | 623/18 |
| 4,865,606 A | 9/1989 | Rehder | 623/20 |
| 4,866,885 A | 9/1989 | Dodsworth | 51/293 |
| 4,878,917 A | 11/1989 | Kranz et al. | 623/18 |
| 4,892,547 A | 1/1990 | Brown | 623/20 |
| 4,922,898 A | 5/1990 | Dunn | 606/85 |
| 4,925,701 A | 5/1990 | Jansen et al. | 427/38 |
| 4,931,068 A | 6/1990 | Dismukes et al. | 51/293 |
| 4,934,040 A | 6/1990 | Turchan | 29/566 |
| 4,935,200 A | 6/1990 | LaSalle et al. | 420/3 |
| 4,940,404 A | 7/1990 | Ammon et al. | 419/28 |
| 4,944,756 A | 7/1990 | Kenna | 623/20 |
| 4,957,510 A | 9/1990 | Cremascoli | 623/23 |
| 4,959,066 A | 9/1990 | Dunn et al. | 606/89 |
| 4,959,071 A | 9/1990 | Brown et al. | 623/20 |
| 4,961,383 A | 10/1990 | Fishman et al. | 102/517 |
| 4,964,766 A | 10/1990 | Turchan et al. | 409/225 |
| 4,964,868 A | 10/1990 | Bloebaum | 623/20 |
| 4,966,750 A | 10/1990 | LaSalle et al. | 420/3 |
| 4,969,910 A | 11/1990 | Frey et al. | 623/22 |
| 4,979,957 A | 12/1990 | Hodorek | 623/20 |
| 4,992,298 A | 2/1991 | Deutchman et al. | 427/38 |
| 5,002,578 A | 3/1991 | Luman | 623/23 |
| 5,002,579 A | 3/1991 | Copf et al. | 623/23 |
| 5,002,580 A | 3/1991 | Noble et al. | 623/23 |
| 5,002,581 A | 3/1991 | Paxson et al. | 623/23 |
| 5,009,673 A | 4/1991 | Cho | 51/293 |
| 5,011,515 A | 4/1991 | Frushour | 51/307 |
| 5,019,103 A | 5/1991 | Van Zile et al. | 623/20 |
| 5,022,894 A | 6/1991 | Vagarali et al. | 51/293 |
| 5,030,233 A | 7/1991 | Ducheyne | 623/16 |
| 5,037,423 A | 8/1991 | Kenna | 606/88 |
| 5,037,439 A | 8/1991 | Albrektsson et al. | 623/20 |
| 5,037,451 A | 8/1991 | Burnand et al. | 51/293 |
| 5,047,060 A | 9/1991 | Henssge et al. | 623/23 |
| 5,047,062 A | 9/1991 | Pappas et al. | 623/23 |
| 5,052,339 A | 10/1991 | Vakerlis et al. | 118/723 |
| 5,054,246 A | 10/1991 | Phaal et al. | 51/204 |
| 5,054,682 A | 10/1991 | Mistry | 228/194 |
| 5,055,318 A | 10/1991 | Deutchman et al. | 427/38 |
| RE33,767 E | 12/1991 | Christini et al. | 428/544 |
| 5,080,685 A | 1/1992 | Bolesky et al. | 623/23 |
| 5,080,752 A | 1/1992 | Kabacoff et al. | 156/603 |
| 5,082,359 A | 1/1992 | Kirkpatrick | 359/642 |
| 5,092,687 A | 3/1992 | Hall | 384/303 |
| 5,092,895 A | 3/1992 | Albrektsson et al. | 623/20 |
| 5,092,898 A | 3/1992 | Bekki et al. | 623/22 |
| 5,108,432 A | 4/1992 | Gustavson | 623/16 |
| 5,108,451 A | 4/1992 | Forte | 623/23 |
| 5,108,452 A | 4/1992 | Fallin | 623/23 |
| 5,116,380 A | 5/1992 | Hewka et al. | 623/23 |
| 5,120,327 A | 6/1992 | Dennis | 51/293 |
| 5,128,146 A | 7/1992 | Hirayama et al. | 424/484 |
| 5,133,757 A | 7/1992 | Sioshansi et al. | 623/18 |
| 5,133,758 A | 7/1992 | Hollister | 623/20 |
| 5,133,763 A | 7/1992 | Mullers | 623/22 |
| 5,152,794 A | 10/1992 | Davidson | 623/16 |
| 5,152,795 A | 10/1992 | Soishansi et al. | 623/16 |
| 5,154,023 A | 10/1992 | Sioshansi | 51/323 |
| 5,154,245 A | 10/1992 | Waldenstrom et al. | 175/420.2 |
| 5,156,624 A | 10/1992 | Barnes | 623/22 |
| 5,163,963 A | 11/1992 | Hewka et al. | 623/23 |
| 5,171,282 A | 12/1992 | Pequignot | 623/20 |
| 5,171,283 A | 12/1992 | Pappas et al. | 623/20 |

| Patent No. | Date | Inventor | Class |
|---|---|---|---|
| 5,181,926 A | 1/1993 | Koch et al. ................ | 623/22 |
| 5,181,928 A | 1/1993 | Bolesky et al. ............. | 623/23 |
| 5,192,323 A | 3/1993 | Shetty et al. ............... | 623/16 |
| 5,194,066 A | 3/1993 | Van Zile ..................... | 623/20 |
| 5,197,987 A | 3/1993 | Koch et al. ................. | 623/20 |
| 5,211,726 A | 5/1993 | Slutz et al. .................. | 51/293 |
| 5,217,081 A | 6/1993 | Waldenstrom et al. ... | 175/420.2 |
| 5,248,317 A | 9/1993 | Tank et al. .................. | 51/293 |
| 5,258,022 A | 11/1993 | Davidson ..................... | 623/2 |
| 5,258,033 A | 11/1993 | Lawes et al. ................ | 623/23 |
| 5,264,283 A | 11/1993 | Waldenstrom et al. ..... | 428/408 |
| 5,284,483 A | 2/1994 | Johnson et al. ............. | 606/86 |
| 5,304,192 A | 4/1994 | Crouse ....................... | 606/181 |
| 5,304,342 A * | 4/1994 | Hall, Jr. et al. | |
| 5,308,412 A | 5/1994 | Shetty et al. ............... | 148/238 |
| 5,310,408 A | 5/1994 | Schryver et al. ............ | 623/22 |
| 5,326,361 A | 7/1994 | Hollister ...................... | 623/20 |
| 5,326,362 A | 7/1994 | Shetty et al. ............... | 623/66 |
| 5,330,481 A | 7/1994 | Hood et al. ................. | 606/99 |
| 5,330,532 A | 7/1994 | Ranawat ..................... | 623/20 |
| 5,330,826 A | 7/1994 | Taylor et al. ............... | 428/216 |
| 5,333,954 A | 8/1994 | Noguchi et al. ............. | 384/26 |
| 5,335,738 A | 8/1994 | Waldenstrom et al. ... | 175/420.2 |
| 5,348,108 A | 9/1994 | Scott et al. .................. | 175/432 |
| 5,351,772 A | 10/1994 | Smith .......................... | 175/428 |
| 5,355,750 A | 10/1994 | Scott et al. ................. | 76/108.2 |
| 5,355,969 A | 10/1994 | Hardy et al. ................ | 175/432 |
| 5,358,525 A | 10/1994 | Fox et al. .................... | 623/18 |
| 5,358,529 A | 10/1994 | Davidson .................... | 623/20 |
| 5,358,532 A | 10/1994 | Evans et al. ................ | 623/22 |
| 5,360,341 A | 11/1994 | Abramowitz ............... | 433/215 |
| 5,364,192 A | 11/1994 | Damm et al. ............... | 384/420 |
| 5,368,398 A | 11/1994 | Damm et al. ............... | 384/303 |
| 5,370,694 A | 12/1994 | Davidson .................... | 623/16 |
| 5,370,700 A | 12/1994 | Sarkisian et al. ........... | 623/20 |
| 5,370,717 A | 12/1994 | Lloyd et al. ................. | 51/293 |
| 5,372,660 A | 12/1994 | Davidson et al. ........... | 148/421 |
| 5,376,444 A | 12/1994 | Grotenpass et al. ........ | 428/336 |
| 5,379,853 A | 1/1995 | Lockwood et al. ......... | 175/428 |
| 5,379,854 A | 1/1995 | Dennis ........................ | 175/434 |
| 5,380,547 A | 1/1995 | Higgins ....................... | 427/2.26 |
| 5,383,934 A | 1/1995 | Armini et al. ............... | 623/16 |
| 5,387,247 A | 2/1995 | Vallana et al. ............... | 623/66 |
| 5,391,407 A | 2/1995 | Dearnaley ................... | 427/527 |
| 5,391,409 A | 2/1995 | Shibata et al. .............. | 427/577 |
| 5,391,422 A | 2/1995 | Omori et al. ................ | 428/212 |
| 5,401,269 A | 3/1995 | Buttner-Janz et al. ...... | 623/17 |
| 5,405,394 A | 4/1995 | Davidson .................... | 623/18 |
| 5,411,555 A | 5/1995 | Nieder ........................ | 623/20 |
| 5,413,438 A | 5/1995 | Turchan ...................... | 409/66 |
| 5,413,814 A | 5/1995 | Bowen et al. ............... | 427/262 |
| 5,414,049 A | 5/1995 | Sun et al. .................... | 525/333.7 |
| 5,415,704 A | 5/1995 | Davidson .................... | 148/316 |
| 5,421,425 A | 6/1995 | Griffin ........................ | 175/432 |
| 5,429,459 A | 7/1995 | Palm ........................... | 409/66 |
| 5,429,883 A | 7/1995 | Sasaki et al. ................ | 428/678 |
| 5,435,403 A | 7/1995 | Tibbits ........................ | 175/432 |
| 5,441,488 A | 8/1995 | Shimura et al. ............. | 604/265 |
| 5,449,048 A | 9/1995 | Thigpen et al. ............. | 175/430 |
| 5,451,365 A | 9/1995 | Barsoum .................... | 419/10 |
| 5,458,827 A | 10/1995 | Holly ........................... | 264/400 |
| 5,469,927 A | 11/1995 | Griffin ........................ | 175/432 |
| 5,478,906 A | 12/1995 | Howard, Jr. ................ | 526/352 |
| 5,485,496 A | 1/1996 | Lee et al. .................... | 378/64 |
| 5,486,137 A | 1/1996 | Flood et al. ................. | 451/540 |
| 5,492,188 A | 2/1996 | Smith et al. ................. | 175/432 |
| 5,494,477 A | 2/1996 | Flood et al. ................. | 451/540 |
| 5,496,318 A | 3/1996 | Howland et al. ............ | 606/61 |
| 5,498,302 A | 3/1996 | Davidson .................... | 148/317 |
| 5,499,688 A | 3/1996 | Dennis ........................ | 175/426 |
| 5,507,804 A | 4/1996 | Llanos ........................ | 623/11 |
| 5,507,814 A | 4/1996 | Gilbert et al. ............... | 623/16 |
| 5,507,824 A | 4/1996 | Lennox ....................... | 623/22 |
| 5,507,830 A | 4/1996 | DeMane et al. ............. | 623/23 |
| 5,508,368 A | 4/1996 | Knapp et al. ................ | 427/534 |
| 5,512,235 A | 4/1996 | Cerutti et al. ................ | 419/10 |
| RE35,255 E | 5/1996 | Turchan ...................... | 409/74 |
| 5,514,182 A | 5/1996 | Shea .......................... | 623/18 |
| 5,514,183 A | 5/1996 | Epstein et al. .............. | 623/20 |
| 5,514,184 A | 5/1996 | Doi et al. .................... | 623/23 |
| 5,516,500 A | 5/1996 | Liu et al. ..................... | 423/466 |
| 5,518,969 A | 5/1996 | Ragan ......................... | 501/32 |
| 5,525,537 A | 6/1996 | Zachai et al. ............... | 437/103 |
| 5,530,072 A | 6/1996 | Shirodkar ................. | 525/333.8 |
| 5,544,713 A | 8/1996 | Dennis ........................ | 175/434 |
| 5,549,190 A | 8/1996 | Turchan ...................... | 198/403 |
| 5,549,690 A | 8/1996 | Hollister et al. ............. | 623/21 |
| 5,549,700 A | 8/1996 | Graham et al. .............. | 623/22 |
| 5,554,415 A | 9/1996 | Turchan et al. ............. | 427/248 |
| 5,556,464 A | 9/1996 | Tanabe et al. ............... | 117/106 |
| 5,560,716 A | 10/1996 | Tank et al. ................... | 384/492 |
| 5,564,511 A | 10/1996 | Frushour ..................... | 175/431 |
| 5,566,779 A | 10/1996 | Dennis ........................ | 175/426 |
| 5,571,195 A | 11/1996 | Johnson ...................... | 623/18 |
| 5,571,203 A | 11/1996 | Masini ......................... | 623/23 |
| 5,571,616 A | 11/1996 | Phillips et al. .............. | 428/336 |
| 5,590,727 A | 1/1997 | Tank et al. ................... | 175/374 |
| 5,590,728 A | 1/1997 | Matthias et al. ............. | 175/432 |
| 5,590,729 A | 1/1997 | Cooley et al. ............... | 175/432 |
| 5,591,233 A | 1/1997 | Kelman et al. .............. | 623/16 |
| 5,593,719 A | 1/1997 | Dearnaley et al. .......... | 427/2.26 |
| 5,601,477 A | 2/1997 | Bunting et al. .............. | 451/59 |
| 5,605,198 A | 2/1997 | Tibbits et al. ............... | 175/432 |
| 5,605,199 A | 2/1997 | Newton ...................... | 175/432 |
| 5,605,714 A | 2/1997 | Dearnaley et al. .......... | 427/2.24 |
| 5,605,938 A | 2/1997 | Roufa et al. ................. | 514/59 |
| 5,611,649 A | 3/1997 | Matthias ..................... | 407/118 |
| 5,617,928 A | 4/1997 | Matthias et al. ............. | 175/432 |
| 5,620,285 A | 4/1997 | Turchan ...................... | 409/132 |
| 5,620,754 A | 4/1997 | Turchan et al. ............. | 427/554 |
| 5,621,965 A | 4/1997 | Turchan ...................... | 29/559 |
| 5,622,233 A | 4/1997 | Griffin ........................ | 175/432 |
| 5,624,068 A | 4/1997 | Waldenstrom et al. . | 228/262.21 |
| 5,630,479 A | 5/1997 | Dennis ........................ | 175/426 |
| 5,633,087 A | 5/1997 | Simpson ..................... | 428/408 |
| 5,635,243 A | 6/1997 | Turchan et al. ............. | 427/248 |
| 5,641,323 A | 6/1997 | Caldarise .................... | 623/22 |
| 5,641,324 A | 6/1997 | Bokros et al. ............... | 623/2 |
| 5,641,921 A | 6/1997 | Dennis et al. ............... | 75/230 |
| 5,643,641 A | 7/1997 | Turchan et al. ............. | 427/595 |
| 5,645,601 A | 7/1997 | Pope et al. .................. | 623/18 |
| 5,645,605 A | 7/1997 | Klawitter .................... | 623/21 |
| 5,647,449 A | 7/1997 | Dennis ........................ | 175/434 |
| 5,647,704 A | 7/1997 | Turchan ...................... | 409/131 |
| 5,648,127 A | 7/1997 | Turchan et al. ............. | 427/596 |
| 5,660,075 A | 8/1997 | Johnson et al. ............. | 72/467 |
| 5,667,028 A | 9/1997 | Truax et al. ................. | 175/428 |
| 5,669,271 A | 9/1997 | Griffin et al. ............... | 76/108.2 |
| 5,669,913 A | 9/1997 | Zobel .......................... | 606/85 |
| 5,676,632 A | 10/1997 | Davidson .................... | 600/16 |
| 5,676,704 A | 10/1997 | Ries et al. ................... | 623/18 |
| 5,677,061 A | 10/1997 | Ely et al. ..................... | 428/408 |
| 5,683,442 A | 11/1997 | Davidson .................... | 607/116 |
| 5,685,306 A | 11/1997 | Davidson .................... | 128/658 |
| 5,685,671 A | 11/1997 | Packer et al. ................ | 407/54 |
| 5,690,670 A | 11/1997 | Davidson .................... | 606/198 |
| 5,693,090 A | 12/1997 | Unsworth et al. ........... | 623/2 |
| 5,702,448 A | 12/1997 | Buechel et al. ............. | 623/16 |
| 5,702,473 A | 12/1997 | Albrektsson et al. ........ | 623/22 |
| 5,702,487 A | 12/1997 | Averill et al. ............... | 623/23 |
| 5,706,906 A | 1/1998 | Jurewicz et al. ............ | 175/428 |
| 5,713,947 A | 2/1998 | Davidson .................... | 623/1 |

| Patent No. | Date | Inventor | Class |
|---|---|---|---|
| 5,716,400 A | 2/1998 | Davidson | 623/2 |
| 5,725,573 A | 3/1998 | Dearnaley et al. | 623/2 |
| 5,725,582 A | 3/1998 | Bevan et al. | 623/17 |
| 5,728,161 A | 3/1998 | Camino et al. | 623/19 |
| 5,755,800 A | 5/1998 | O'Neil et al. | 623/20 |
| 5,766,255 A | 6/1998 | Slamin et al. | 623/20 |
| 5,766,394 A | 6/1998 | Anderson et al. | 156/89.11 |
| 5,769,891 A | 6/1998 | Clayton | 623/10 |
| 5,773,140 A | 6/1998 | Cerutti et al. | 428/332 |
| 5,782,910 A | 7/1998 | Davidson | 623/2 |
| 5,787,022 A | 7/1998 | Tibbits et al. | 364/578 |
| 5,800,560 A | 9/1998 | Draenert | 623/23 |
| 5,824,062 A | 10/1998 | Patke et al. | 623/2 |
| 5,824,101 A | 10/1998 | Pappas | 623/20 |
| 5,824,651 A | 10/1998 | Nanci et al. | 514/21 |
| 5,830,539 A | 11/1998 | Yan et al. | 427/551 |
| 5,855,601 A | 1/1999 | Besler et al. | 623/2 |
| 5,855,996 A | 1/1999 | Corrigan et al. | 428/212 |
| 5,861,042 A | 1/1999 | Buechel et al. | 623/16 |
| 5,868,796 A | 2/1999 | Buechel et al. | 623/16 |
| 5,868,885 A | 2/1999 | Crockett et al. | 156/89.27 |
| 5,875,862 A | 3/1999 | Jurewicz et al. | 175/432 |
| 5,876,459 A | 3/1999 | Powell | 623/18 |
| 5,879,397 A | 3/1999 | Kalberer et al. | 623/22 |
| 5,879,404 A | 3/1999 | Bateman et al. | 623/22 |
| 5,879,405 A | 3/1999 | Ries et al. | 623/22 |
| 5,879,407 A | 3/1999 | Waggener | 623/22 |
| 5,888,208 A | 3/1999 | Ro | 623/23 |
| 5,895,388 A | 4/1999 | Zobel | 606/85 |
| 5,898,388 A | 4/1999 | Hoffman et al. | 340/870.13 |
| 5,906,644 A | 5/1999 | Powell | 623/23 |
| 5,924,501 A | 7/1999 | Tibbits | 175/429 |
| 5,928,131 A | 7/1999 | Prem | 600/16 |
| 5,944,129 A | 8/1999 | Jensen | 175/430 |
| 5,950,747 A | 9/1999 | Tibbits et al. | 175/432 |
| 5,979,579 A | 11/1999 | Jurewicz | 175/434 |
| 5,981,827 A | 11/1999 | Devlin et al. | 623/16 |
| 6,000,483 A | 12/1999 | Jurewicz et al. | 175/428 |
| 6,006,846 A | 12/1999 | Tibbits et al. | 175/428 |
| 6,007,577 A | 12/1999 | Vanney et al. | 623/2 |
| 6,021,859 A | 2/2000 | Tibbits et al. | 175/431 |
| 6,045,497 A | 4/2000 | Schweich, Jr. et al. | 600/16 |
| 6,045,877 A | 4/2000 | Gleason et al. | 457/522 |
| 6,063,149 A * | 5/2000 | Zimmer | |
| 6,068,071 A | 5/2000 | Jurewicz | 175/432 |
| 6,077,148 A | 6/2000 | Klein et al. | 451/11 |
| 6,082,223 A | 7/2000 | Tibbits | 76/108.2 |
| 6,290,726 B1 * | 9/2001 | Pope et al. | 623/18.11 |
| 6,315,065 B1 * | 11/2001 | Yong et al. | |
| 6,398,815 B1 * | 6/2002 | Pope et al. | |
| 6,402,787 B1 * | 6/2002 | Pope et al. | |
| 6,425,922 B1 * | 7/2002 | Pope et al. | |
| 6,494,918 B1 * | 12/2002 | Pope et al. | |
| 6,497,727 B1 * | 12/2002 | Pope et al. | |
| 6,514,289 B1 * | 2/2003 | Pope et al. | |
| 6,610,095 B1 * | 8/2003 | Pope et al. | |

\* cited by examiner

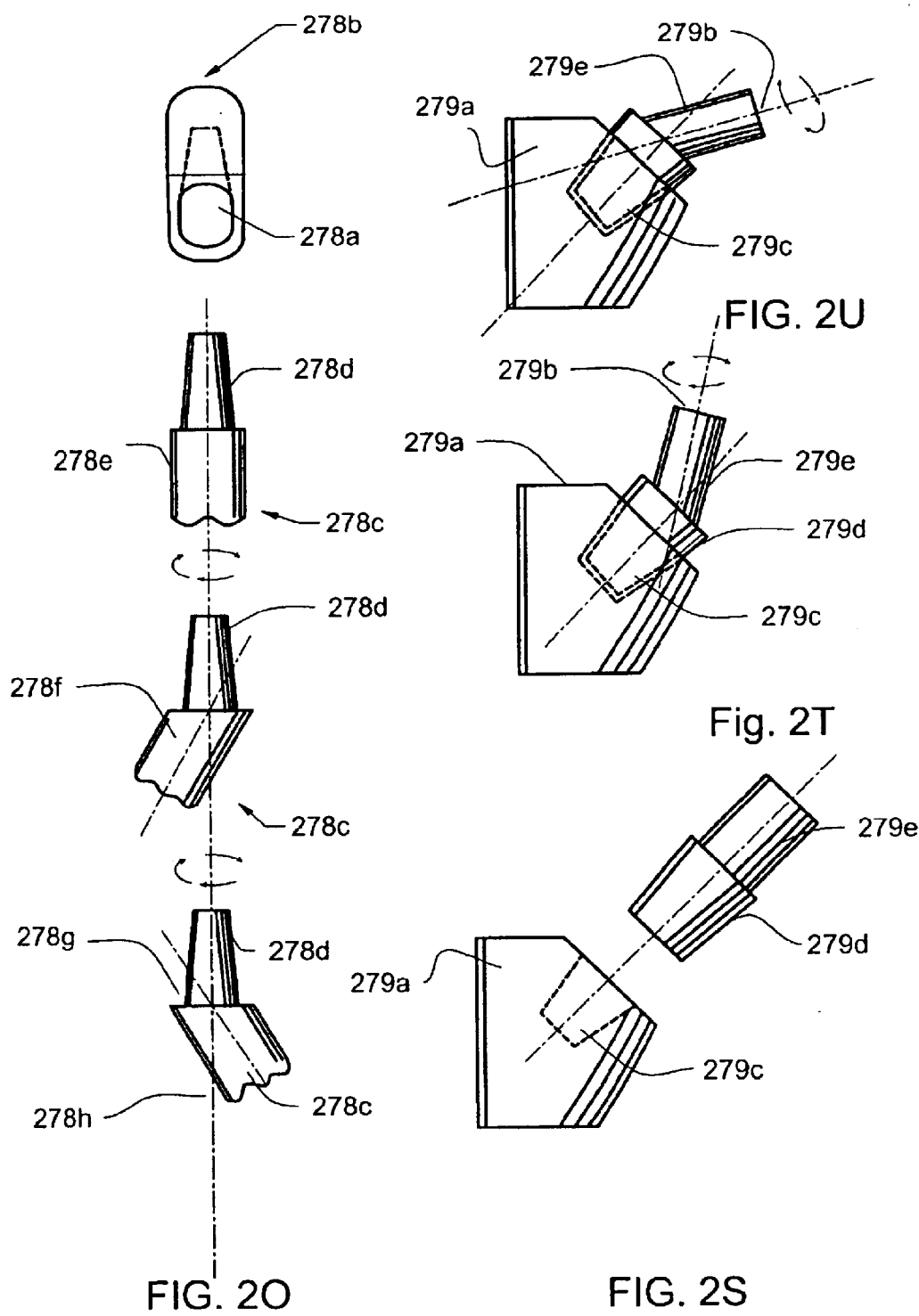

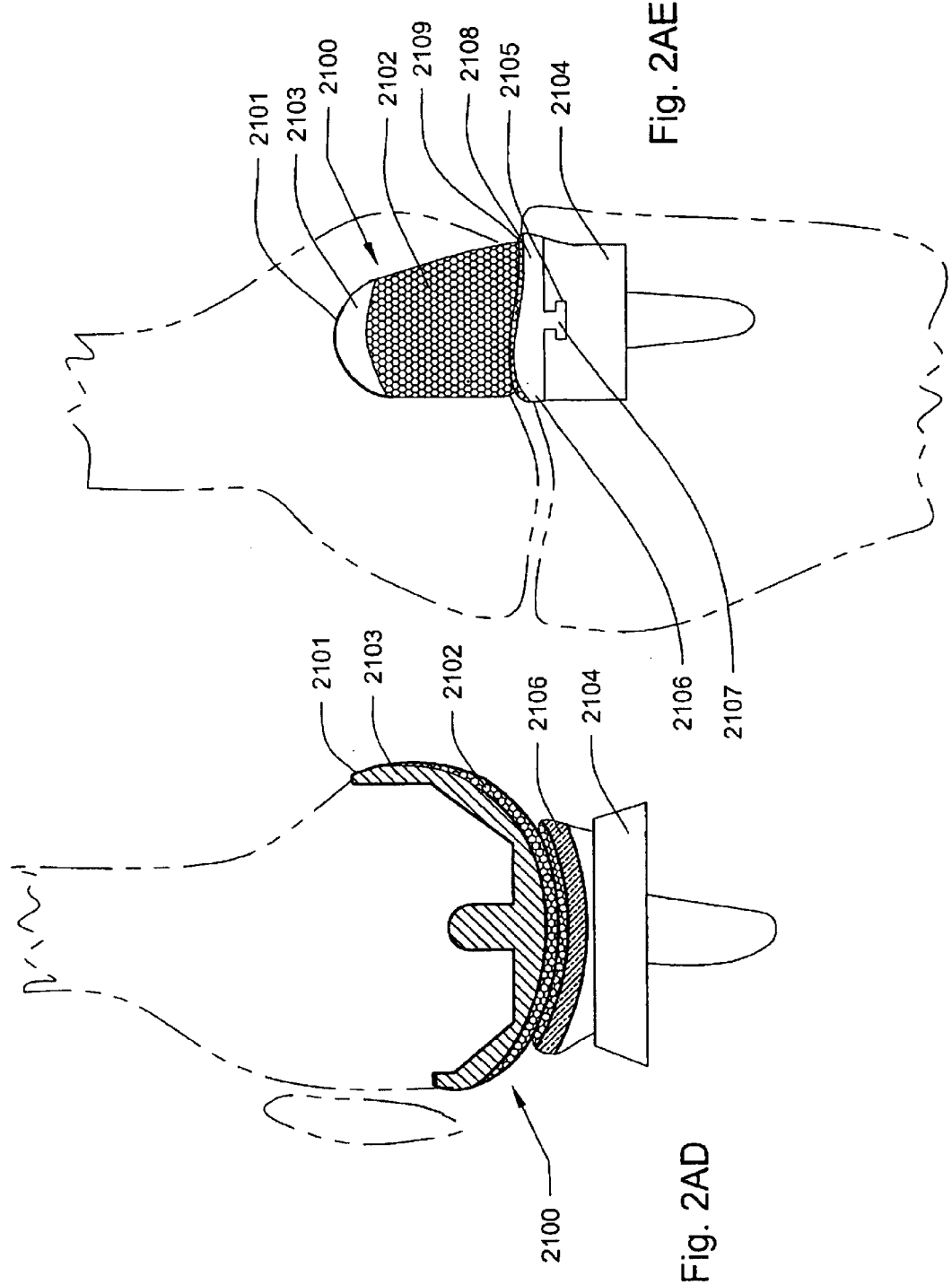

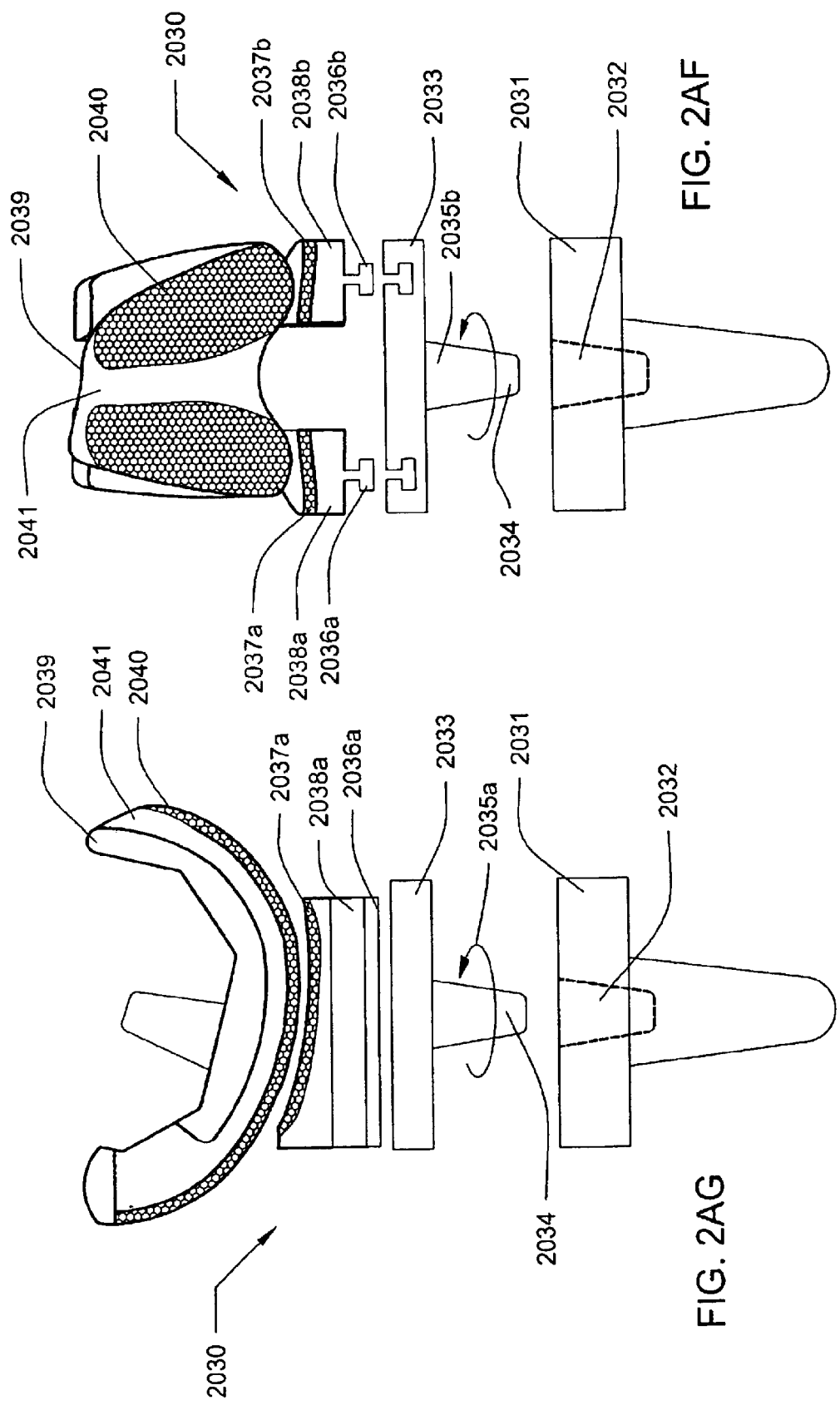

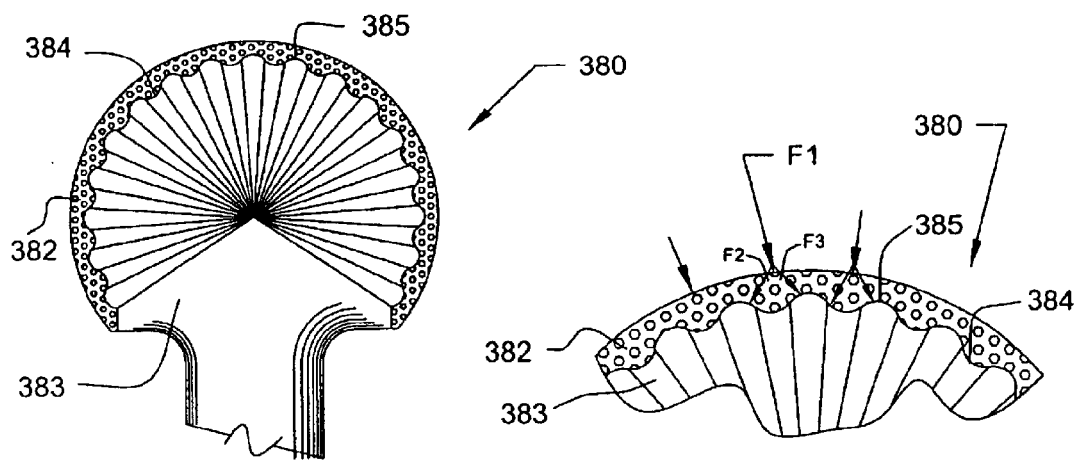
Fig. 3A
Fig. 3B
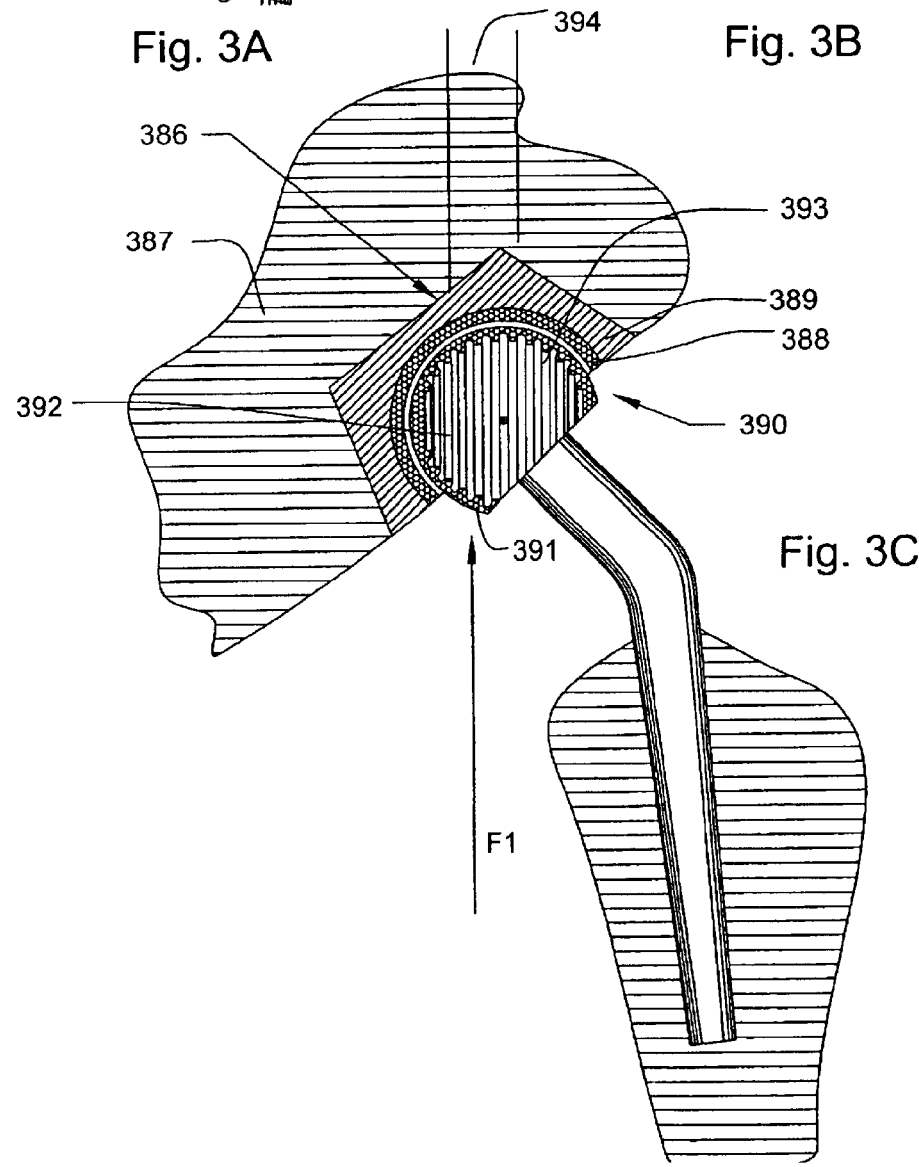
Fig. 3C

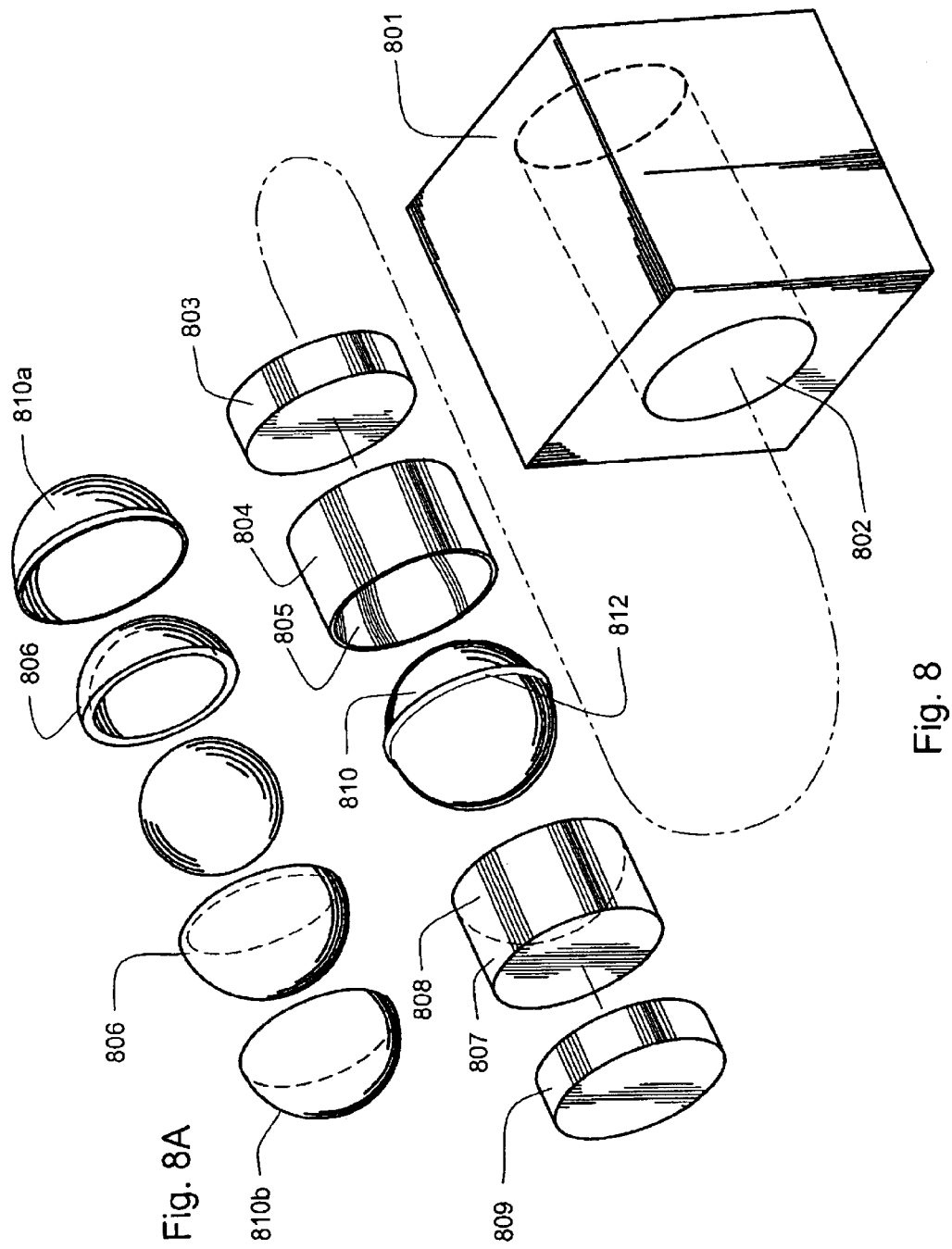

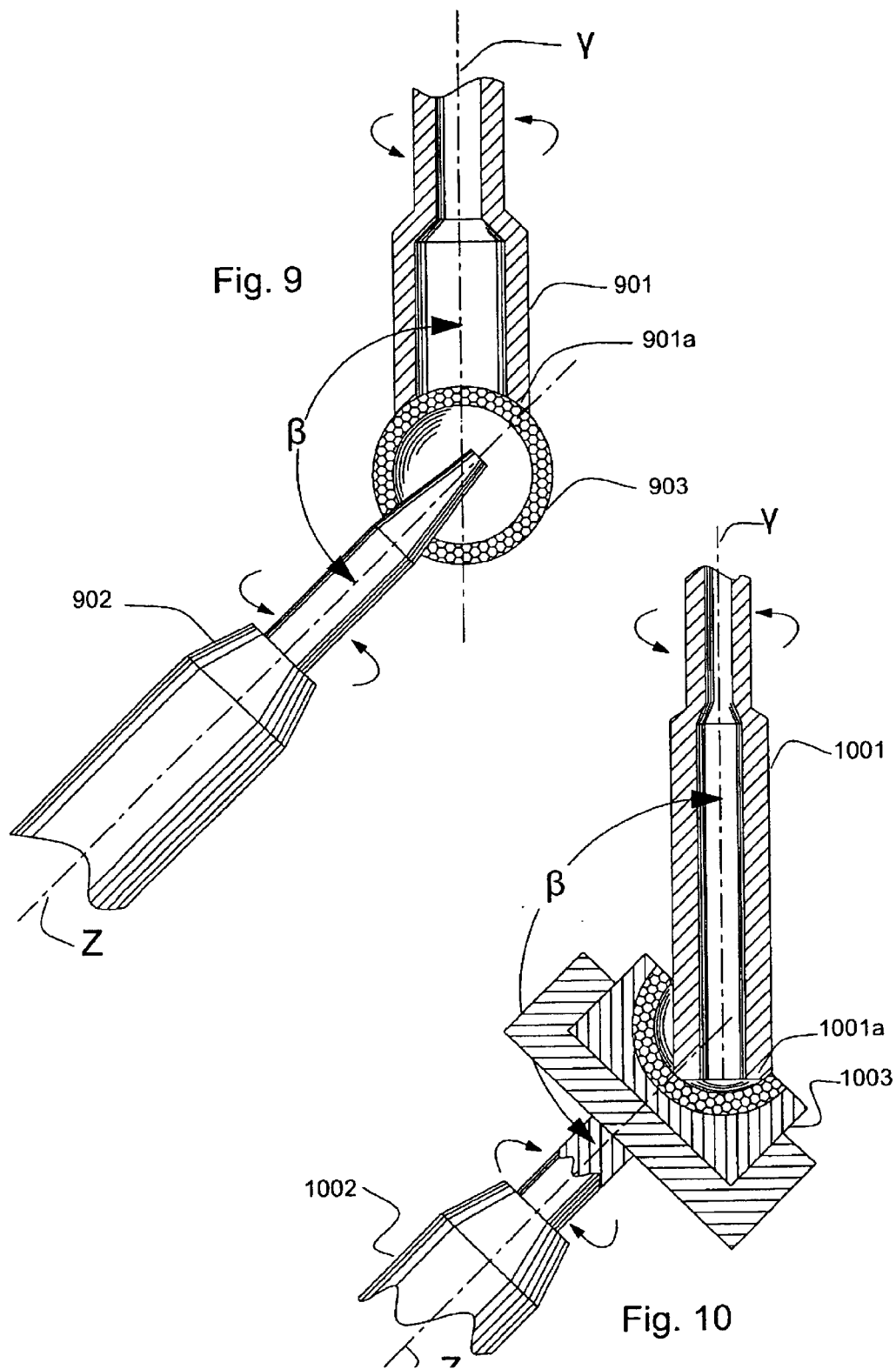

Fig. 11
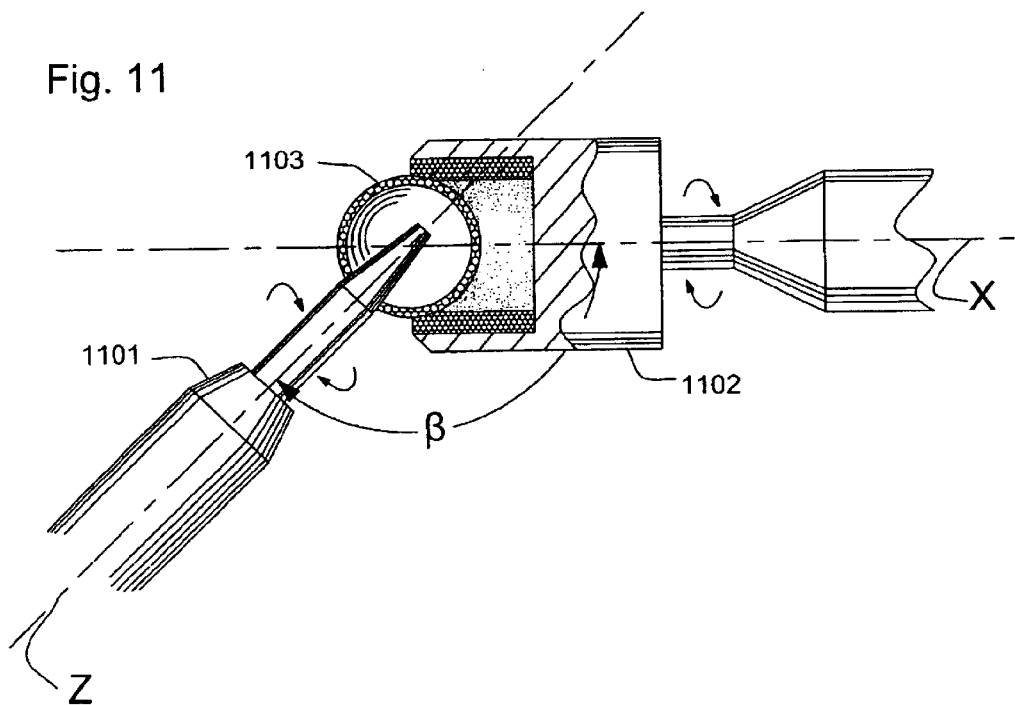
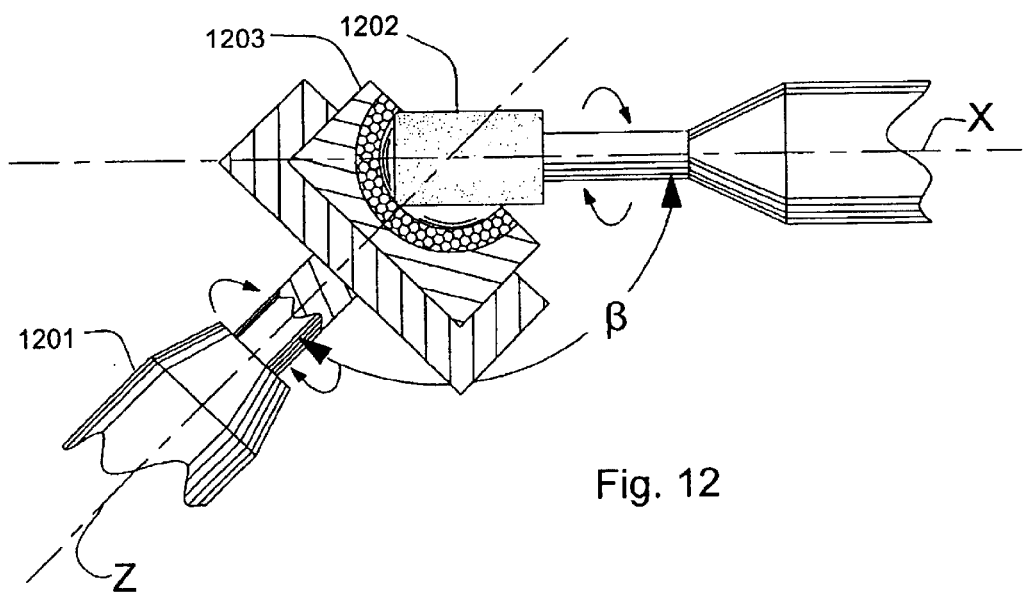
Fig. 12

DIAMOND-SURFACED FEMORAL HEAD FOR USE IN A PROSTHETIC JOINT

CLAIM FOR PRIORITY

This patent application is a continuation-in-part of U.S. patent application Ser. No. 09/457,226 filed on Dec. 8, 1999, now abandoned, which is a continuation of U.S. patent application Ser. No. 8/844,395 filed on Apr. 18, 1997, now U.S. Pat. No. 6,010,533, which is a continuation of U.S. patent application Ser. No. 08/631,877, filed on Apr. 16, 1996, now U.S. Pat. No. 5,645,601, which is a continuation of U.S. patent application Ser. No. 08/289,696 filed on Aug. 12, 1994, now abandoned, and priority is claimed to each of them.

BACKGROUND OF THE INVENTION

A. Field of the Invention

Various embodiments of the invention relate to superhard surfaces and components of various compositions and shapes, methods for making those superhard surfaces and components, and products, which include those superhard surfaces and components. Such products include biomedical devices such as prosthetic joints and other devices. More specifically, some preferred embodiments of the invention relate to diamond and polycrystalline diamond bearing surfaces and prosthetic joints that include diamond and polycrystalline diamond bearing surfaces. Some preferred embodiments of the invention utilize a polycrystalline diamond compact ("PDC") to provide a very strong, low friction, long-wearing and biocompatible bearing surface in a prosthetic joint. Any bearing surface, including bearing surfaces outside the field of prosthetic joints, which experience wear and require strength and durability will benefit from embodiments of the invention.

B. Description of Related Art

This section will discuss art related to prosthetic joint bearing surfaces. Artificial joint replacement has become a widely accepted successful medical practice in the treatment of arthritic or deformed joints. Hundreds of thousands of joint replacement procedures are performed every year. Prosthetic hip and knee replacement comprise the vast majority of these procedures, however many other joints are also treated as well including, but not limited to, the shoulder, elbow, wrist, ankle, and temparomandibular joints. Additionally, there are other joints, such as the intervertebral disk joint of the spine, which are not commonly replaced with prosthetic joints, but which might be amenable to such treatment to remedy disease states if sufficiently durable materials in functional designs were available.

The ideal total artificial joint prosthesis can be characterized in terms of flexibility, durability, and compatibility. Flexibility: An ideal total joint prosthesis should restore a normal range of motion, allowing all activities possible with a normal natural joint without an increase in the relative risk of dislocation. Durability: The mechanical parts of the articulation should function without wearing out or breaking, and the implant's fixation to the recipient's skeleton should remain rigidly intact for the duration of the recipient's lifetime, without requiring restrictions on the intensity of activities or the degree of load bearing beyond those applying to a natural joint. Compatibility: The prosthetic materials and wear byproducts should be biocompatible, and should not elicit toxic, inflammatory, immunologic, or other deleterious reactions in the host recipient. Currently available devices fall short of fulfilling these criteria in one or more significant ways. It is the objective of the current invention to improve upon the prior technologies in terms of meeting these criteria.

In general, there are two types of artificial joints—articulating joints and flexible hinge joints. Articulating joints include hip, knee, shoulder, ankle and other joints. Flexible hinge joints include silastic and metacarpalphalangeal joints. In the past, articulating joints have consisted typically of a hard surface (metal or ceramic) mated to a plastic surface (ultra high molecular weight polyethylene). Other joints have been composed of variations of hard on hard articulations (metal on metal and ceramic on ceramic). Articulating joints may take a myriad of configurations including variations on a ball in socket design, such as with a hip and shoulder joint, and variations on a hinge design as with a knee, elbow, or metacarpalphalangeal joint. In every case, the prosthesis is designed to restore to the greatest extent possible, the functional range of motion, and mechanical stability of the affected joint.

As a detailed example of problems found in the prior art, we will review the hip joint. It includes a convex spherical ball (femoral head) and a concave socket (acetabular socket) articulation. Hip joint replacement consists of replacing the damaged articular surfaces with new articulating bearing surfaces. On the acetabluar side, a hemisphere-like cup is placed in the patient's damaged or worn socket, and fixed by some means to the patient's bone. On the femoral side, the prosthetic replacement consists of a sphere-like ball designed to fit into, and articulate with the prosthetic acetabular cup. The sphere-like ball may be a resurfacing device designed to fit over the patient's own femoral head (so called "surface replacement"). Or more commonly it consists of a ball attached to a stem, which is inserted into the femoral canal anchoring the prosthesis to the patient's femur. The ball and socket work as a pair in similar fashion to the original hip, restoring a partial range of linear and rotational motion.

Alternatively, only a surface replacement or a ball and stem set are provided without a corresponding socket for a hemiarthroplasty procedure (discussed below). For total hip joint replacement, the most commonly used device consists of a metal head articulation with a high density ultra high molecular weight polyethylene (UHMWPE) surface, but ceramic (alumina, and partially stabilized zirconia) heads are also used, having certain advantages as well as disadvantages relative to their metal counterparts. Metal on metal, and ceramic on ceramic articulations are also used in routine medical practice elsewhere in the world, and are being used on an investigational basis in the United States.

Replacement of only one half of the hip joint is called hemiarthroplasty. This is performed when only one of the articulating portions of the joint is damaged, as with avascular necrosis of the femoral head, or in the case of a hip fracture that is not amenable to repair. The damaged portion is replaced with a prosthetic articulation designed to function with the remaining natural biological portion of the joint. The requirements are somewhat different here than with a total articular replacement, in that the artificial portion must match the contours of the anatomic segment, and must be conducive to preservation of the function of the natural segment. This would include having a surface smooth enough to minimize wear and tear to the natural joint surface, and optimization of surface material properties and contours that would encourage entrainment of joint fluid into the joint space. This entrainment of synovial fluid is essential to minimize wear to, and maintain nutrition and function of the biological joint surface.

Prosthetic joint implants must be securely anchored to the recipient's bone to function properly. This fixation may be achieved through the use of cementing agents, typically consisting of polymethylmethacrylate cement, through biological fixation techniques including direct osseointegration to metal or ceramic fixation surfaces and bone ingrowth into porous surfaces on implant surfaces, or through a mechanical interference press fit between the implant and the host bone. Preservation and maintenance of this secure fixation is critical to the long-term success of the prosthetic construct.

When evaluating prior art technology relative to the criteria previously established for an ideal prosthetic joint, we find that metal balls articulating with polyethylene cups do not provide optimal results. Due to geometric restrictions on the implant design imposed by implant material properties, and anatomic constraints, artificial hips have a decreased safe range of motion compared to normal natural counterparts. The polyethylene bearings may wear through after between 5 and 20 years of service, depending upon factors such as patient age, weight and activity level. The particulate debris resulting from this normal wear often results in inflammatory reactions in the bone surrounding and anchoring the implants, resulting in severe erosion of the bone. This is called "osteolysis" and has proven to be a most prevalent cause of failure and subsequent artificial joint replacement.

The normal metal to ultra high molecular weight polyethylene ("UHMWPE") articulation of artificial joints results in the generation of billions of submicron polyethylene wear particles. It is the accumulation of this wear-related debris and the immune system's reaction to it that results in the inflammatory response, which causes osteolysys. It is also the cumulative effect of this continual wear of UHMWPE that results in wear through of the mechanical joint and bearing failure. The younger and more active the patient, the shorter the anticipated functional life of the implant. Thus, those patients who, because of their youth, need the greatest durability from their implants, typically have the least durability.

Osteolysis can cause loosening of the critical implant-bone fixation, and may result in increased risk of fracture of the bone around the implants. Wear through of the components and/or periprosthetic osteolysis of the host bone with associated implant loosening and/or periprosthetic bone fracture requires major surgical intervention to remove the failed implants, reconstruct the damaged bone, and replace the failed prosthesis with a new artificial joint. This revision surgery is typically much more complicated than the initial implant surgery, and carries with it increased risks for perioperative complications, as well as increased risks for implant failure as compared to primary artificial joint replacement. Subsequent failures require further complex surgical intervention, with continually increasing risks of perioperative complications and early implant failure with each episode.

In order to reduce the risks of dislocation, recipients of artificial hips must restrict their range of motion in normal activities, compromising their ability to engage in many routine activities possible with normal natural joints. In order to decrease the rate of bearing wear which leads to implant failure due to bearing wear through and/or problems resulting from debris related osteolysis, they must also restrict their activities in terms of intensity, and duration relative to that routinely possible with normal natural joints.

In an effort to reduce the risk of dislocation, larger diameter bearings have been tried where the recipient's anatomy permits use of larger components. Surface replacement lies at the limit of this approach, and employs large bearings covering the patient's own femoral head remnant, articulating with a relatively thin UHMWPE acetabular component. Use of larger diameter bearings results in some increase in safe range of motion of the joint. Unfortunately, in the metal/UHMWPE bearing couple, increasing bearing diameter leads to increased rates of debris generation together with increased risk of its associated problems. In the case of surface replacements, the thin UHMWPE is particularly susceptible to accelerated wear, osteolysis, and failure.

The prior art includes many proposed improvements over the typical metal ball and polyethylene cup articulation seeking to decrease these problems of limited motion, wear, and debris-related osteolysis.

Ceramic bearings have some advantages over prior art metals in a prosthetic joint system. Ceramic bearings have an increased wettability compared to metal, resulting in better boundary layer lubrication, and they are resistant to the wear-promoting scratches that can develop in metal heads in the course of normal wear and tear in the joint. Both of these factors have contributed to the lower rates of wear and debris generation observed with ceramic on UHMWPE seen in both laboratory and clinical studies.

Unfortunately, ceramic bearings are structurally brittle. This limits the number of sizes and neck lengths that can be safely employed in reconstruction, restricting the options available to the surgeon to complete an optimal mechanical reconstruction during surgery. This intrinsic material brittleness can also lead to sudden implant fracture under impact, resulting in sudden and often catastrophic implant failure. Ceramic bearings also suffer from geometric design constraints similar to their metal-polyethylene counterparts, and have a similar susceptibility to dislocation if restrictions on range of motion are violated by the recipient. The limitations in ceramic material properties do not permit the fabrication of surface replacement bearings.

More recently, attention has turned to UHMWPE in an effort to improve the longevity of these bearing couples. Most early efforts to alter fabrication techniques, such as hot pressed components in hip and knee systems, and efforts to modify material structure, such as the addition of carbon fibers and the use of a hipping process to increase crystalinity, have resulted in no demonstrable improvements in clinical or in vitro performance, and in fact, have often resulted in poorer wear characteristics. Other techniques have improved function to a limited measurable extent, such as injection molding of components.

It has been found that the most common sterilization technique used to prepare UHMWPE components for implantation has had extreme unanticipated effects upon the material properties and wear characteristics of this material, resulting in accelerated wear and early failure in many cases. Study of this phenomenon, which includes the generation of chemical cross-links in polyethylene chains, and the generation of persistent free radicals within the polymer has led to further inventions to eliminate the deleterious effects of this process, while possibly taking advantage of potential beneficial effects that may actually improve the wear characteristics of polyethylene. These most recent developments, while demonstrating promising results in laboratory simulation studies, have yet to demonstrate improved function in widespread, long-term clinical studies. If these new polyethylene technologies do result in demonstrable improvements in function, the intrinsic problems of metal and ceramic counter bearings may still adversely affect long-term durability. Ultimate strength of UHMWPE (organic polyethylene bonds) in tension, compression and shear are low in comparison with metals, ceramics and diamond bonds. Diamond resistance to wear exceeds that of all other materials. The table below compares properties of polycrystalline diamond compact with some other materials from which bearing surfaces could be made.

TABLE 1

COMPARISON OF DIAMOND TO OTHER MATERIALS

| Material | Specific Gravity | Hardness (Knoop) | Thermal Conductivity (W/m K) | CTE ($\times 10^{-6}$) |
|---|---|---|---|---|
| Polycrystalline Diamond Compact | 3.5–4.0 | 9000 | 900 | 1.50–4.8 |
| Cubic Boron Nitride | 3.48 | 4500 | 800 | 1.0–4.0 |
| Silicon Carbide | 3.00 | 2500 | 84 | 4.7–5.3 |
| Aluminum Oxide | 3.50 | 2000 | | 7.8–8.8 |
| Tungsten Carbide (10% Co) | 14.6 | 2200 | 112 | 4–6 |
| Cobalt Chrome | 8.2 | 43 RC | | 16.9 |
| Ti6Al4V | 4.43 | | 6.6–17.5 | 11 |
| Silicon Nitride | 3.2 | 14.2 | 15–7 | 1.8–3.7 |

In order to avoid the potential problems of polyethylene entirely, others have turned to ceramic on ceramic and metal on metal contact surfaces. Ceramic on ceramic articulations have demonstrated improved wear rates, and excellent biocompatibility. However they suffer from the intrinsic limitation in material properties seen with ceramic heads used with polyethylene—brittleness and fracture risk. In addition, there is a tendency to develop catastrophic accelerated wear when a third body wear particle of sufficient hardness (such as another fragment of ceramic) is introduced into the articulation. Finally, the material property limitations of ceramic impose minimum material dimensional thicknesses that preclude the use of larger bearings or application as a surface replacement that would result in gains in effective range of motion.

Metal on metal bearings have also demonstrated improved volumetric rates of wear. And their material properties do make them suitable for application in large bearing applications and surface replacements effectively addressing the need for increased safe range of motion, and decreased risk of dislocation. However, concern still exists over the character of the wear debris of this metal-metal bearing couple. Though volumetric wear is quite low compared to polyethylene, particle size is extremely minute, on the order of 40–100 angstroms, resulting in an even larger total number of particles that with UHMWPE. These wear particles consist of cobalt-chrome-molybdenum alloy, which, with their extraordinarily large combined surface area, can result in significant release of metals ions with documented toxicity, and potential for long term carcinogenicity. It remains for long-term clinical studies to document the actual risk of this exposure, but significant questions have been raised with regard to this issue. As with ceramic on ceramic articulations, metal-to-metal bearings are susceptible to accelerated wear from third body wear particles.

Thus, the failures and pervasive defects of the prior art show a clear need for improved prosthetic joints. The various embodiments of the invention address the many deficiencies left by the prior art by providing prosthetic joints which are very long lasting, strong, have a low coefficient of friction, are biocompatible, experience little or no wear, and do not shed significant amounts of particles during use.

SUMMARY OF THE INVENTION

It is an object of some embodiments of the invention to provide components for prosthetic joint implants having increased wear resistance and a decreased coefficient of friction, therefore having maximum life of the replaced joint. It is a feature of some embodiments of the invention that diamond of various types and other superhard materials are used for the bearing surfaces of the joint, the superhard materials including diamond being very resistant to wear and having a very low coefficient of friction. For the purposes of this document, a superhard material is a material that has a Knoop hardness of at least about 4000. This includes diamond (whether natural diamond or synthetic diamond), cubic boron nitride and wurzitic boron nitride. It is a consequent advantage that the joint will likely not wear out during the lifetime of the user and will only generate insignificant amounts of benign wear particles.

It is an object of some embodiments of the invention to provide a prosthetic joint that does not shed significant amounts of debris or wear particles as a result of use or wear. It is a feature of some embodiments of the invention that polycrystalline diamond compacts or other superhard materials form at least one of the articulation surfaces of the joint, resulting in a low friction and long wearing joint that sheds little to no debris or particles during use. Therefore a lessened risk of osteolysis is a significant advantage of these embodiments of the invention.

It is another object of some preferred embodiments the invention to use the hardest materials known to man, namely diamond, cubic boron nitride and other superhard materials to give prosthetic joints the highest resistance to wear currently known to man. It is a feature of the invention that some preferred embodiments use polycrystalline diamond compact ("PDC") for a bearing surface. For the purposes of this document, a polycrystalline diamond compact includes a volume of synthetic diamond attached to a substrate material. The polycrystalline diamond is extremely hard and, when polished, has one of the lowest coefficients of friction of any known material. It is a consequent advantage of the invention that the joint life far exceeds that of the recipient. The polycrystalline diamond compact may be manufactured by a variety of methods, including high pressure and high temperature sintering in a press, chemical vapor deposition, physical vapor deposition, and others.

It is another object of some embodiments of the invention to provide joint components, which are completely biocompatible. The most preferred material used in some embodiments of the invention, polycrystalline diamond compact, is extremely biocompatible and elicits minimal or negligible immune response or other attack by the body. It is an advantage that the joint will be substantially less disruptive to the body's systems than prior art joints.

It is another object of some embodiments of the invention to provide improved geometry within the joint space in order to allow optimal utilization of superhard materials, including polycrystalline diamond compacts. The improved geometry is intended to limit stresses both residual and those imposed during service use. Due to the very hard and strong nature of the materials being utilized, the entire joint geometry can be optimized for a particular prosthetic application, rather than simply copying existing prosthetic joints with new materials.

It is another object of some embodiments of the invention to provide an artificial joint with an improved ball and cup configuration. The invented prosthetic hip joint is made from very few components in a simple design, thus contributing to the ease of manufacturability and reliability. The ball and cup are designed to maximize articulation within the normal range of movement for a human joint while providing exceptional wear resistance and useful life.

It is another object of some embodiments of the invention to provide a cup and ball type prosthetic joint that can be used without a separate shell. Some embodiments of the invention provide an acetabular cup that may be fixed to a patient's bone without the need for a separate shell.

It is another object of some embodiments of the invention to provide a prosthetic joint, which combines the use of a polycrystalline diamond compact bearing surface with a counter-bearing surface of another material. In some embodiments of the invention, the counter-bearing surface may be any of a wide variety of materials, including prior art UHMWPE, or even the patient's natural cartilage in the case of a hemiarthroplasty procedure.

It is another object of some embodiments of the invention to provide a modular prosthetic joint assembly with a superhard bearing surface. Some embodiments of the invention provide modular prosthetic joint components which can be selected and assembled at the time of surgery to provide a prosthetic joint system with dimensions and angular orientation closely approximating those of the patient's natural joint. An appropriate superhard bearing surface may be provided, such as a polycrystalline diamond compact.

Its is another object of some embodiments of the invention to provide a prosthetic bearing surface useful in hemiarthroplasty procedures. The nature of the preferred prosthetic joint articulation surface bearing material, polycrystalline diamond, is such that it can be used as a bearing material that can articulate against natural cartilage, permitting hemiarthroplasty.

It is another object of some embodiments of the invention to provide a replacement liner or cover for a natural joint. In some embodiments of the invention, a femoral head or other natural joint surface may be resurfaced or relined with the invention in order to achieve bone conservation.

It is another object of some embodiments of the invention to provide polycrystalline diamond compacts useful as bearing surfaces with improved fastening strength between the diamond table and the substrate of the polycrystalline diamond compact. In various embodiments of the invention, topographical features are provided on the substrate in order to achieve this improved fastening strength.

It is an object of some embodiments of the invention to provide substrate configuration that permit the manufacture of spherical, partially spherical and arcuate polycrystalline diamond compacts. Various substrate configurations are disclosed which achieve this object.

It is an object of some embodiments of the invention to provide non-planar polycrystalline diamond compact bearing surfaces. Various embodiments of the invention provide novel bearing surfaces that are non-planar and preferably are manufactured as polycrystalline diamond compacts.

It is an object of some embodiments of the invention to provide a method for manufacturing non-planar polycrystalline diamond compact bearing surfaces. Various methods are disclosed for materials preparation and polycrystalline diamond compact manufacturing that will produce non-planar polycrystalline diamond compact bearing surfaces, including but not limited to concave and convex spherical bearing surfaces.

It is an object of some embodiments of the invention to provide methods for rough shaping of non-planar polycrystalline diamond compact bearing surfaces. Novel machining techniques are disclosed which accomplish such shaping.

It is an object of some embodiments of the invention to provide methods for finish polishing of non-planar polycrystalline diamond compact bearing surfaces. Novel polishing techniques are disclosed which permit polishing of polycrystalline diamond compact bearing surface to be highly polished to a low coefficient of friction.

It is another object of some embodiments of the invention to provide a joint with enhanced wettability. Use of a diamond bearing surface achieves this object.

The objects, features and advantages of the inventions mentioned above are exemplary and illustrative only so that the reader may begin to perceive advantages to be accrued by use of the invention alone or in combination with other technology. Additional objects, features and advantages of the invention will become apparent to persons of ordinary skill in the art upon reading the specification and claims and viewing the drawings.

BRIEF DESCRIPTION OF THE DRAWINGS

FIGS. 2O, 2S, 2T and 2U depict the use of offsets to achieve adjustable geometry of prosthetic hip joints of the invention.

FIG. 2AA depicts a thumb or finger prosthesis of the invention.

FIGS. 2AB and 2AC depict a total prosthetic knee joint of the invention.

FIGS. 2AD and 2AE depict a unicompartnental prosthetic knee joint of the invention.

FIGS. 2AF and 2AG depict a sliding bearing rotating platform prosthetic knee joint of the invention.

FIG. 4BB depicts a sintered polycrystalline diamond compact in which there is a continuous gradient transition from substrate metal through the diamond table.

FIGS. 8 and 8A depict a precompaction assembly, which may be used to reduce free space in diamond feedstock prior to sintering.

FIG. 9 depicts EDM roughing of a convex spherical part.

FIG. 10 depicts EDM roughing of a concave spherical part.

FIG. 11 depicts grinding and polishing of a convex spherical part.

FIG. 12. depicts grinding and polishing of a concave spherical part.

DETAILED DESCRIPTION OF THE PREFERRED EMBODIMENTS

Reference will now be made to the drawings in which the various elements of the present invention will be discussed using a prosthetic hip joint as an example. It will be appreciated that the structures and principles of the invention can be applied not only to biomedical articulation surfaces, but also to other types of articulation surfaces, to the manufacture, shaping and finishing of superhard materials and superhard components, and to the manufacture, shaping and finishing of devices using superhard articulation surfaces and superhard components. Persons skilled in the design of prosthetic joints and other bearing surfaces will understand the application of the various embodiments of the invention and their principles to joints, bearing surfaces and devices other than those exemplified herein.

A. An Example of the Prior Art

Figures 1, 2A:
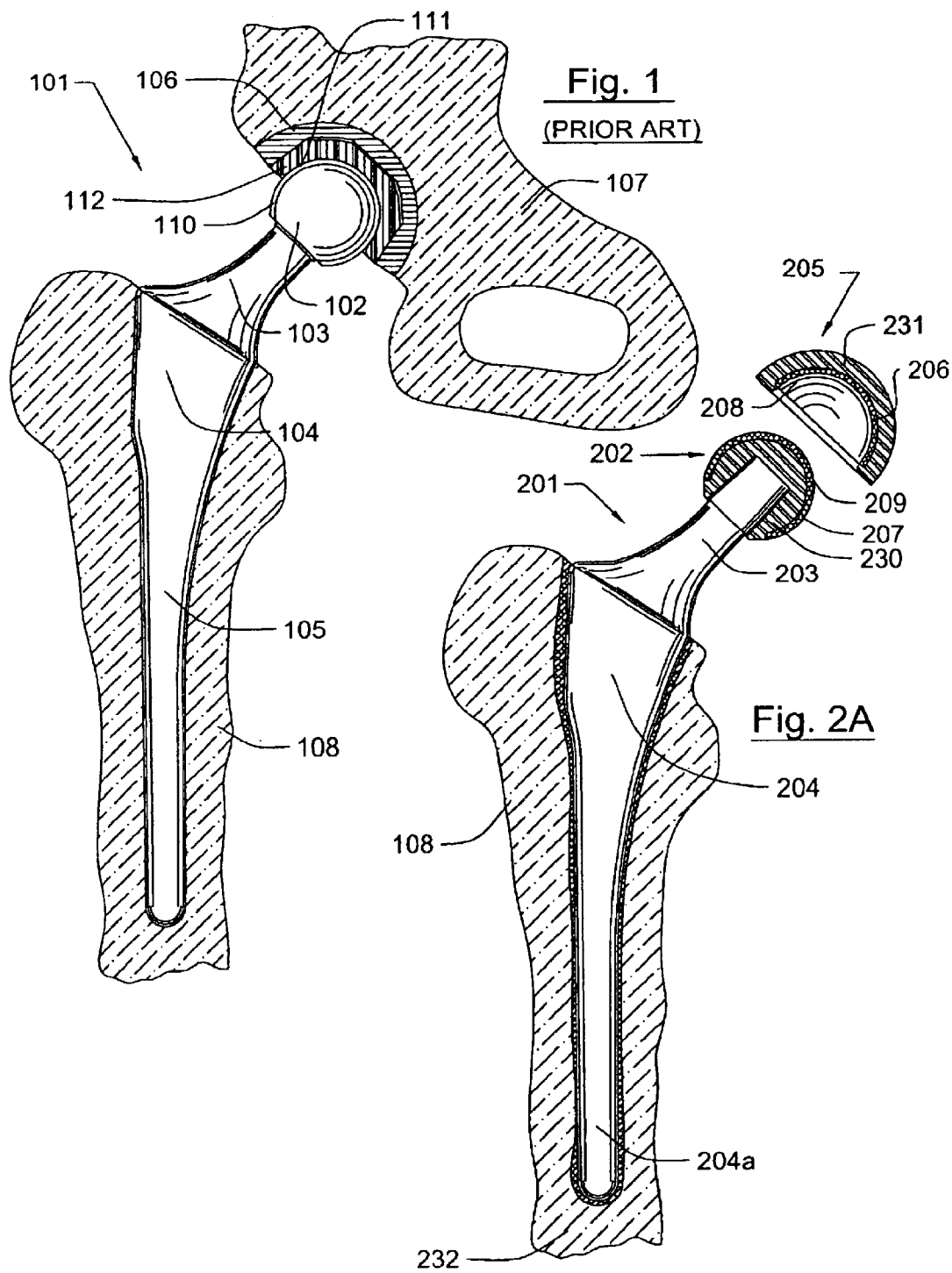
FIG. 1 depicts a side cross-sectional view of a prior art prosthetic hip joint such as those commonly mounted in the hip of a human.
FIG. 2A depicts an enlarged side cross-sectional view of one embodiment of a prosthetic hip joint made in accordance with the principles of the present invention.

Referring to FIG. 1, a prior art prosthetic hip joint 101 is shown after installation in a patient. The prosthetic hip joint 101 includes a metal or ceramic ball 102, which is connected by a neck 103 to a body 104 and a stem 105. The stem 105 may be held in place in the femur 108 by a variety of methods, including use of cementing agents, an interference press fit, a threaded mechanism, and biological fixation.

A cup-shaped socket 106 is anchored in the pelvis 107 by any of a variety of known techniques, such as cementing, press fitting, use of screws, use of a textured, knurled or threaded exterior, use of a biological fixation mechanism, or by a combination of biological and mechanical fixation. The ball 102 is positioned so that its spherical convex load bearing surface 110 is adjacent the concave load-bearing surface 112 of the socket 106 so as to permit joint rotation, simulating the movement of a natural hip joint. As shown in FIG. 1, a high molecular weight polymer 111a is disposed within the socket 106 so as to decrease the friction between the ball 102 and the socket 106, thereby increasing the life of the joint 101. The outer surface of the ball 102 is generally referred to as the load-bearing area or surface of the ball, as this area interfaces with the load-bearing surface 112 of the socket 106 and allows the joint to articulate and rotate.

The disadvantages of such a prosthetic joint are described in detail above.

B. The Invented Bearing Articulation Surfaces and Related Structures

FIG. 2A illustrates one embodiment of the present invention. FIG. 2A shows a prosthetic joint 201 and its various constituent components. The joint 201 shown includes a ball 202 or femoral head, a neck 203, a fragmented view of the body 204 and stem 204a and a socket 205 or acetabular cup. The stem 204 is placed in a receptacle formed in the femur 108 and is preferably attached to the femur 108 by use of cement 232 or another appropriate fixation system. A locking ring such as that depicted in FIG. 2I may be used to retain the ball within the socket.

In accordance with the principles of the present invention, the socket 205 and/or the ball 202 may be made of durable metal. A list of appropriate materials is disclosed below. The preferred ball and socket combination, as depicted, includes a truncated ball 202 that is a polycrystalline diamond compact. The polycrystalline diamond compact has a quantity or table of polycrystalline diamond 207 sintered to a substrate material 230. The socket 205 similarly is a polycrystalline diamond compact, having a substrate material 231 on which is sintered a table of polycrystalline diamond 206. In this combination, the bearing or articulation surface 209 of the ball and the bearing or articulation surface 208 of the socket are spherical in shape and can move, roll and slide with respect to each other in all three dimensions within the confines of the cup surface. It is preferred that the cup have a hemispherical load bearing and articulation surface (about 180°) for maximum support, strength and mobility in the prosthetic joint.

As discussed in greater detail below, cup and ball will preferably use (polycrystalline diamond compacts in order to form articulation surfaces. In a polycrystalline diamond compact, the diamond tables 206 and 207 are chemically bonded and mechanically fixed to their respective substrates 230 and 231 in a manufacturing process that preferably uses a combination of high pressure and high temperature to form the sintered polycrystalline diamond (see, e.g., FIGS. 4A–D and related text). The chemical bonds between the diamond table and the substrate are established during the sintering process by combinations of unsatisfied sp3 carbon bonds with unsatisfied substrate metal bonds. The mechanical fixation is a result of shape of the substrate and diamond table and differences in the physical properties of the substrate and the diamond table as well as the gradient interface between the substrate and the diamond table. The resulting sintered polycrystalline diamond compact forms a prosthetic joint that is extremely hard, low fiction, durable, impact-resistant, biocompatible and long lasting.

The diamond tables 206 and 207 are preferably polished to a very smooth and glass-like finish to achieve a very low coefficient of friction. As the diamond is very hard and the coefficient of friction is very low, the wear between the diamond contact surfaces is almost negligible, resulting in a very long lasting joint. Also due to the hardness, fracture toughness and low coefficient of friction that can be achieved with polished polycrystalline diamond compacts, the joint is able to withstand substantial impact shock without damage. Polycrystalline diamond also provides the advantage of high surface energy so that it is very wettable and lubricates well for low wear rates and long life.

While FIG. 2A depicts a prosthetic hip joint that uses both a polycrystalline diamond compact femoral head and a polycrystalline diamond compact acetabular cup, it is possible to use the invented structures disclosed herein in other configurations. In some joints, any of the following materials could be considered for forming a bearing surface: polycrystalline diamond, monocrystal diamond, natural diamond, diamond created by physical vapor deposition, diamond created by chemical vapor deposition, diamond like carbon, carbonado, cubic boron nitride, hexagonal boron nitride, or a combination of these, polymers such as ultra high molecular weight polyethylene (UHMWPE), cross-linked UHMWPE, poly ether ether ketone, polymer composites, polyurethane, cobalt, chromium, titanium, vanadium, stainless steel, niobium, aluminum, nickel, hafnium, silicon, tungsten, molybdenum, aluminum, zirconium, nitinol, cobalt chrome, cobalt chrome molybdenum, cobalt chrome tungsten, tungsten carbide, titanium carbide, tantalum carbide, zirconium carbide, hafnium carbide, Ti6/4, silicon carbide, chrome carbide, vanadium carbide, yttria stabilized zirconia, magnesia stabilized zirconia, zirconia toughened alumina, titanium molybdenum hafnium, alloys including one or more of the above metals, ceramics, quartz, garnet, sapphire, combinations of these materials, combinations of these and other materials, and other materials may also be used for a bearing surface.

The present preferred material for manufacturing both the ball and cup wear surfaces, however, is a sintered polycrystalline diamond compact due to its superior performance. Diamond has the greatest hardness and the lowest coefficient of friction of any currently known material. The preferred sintered polycrystalline diamond compacts are chemically and biologically inert, are impervious to all solvents, and have the highest thermal conductivity at room temperature of any known material. It is also possible, however, to make an articulating joint in which either one or both bearing surfaces are made from materials selected from the table above, but neither bearing material is diamond.

Figure 2B:
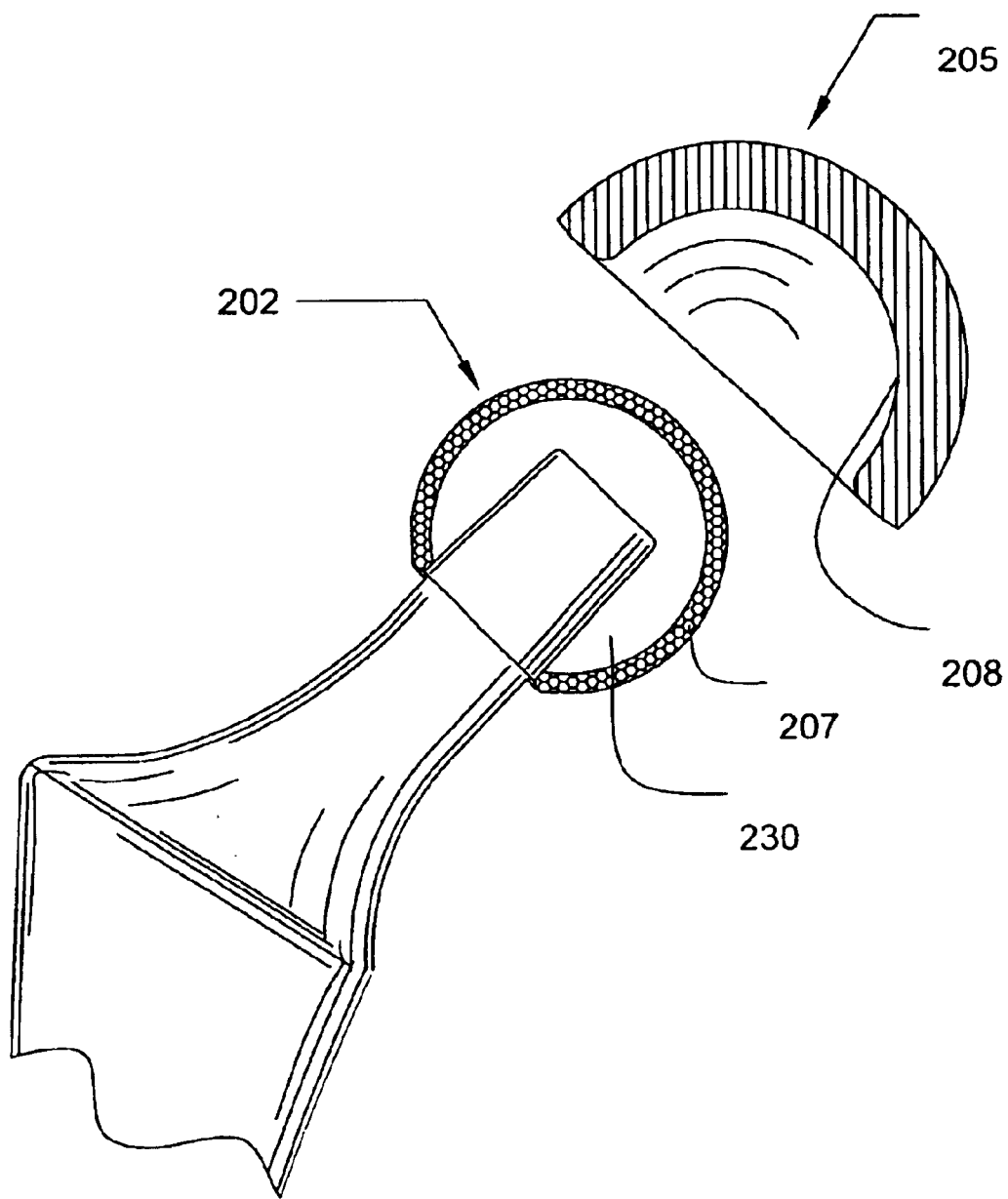
FIGS. 2B–G depict various embodiments of prosthetic hip joints of the invention.

FIG. 2B depicts a prosthetic hip joint of similar configuration to that depicted in FIG. 2 with some important differences. The femoral head 202 is a polycrystalline diamond compact that has a diamond table 207 and a substrate 230 to which it is affixed both mechanically and by chemical bonds. The cup 205, however, is depicted as an appropriate counter bearing material without a diamond table. The material for the cup 205 could be any of those mentioned above as appropriate counter bearing material, a superhard material, a corrosion-resistant metal, ceramic or a polymer material. The load-bearing surface 208, however, must be biocompatible, durable and have a low coefficient of friction.

Figure 2C:
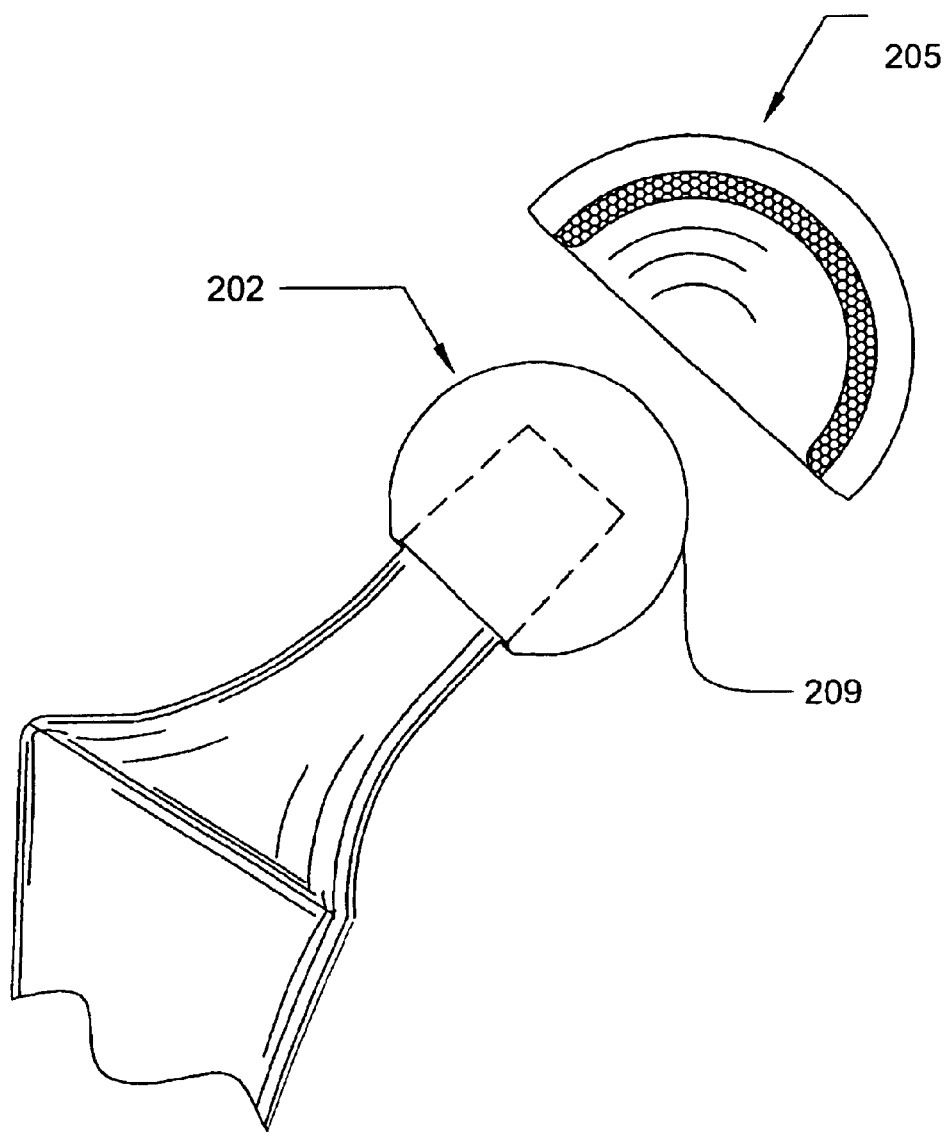

FIG. 2C depicts an alternative embodiment of the invention in which the cup 205 is a polycrystal we diamond compact as described above. The ball 202, however, is not a polycrystalline diamond compact and does not include a diamond table. The ball 202 could be of any counter bearing material previously referred to, but should have a bearing surface 209 that is durable, is biocompatible for prosthetic applications, and has a low coefficient of friction.

Figure 2D:
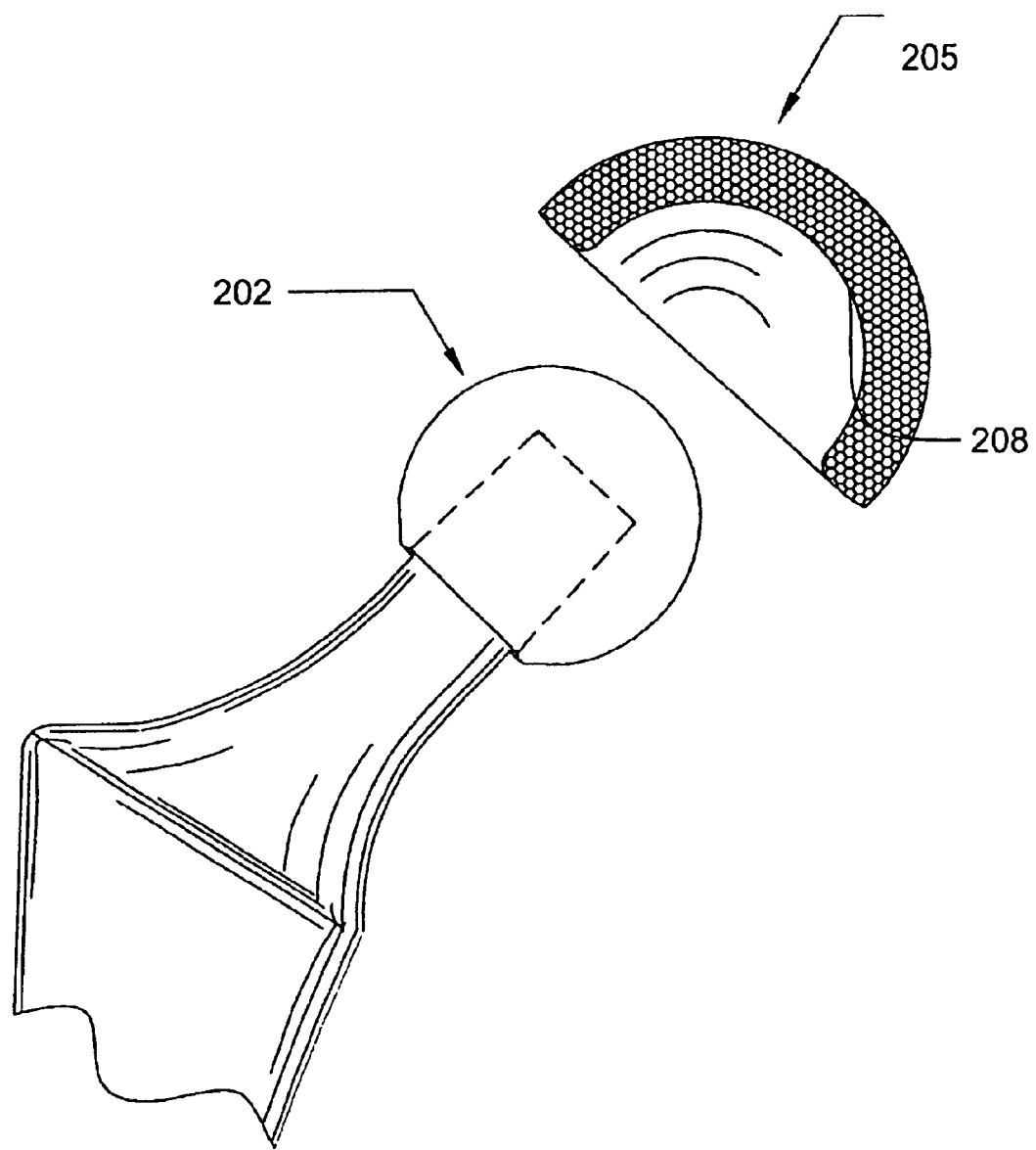

FIG. 2D depicts an alternative embodiment of the invention in which the ball 202 is an appropriate counter bearing material other than diamond, and the cup 205 is of solid polycrystalline diamond without a substrate. This provides the appropriate load-bearing surface 208 but avoids concerns about the body's acceptance of or reaction with a substrate material in the cup.

Figure 2E:
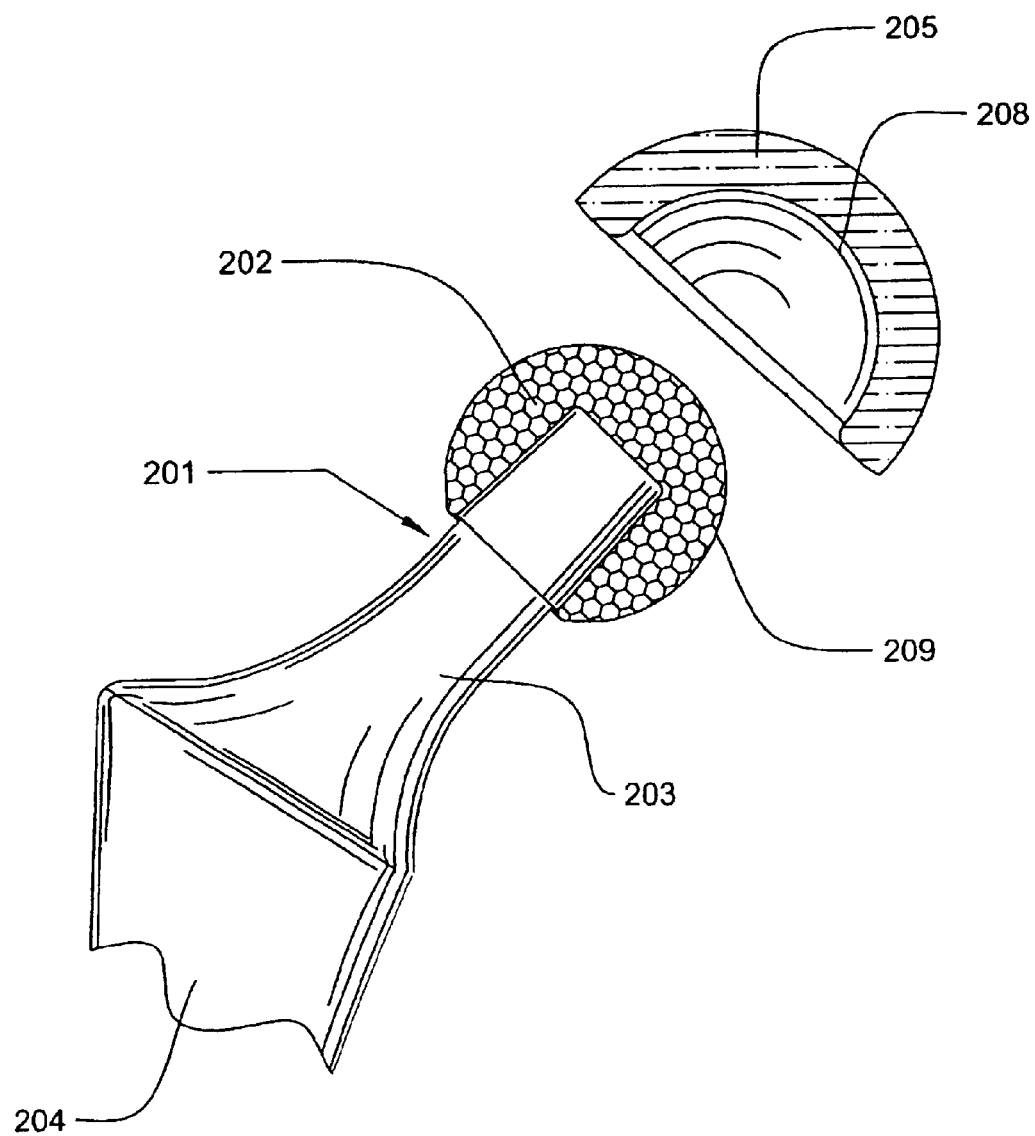

FIG. 2E depicts an alternative embodiment of the invention in which the cup 205 may be of any appropriate counter bearing material, such as those mentioned previously, and the ball 202 is solid polycrystalline diamond.

Figure 2F:
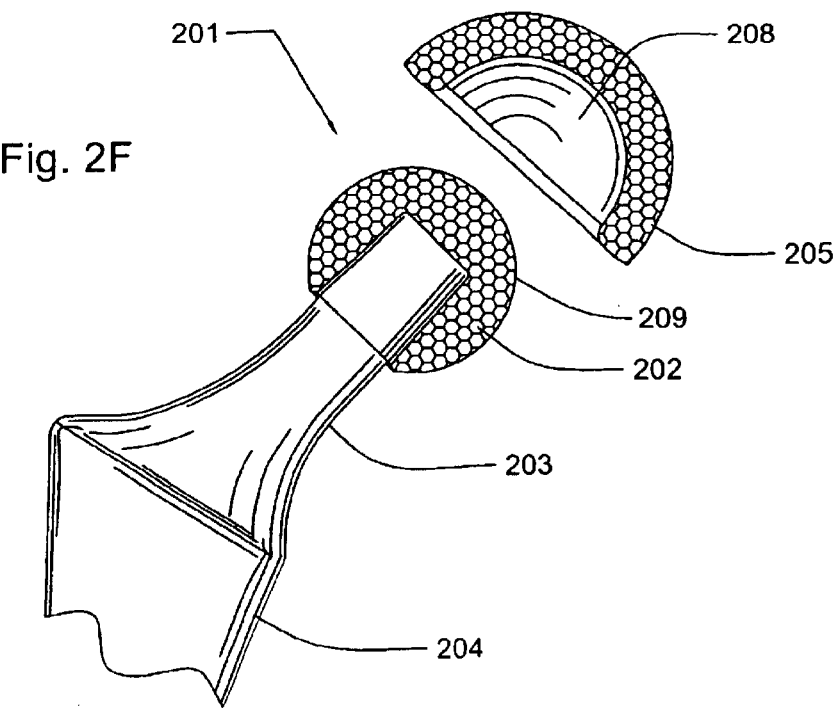

FIG. 2F depicts an alternative embodiment of the invention in which both the ball 202 and the cup 205 are made from solid polycrystalline diamond. This will completely eliminate any concern about the body's acceptance of substrate metals, as none will be present. Solid polycrystalline diamond components may be manufactured according to the methods presented below.

Figure 2G:
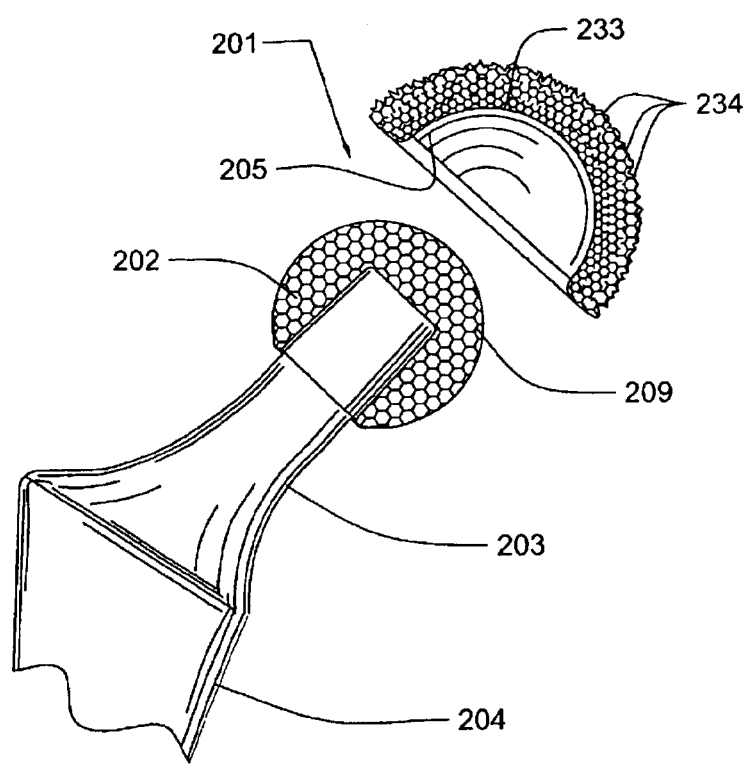

FIG. 2G depicts an alternative embodiment of the invention in which the cup 205 is made from a continuous or solid polycrystalline diamond (as opposed to a diamond table affixed to a substrate) and has been formed with a porous region 233 including may small pores, cavities, openings or fenestrations 234. The pores 234 permit the ingrowth of bone into the cup 205 so that osseointegration may be used as the fixation mechanism for the cup, or osseointegration may be used in conjunction with another fixation mechanism such as press fitting. The pores 234 may be formed in the cup by adding a quantity of beads or microspheres to the diamond feedstock of the outer region of the cup prior to sintering. For optimal bone ingrowth, the pores will be sized in the range of 125 to 300 microns. Generally it is expected that the pores will be in the range of about 50 to 500 microns in diameter. Beads or microspheres that may be used to form the pores include hexagonal boron nitride, cubic boron nitride, cobalt chrome, nickel and others. The beads or microspheres may be chemically or mechanically removed from the polycrystalline diamond compact matrix, leaving a porous surface suitable for biological fixation. Depending on the beads or microspheres used to form pores in the cup, or other materials used in joint formation, it may be necessary to chemically leach toxic materials out of the cup or prosthetic component before it can be implanted in a patient. Porous substrates may be formed similarly. The ball 202 as depicted is also of solid polycrystalline diamond, but no pores are provided in the ball, as it will not be necessary to achieve bone ingrowth into the ball. In alternative embodiments of the invention, any polycrystalline diamond compact may be created with pores useful for biological fixation.

Figure 2H:
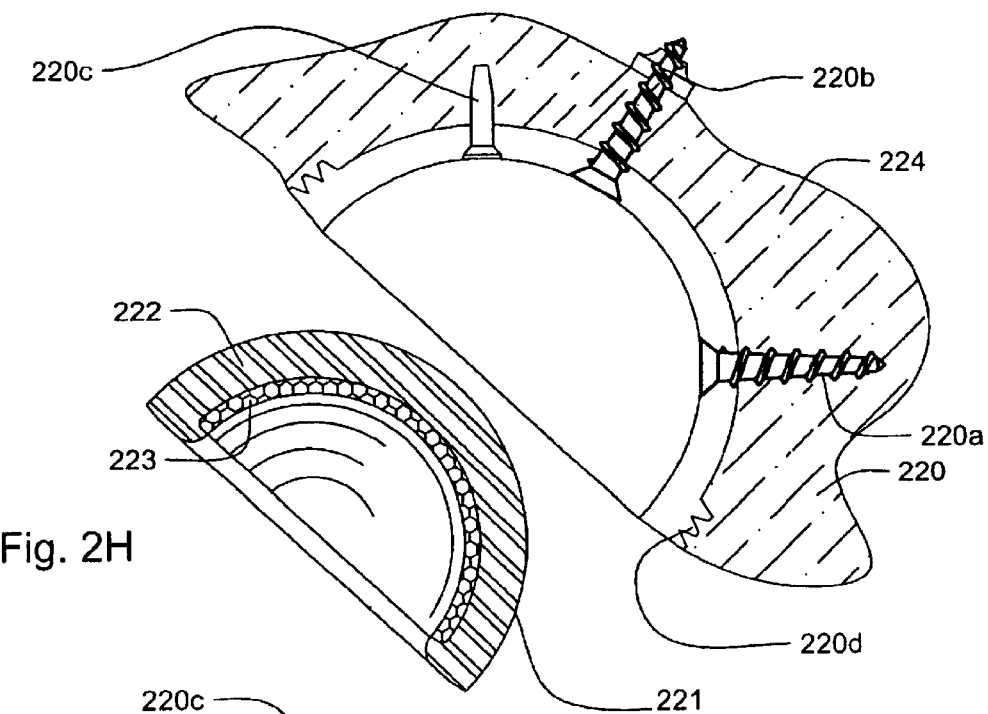
FIGS. 2H–2J depict various acetabular cups of the invention.

FIG. 2H depicts an acetabular cup assembly of the invention. The assembly includes a shell 220 and a cup 221. The cup 221 is preferably a sintered polycrystalline diamond compact having a substrate 222 and a diamond layer 223. The shell 220 may be affixed to patient bone 224 by a variety of attachment mechanisms, such as screws 220a, a nut and bolt combination 220b, pins 220c or threads 220d on the shell 220. Adhesion and press fitting may also be used to affix the shell to bone. The shell may optionally include a textured bone-mating surface or appropriate coating (such as hydroxyl apatite) to encourage grown growth, as discussed elsewhere herein. The acetabular cup may be attached to the shell according to a desired angular orientation and offset during surgery in order to approximate natural joint geometry, such as shown in FIGS. 2H and 2I, or by another means.

Figure 2I:
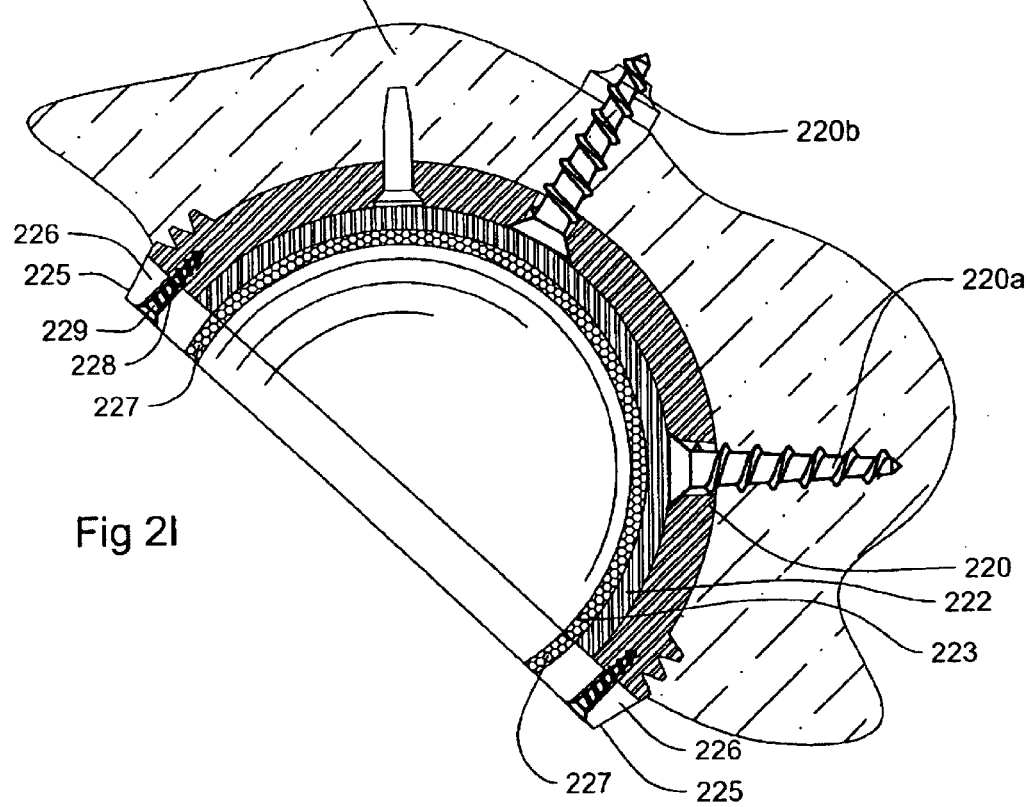

FIG. 2I depicts a restrained acetabular cup assembly of the invention. The assembly may include the cup, shell and attachment mechanisms of FIG. 2H. In addition, the assembly includes a retaining ring 225. The restraining ring 225 is preferably an annular ring of polycrystalline diamond compact having a substrate layer 226 and a diamond table 227. The retaining ring 225 may include a number of bores 228 through it so that fasteners 229 may be used to affix the ring 225 to the shell 220. The ring 225 would hold the cup 221 in the shell and would prevent dislocation of a ball from the cup.

Figure 2J:
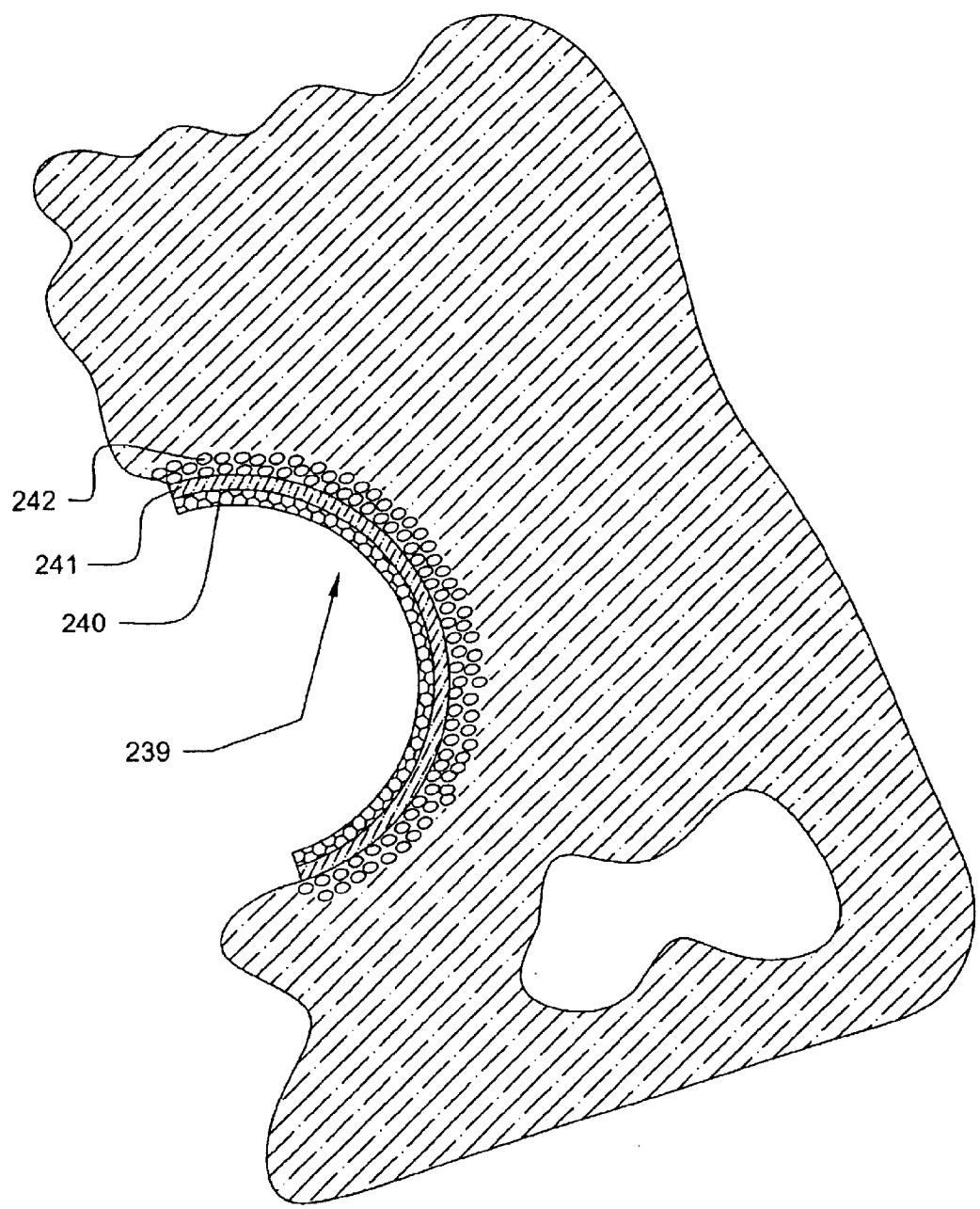

FIG. 2J depicts another acetabular cup assembly of the invention. The assembly includes a polycrystalline diamond compact cup 239 that includes a diamond table 240 sintered to a substrate 241. A specially configured bone-mating surface 242 is provided on the hipbone side of the cup. The bone-mating surface may include a variety of structures in order to aid in securing the cup 239 to a hipbone. The bone mating surface 242 may include small pores to encourage bone growth thereto and therein. Such small pores may be created by a titanium plasma spray or diffusion bonding of beads or mesh, chemical leaching, laser machining or other methods. The bone-mating surface 242 may also incorporate an apatite coating such as hydroxyl apatite to encourage bone growth. Hydroxyl apatite is applied in a thin coating with a high degree of crystalinity. The body will lay down protein structures next to the apatite to begin bone growth. The bone-mating surface 242 may also include small beads or other surface roughness such as ribbing to which bone will grow. Surface roughness that allows bone growth next to it can achieve osseointegration. Alternatively, the bone mating surface 242 may be a porous metal mesh as is known in the medical art to promote bone growth. Appropriate metal meshes can be layers of titanium screen diffusion bonded together and then diffusion bonded to the metal of the prosthetic cup.

In such a configuration, a press fit, a wedge fit or another mechanical or friction fit may be used to affix the prosthetic joint to a human bone at the time of surgery. Press fitting is achieved by creating a receptacle in the bone slightly smaller than the prosthetic implant to be used. Then the implant is forcefully inserted into the receptacle and is frictionally held there for immediate fixation. Alternatively, fixation of the prosthetic joint to bone can be achieved by use of bolts, screws, rivets or pins, similar to those already discussed. The prosthetic joint can also be attached to bone by use of an appropriate adhesive or cement, such as polymethyl methacrylate. Long-term fixation is provided or enhanced, however, by bone ingrowth into the bone mating surface 242. Bone ingrowth will minimize micromovement of the joint during use and will provide a more durable system for the patient. When apatite coatings are used, the bone will be encouraged to anchor directly to the implant surface.

Figure 2K:
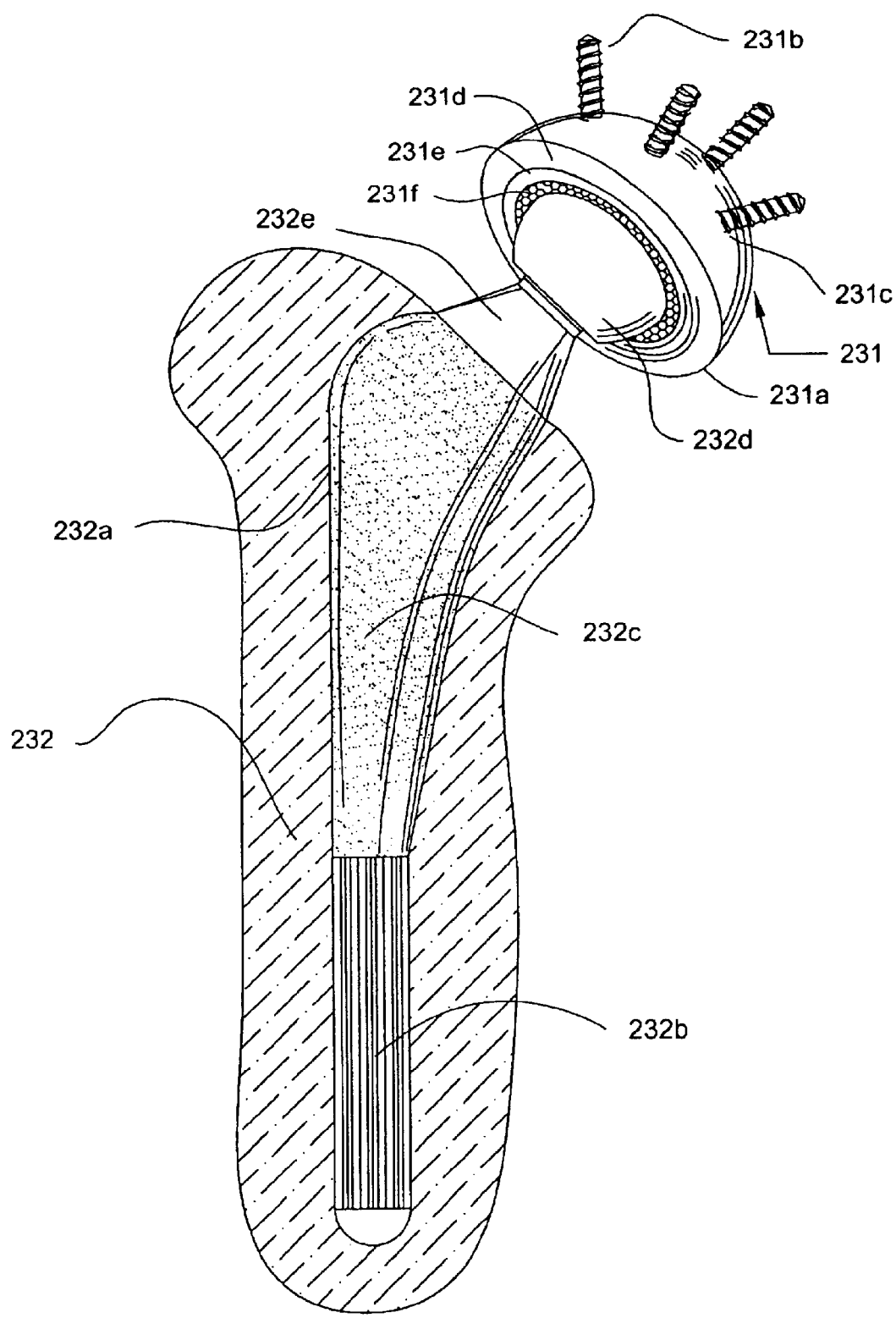
FIG. 2K depicts a total prosthetic hip joint of the invention.

FIG. 2K depicts a prosthetic hip joint of the invention. It includes a cup assembly 231 and a ball assembly 232. The ball assembly 232 includes stem 232a which may include a grooved or ridged portion 232b and which may include a textured or coated portion 232c. The ball assembly 232 also includes a ball 232d attached to the stem 232a by a neck 232e. The ball preferably provides a load bearing and articulation surface that is at least partially comprised of polycrystalline diamond, and as desired the ball can be solid polycrystalline diamond. The cup assembly 231 includes a shell 231a, which may be attached to bone by mechanical fasteners 231b, by adhesion or by press fitting. The shell 231a may include a textured surface or bone growth-enhancing coating 231c on its exterior. An acetabular cup 231d is mounted in the shell. The acetabular cup 231d as depicted includes a substrate 231e and a polycrystalline diamond load bearing and articulation surface 231f for providing articulation with respect to the ball 232d.

Figure 2L:
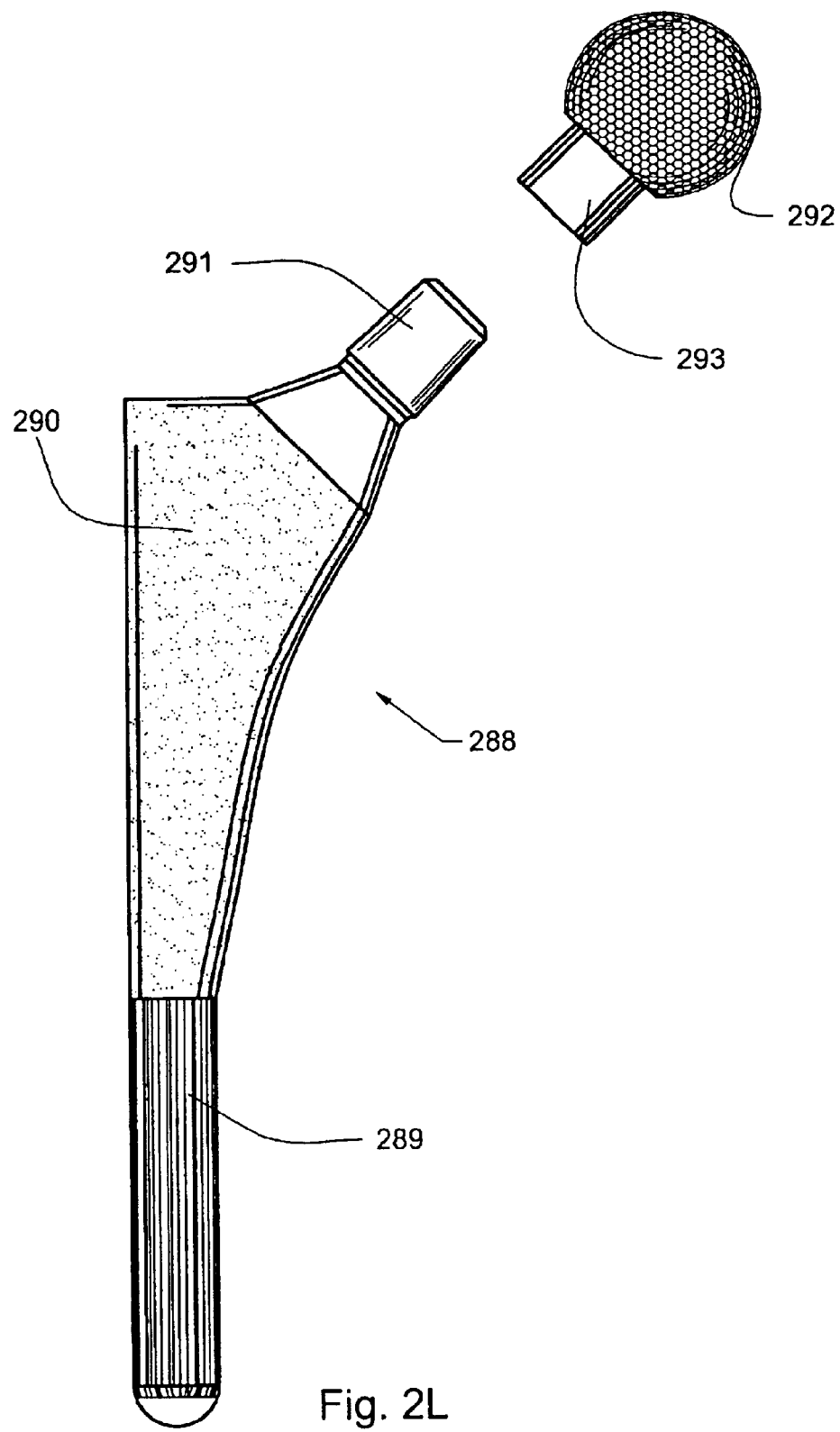
FIGS. 2L–2N depict femoral components of prosthetic hip joints of the invention.

Referring to FIG. 2L, a femoral portion of a prosthetic hip joint of the invention is depicted. It includes an integral stem and body 288, the stem portion of which may include ridges or grooves 289 for bone fixation, and the body of which may include a bone mating surface 290. The bone mating surface 290 may be a region of microtexture or porous surface, a region of ribs, a metal mesh, shoulders or other appropriate texture, a coating such as hydroxyl apatite or other apatite coating, or any other surface or feature that will encourage bone growth or bone fixation. The microtexture, porous surface, ribs or shoulders are intended to facilitate frictional engagement with human bone and to permit bone to grow adjacent thereto. In the case of a porous surface, it is intended that there may be osseointegration between the bone and the surface in order to secure the implant to the bone. A porous surface may be achieved by placing small metal beads, balls or microspheres (such as metal balls of commercially pure titanium or a titanium alloy containing 90% titanium, 6% aluminum and 4% vanadium) on the exterior of the prosthetic joint The stem and body device 288 includes a mounting pole 291 for mounting a femoral head 292 thereto. The femoral head 292 is a polycrystalline diamond compact that includes a substrate and a polycrystalline diamond bearing surface. A substrate protrusion 293 is present on the femoral head 292 in order to facilitate mounting of the femoral head to the mounting pole, such as by welding or mechanical fixation.

Figure 2M:
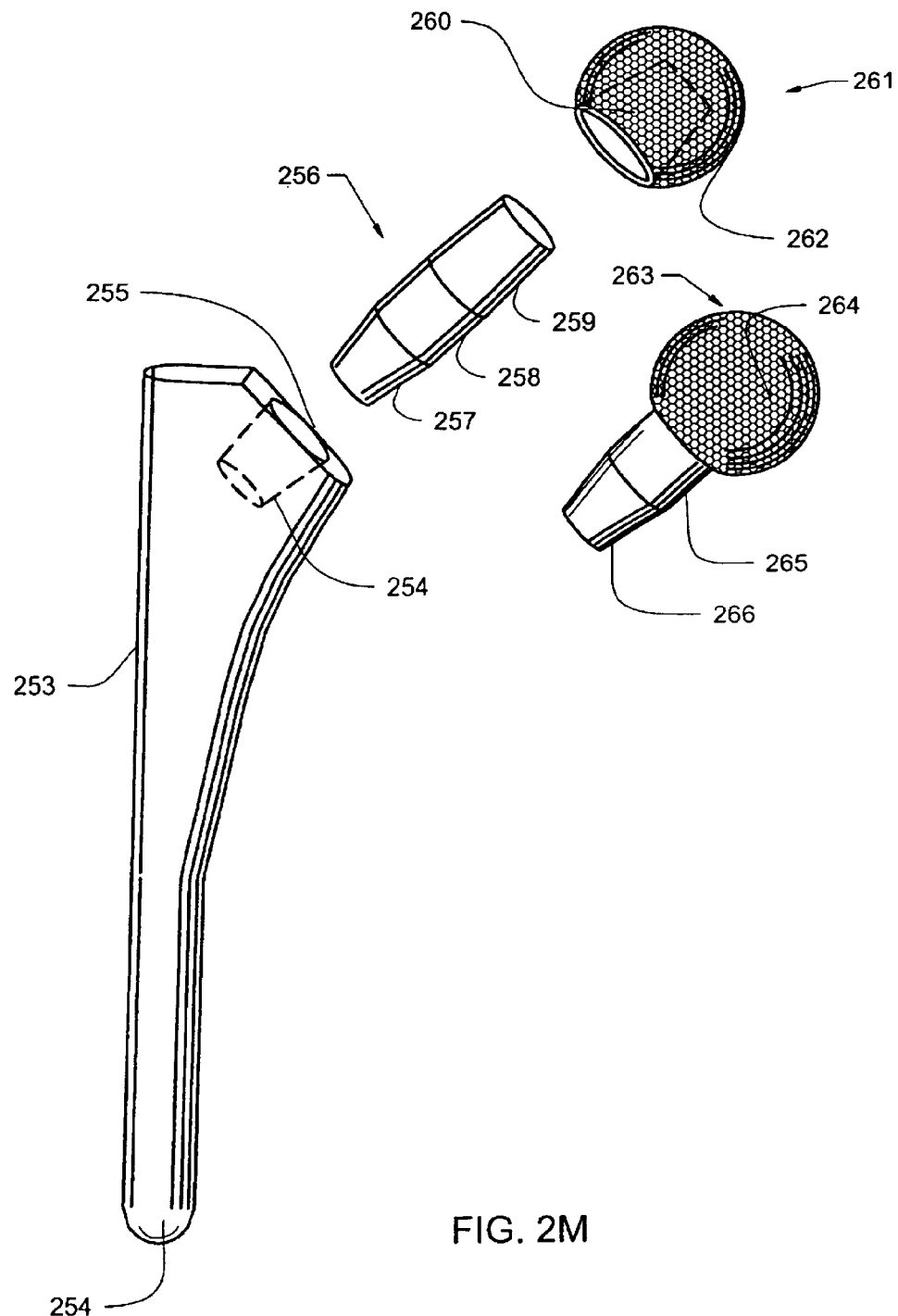

Referring to FIG. 2M, an example of an embodiment of the invention employed in a modular prosthetic hip assembly is depicted. The assembly includes an elongate stem 253 that has an elongate and rounded distal end 254 for insertion into an intermedullary channel of a femur. At the proximal end of the stem 253, an enlarged body 254 is found. A female receptacle, seat or recess 255 is located near the proximal end of the stem on the enlarged body. The receptacle is oriented in a manner divergent from the longidutinal axis of the stem. The receptacle 255 may be configured for locking other portions of a prosthetic joint thereto. As depicted, the receptacle has an oval taper in order to establish a firm and permanent taper press fit with the neck 256 of the joint. Alternatively, the receptacle may be threaded or have another shape to permit fixation of another joint component thereto. The head may be fixed to the neck by a separate self-locking taper or by another appropriate means such as welding (including inertia welding).

For insertion into the receptacle 255, a neck 256 is provided. The neck 256 has a proximal portion 257 for stem fixation, a mid body portion 258, and a distal portion 259 for femoral head fixation. The proximal portion 257 as depicted has a male oval taper for press fitting with the receptacle 255 of the stem 253. If the receptacle 255 had another fixation mechanism, such as threads, then the proximal portion 257 of the neck 256 would include a complementary fixation structure. The distal portion 259 of the neck 256 as depicted is frusto-conical in shape in order to be press fit into an appropriate receptacle, seat or recess 260 in a femoral head 261. The femoral head 261 is preferably a polycrystalline diamond compact. The neck mid body 258 may be cylindrically shaped or otherwise shaped and may be provided in a variety of lengths. The femoral head 261 includes a bearing surface 262 that is polycrystalline diamond, according to the principles of the invention.

The assembly depicted, including the stem, stem receptacle, neck, and femoral head is useful for causing a universal prosthetic joint stem and femoral head to fit in a wide variety of patients. This is accomplished by providing a variety of necks of different lengths and angular offsets. Use of a neck of an appropriate length and angular offset allows the femoral head to be oriented in a desired position with respect to the stem in order approximate positioning of the natural femoral head. Ordinarily, the angular offset of the neck proximal end or male taper with respect to the longitudinal axis of the neck mid portion will be varied in order to provide a product line that will fit many patients. As the neck portion of the prosthetic joint includes a slight angular offset, it actually achieves two different geometries in the prosthetic joint. For any angular geometry that may be achieved by the prosthetic joint, if the neck is removed and reinstalled 180 degrees out of phase, a mirror image geometry is then achieved.

In FIG. 2M, an alternative neck and femoral head assembly 263 is depicted. In this embodiment of the invention, a polycrystalline diamond compact prosthetic femoral head 264 is provided with a fixed neck 265 protruding from it. The neck 265 includes a male attachment element 266 that as depicted has an oval taper for press fitting with the receptacle 255 of the stem 253. Unitary head and neck assemblies 263 may be supplied by the prosthetic joint manufacturer in a variety of femoral head diameters, a variety of neck lengths, and a variety of neck angular offsets in order to permit surgeons to achieve a good dimensional and geometric fit in a patient during surgery. Taper fitting of various parts of a prosthetic joint to each other may be achieved by a variety of tapers, such as oval tapers, round tapers, and others.

Figure 2N:
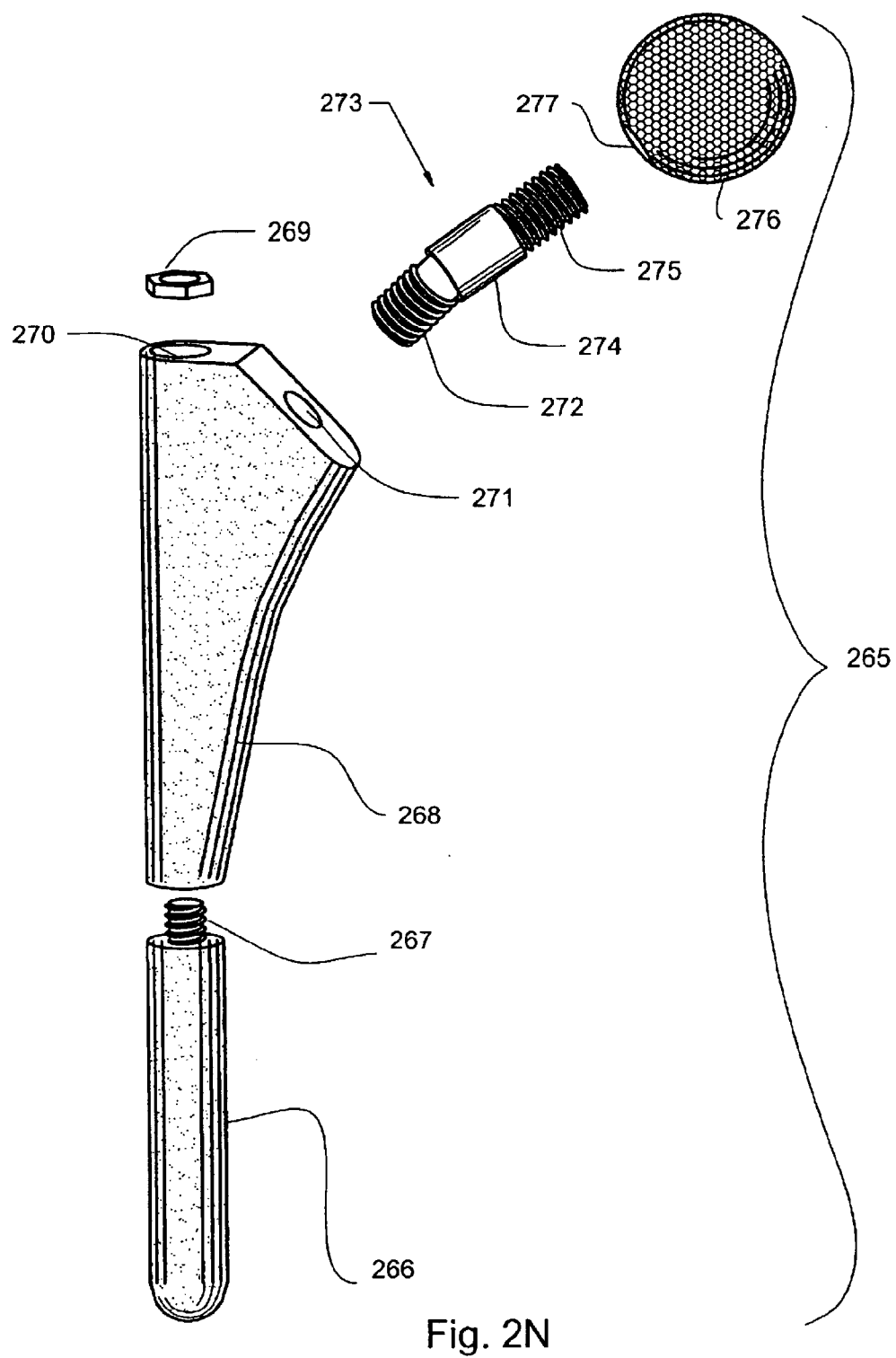

Referring to FIG. 2N, an alternative embodiment of the invention is depicted. In this embodiment of the invention, a prosthetic hip joint assembly 265 is provided. The assembly 265 includes a stem 266 for insertion into an intermedullary canal of a femur. The stem 266 includes threads 267 on its proximal end for fixation to a body 268 portion. The threads 267 of the stem 266 may accommodate a nut 269 inserted through a receptacle 270 of the body 268 for fixation of the stem 266 thereto. The body 268 includes a second receptacle 271 with an axis oriented at a divergent angle with the longitudinal axis of the body. The second receptacle 271 includes threads in its interior for receiving a threaded body attachment end 272 of a neck 273. The body attachment end 272 of the neck 273 may be oriented at an angular offset with respect to the mid portion 274 of the neck. The neck 273 also includes a femoral head attachment end 275 for attaching a femoral head 276 thereto, such as by use of a threaded receptacle 277 on the femoral head. The preferred femoral head as depicted is a polycrystalline diamond compact. The stem 266 and the body 268 may include an appropriate bone mating surface, such as hydroxyl apatite, a porous surface, a high friction surface, wire mesh, or other features to assist in anchoring the prosthetic joint in bone.

FIG. 2O depicts a top view of anterior and posterior offset that can be achieved using an oval taper with the invention. A receptacle 278a in a first prosthetic joint component 278b is provided. The receptacle 278a has an oval taper of desired configuration. A second prosthetic joint component 278c is provided having a protrusion 278d that has an oval taper corresponding to that of the receptacle 278a. The second prosthetic joint component 278c may be attached to the first prosthetic joint component 278b by use of the oval tapers. A neutral anterior/posterior offset may be achieved by use of the installation configuration indicated at 278e. Rotation of the second prosthetic joint component about the longitudinal axis of its tapered protrusion 278d can be used to achieve anterior offset 278f of posterior offset 278g. This can be accomplished because the tapered protrusion 278d of the second joint component protrudes from a neck 278h. The tapered protrusion 278d and the neck 278h each have a longitudinal axis. The tapered protrusion 278d may be located on the neck 278h so that the longitudinal axes of the tapered protrusion 278d and the neck 278h are at an angle other than 180 degrees. When the tapered protrusion is installed in a receptacle, it can be installed so that the angular orientation of the tapered protrusion with respect to the neck provides an anterior or posterior offset as desired.

FIGS. 2S, 2T and 2U depict a side view of vertical offset that can be achieved using an oval taper in the invention. A first prosthetic joint component 279a and a second prosthetic joint component 279b are provided. The first prosthetic joint component 279a has a tapered receptacle 279c as already described. The receptacle has a longitudinal axis. The second prosthetic joint component 279b includes a tapered protrusion 279d on a neck 279e. Each of the tapered protrusion 279d and the neck 279e have a longitudinal axis. The second prosthetic joint component 279b may be installed in the receptacle 279c of the first prosthetic joint component 279a so that the longitudinal axis of the receptacle 279c, the tapered protrusion 279d and the neck 279e coincide. This is considered the neutral position with no positive or negative vertical offset, as depicted in FIG. 2S. FIG. 2T depicts the second prosthetic joint component 279b installed in the receptacle 279c so that there is an angular offset between the longitudinal axis of the neck 279e with respect to the longitudinal axis of the receptacle 279c. In this case, that provides positive vertical offset of the second joint component with respect to the first joint component. FIG. 2U depicts the second prosthetic joint component 279b installed in the receptacle 279c so that there is a different angular offset between the longitudinal axis of the neck 279e with respect to the longitudinal axis of the receptacle 279c than was seen in FIG. 2T. In this case, that provides negative vertical offset of the second joint component with respect to the first joint component.

Figure 2P:
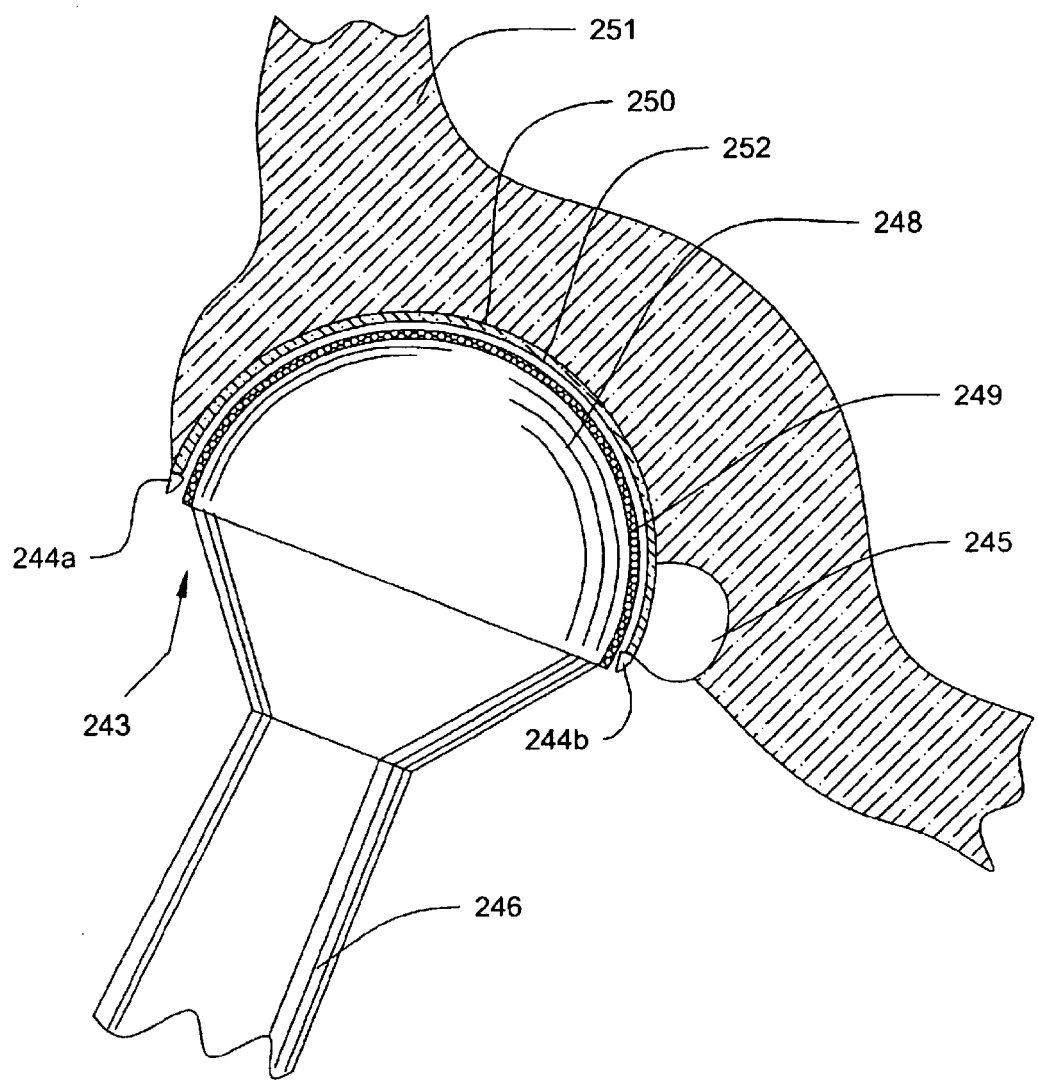
FIG. 2P depicts a prosthetic femoral head assembly of the invention in use in a hemiarthroplasty procedure.

In some instances it will be desired to replace only one half of a human joint with a prosthetic device, continuing to use the other half of the natural joint in conjunction with the newly implanted prosthetic device. An example of this is hemiarthroplasty. Referring to FIG. 2P, an embodiment of the invention useful for hemiarthroplasty is shown. A prosthetic femoral head member 243 is shown. A stem (now shown) may be included for fixation in a femur by any fixation method discussed herein. A neck is provided attached to a stem. A femoral head 247 is mounted to the neck 246. The femoral head is a polycrystalline diamond compact, including a substrate 248 and a diamond table 249.

Consistent with the principles of hemiarthroplasty, the femoral head member 243 has been installed into a patient's natural acetabular cup 250 of his hip 251 so that the load-bearing surface of the diamond table 249 of the femoral head 247 articulates against natural cartilage 252 of the natural acetabular cup 250. The labrum 244a and 244b and cotyloid notch 245 are undisturbed. In some instance hemiardiroplasty is preferred in order to avoid the trauma and healing associated with replacing a natural acetabular cup with a prosthetic device. The femoral head used for hemiarthroplasty may be spherical but will preferably be slightly aspherical. Use of an aspherical head promotes synovial fluid ingress to the natural acetabular cup for both lubrication and nourishment. Asphericity of the head may be achieved during finish machining, grinding and polishing of the head, or it may be achieved during manufacture by design of the substrate and loading and sintering of the diamond feedstock.

Figure 2R:
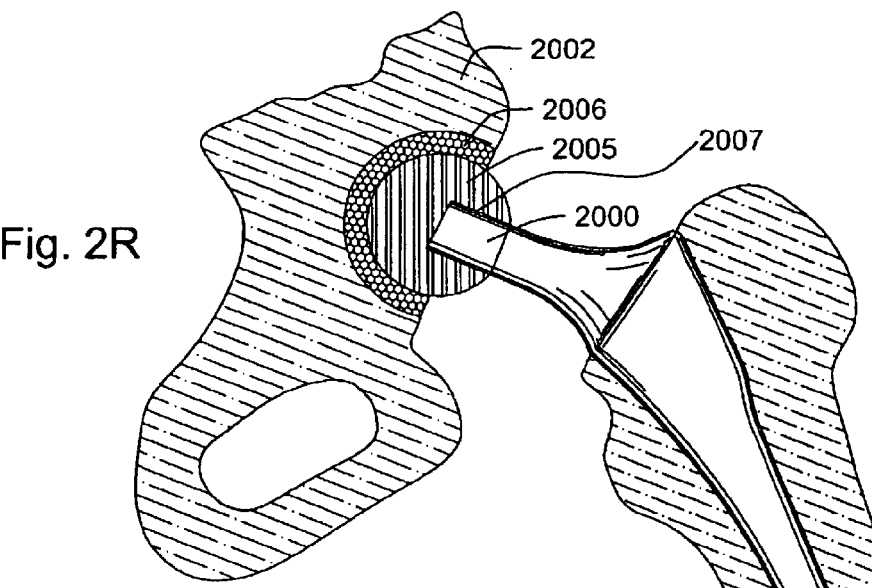
FIG. 2R depicts a hemiarthorplasty procedure in which the femoral component is a liner used to resurface a natural femoral head.
Figure 2Q:
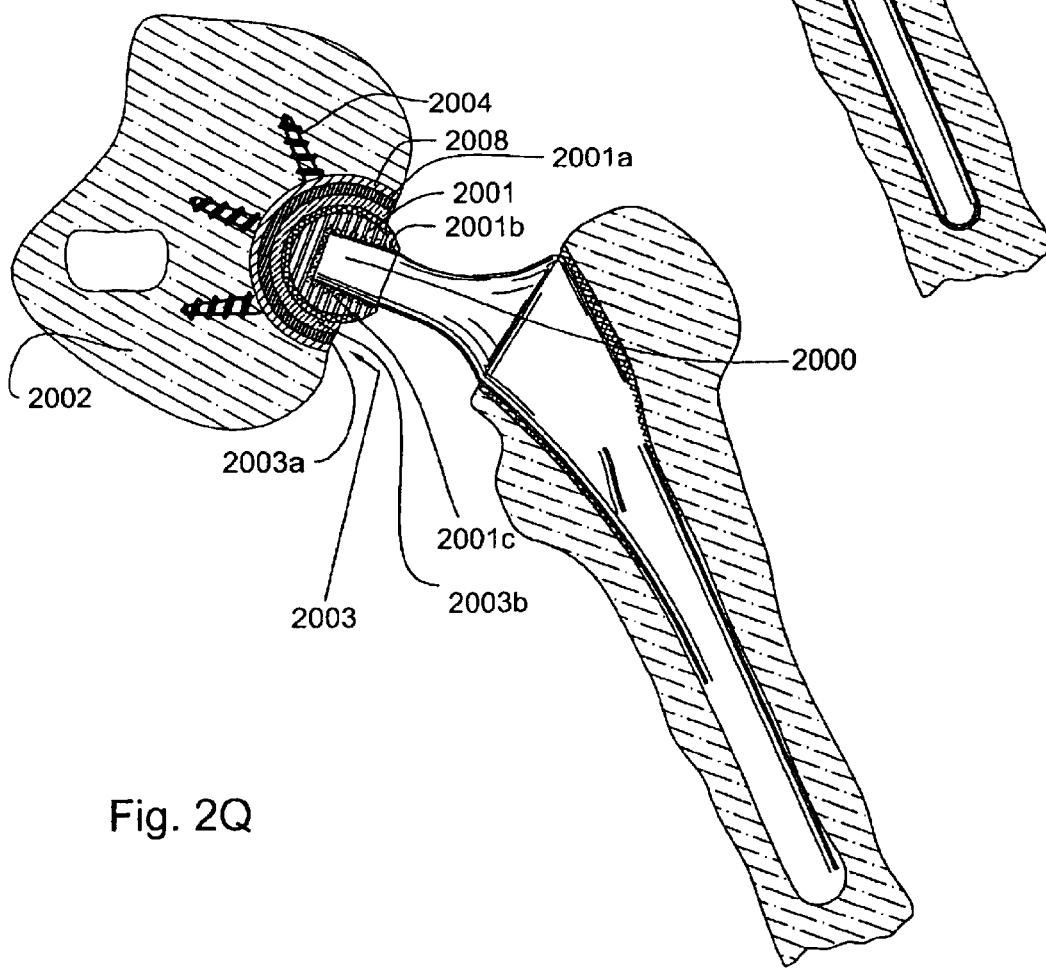
FIG. 2Q depicts a prosthetic hip joint of the invention where the femoral component is a liner used to resurface a natural femoral head.

Referring to FIG. 2Q, an alternative embodiment of the invention is employed for re-surfacing a femoral head. As depicted, the patient's femoral head has been re-surfaced with a prosthetic device and the patient's acetabular cup has been replaced. Re-surfacing the femoral head will allow preservation of as much of the patient's natural bone as possible because only the articulation surface and some adjacent bone are replaced. When a femoral head is re-surfaced, it may articulate against a natural acetabular cup or against a prosthetic acetabular cup. A re-surfacing head may be fixed to bone with any suitable means, including cement, biological fixation, porous surfaces, mechanical fasteners and otherwise. For fixation using porous surfaces, a porous metal substrate may be used, or the head may be made entirely of polycrystalline diamond with a porous bone ingrowth surface. As depicted in FIG. 2Q, the femoral head resurface is solid polycrystalline diamond with pores in the diamond to promote bone ingrowth and biological fixation.

In FIG. 2Q, the patient's natural femoral head 2000 has been shaped by a surgeon to an appropriate shape for relining, such as frusto-conical. A prosthetic femoral head surface 2001 has been placed over the frusto-conical attachment. The prosthetic femoral head surface 2001 is a polycrystalline diamond compact, including a diamond table 2001a sintered to a substrate 2001b. The substrate 2001b is formed to have a receptacle 2001c suitable for receiving a shaped bone. The diamond table 2001a serves as an articulation and load-bearing surface.

As depicted in the figure, the patient's natural hip 2002 has been fitted with a prosthetic acetabular cup 2003. The cup 2003 is a polycrystalline diamond compact, including a diamond table 2003b sintered to a substrate 2003a The diamond table 2003b and the diamond table 2001a articulate in sliding and rolling engagement with each other. The cup 2003 as depicted has been installed in an acetabular shell 2008, which is fixed to the bone 2002 with fasteners such as screws 2004. The shell has an internal cavity for receiving the acetabular cup bearing, and a securing member (not shown) used to secure the cup within the shell.

FIG. 2R depicts an alternative hemiarthroplasty procedure. A natural femoral head 2000 has been re-shaped by a surgeon to receive a prosthetic femoral head liner 2005. In this case, the femoral head liner depicted is solid polycrystalline diamond with an appropriate receptacle 2007 for accommodating the shaped bone. The polycrystalline diamond 2005 forms a load bearing and articulation surface for articulating against a patient's natural cartilage 2006 found on his hip 2002. Use of such a configuration achieves maximum bone preservation, minimum patient trauma, and maximum biocompatibility.

FIGS. 2V–2Z and 2AA–2AG depict examples of other prosthetic joints of the invention.

Figure 2V:
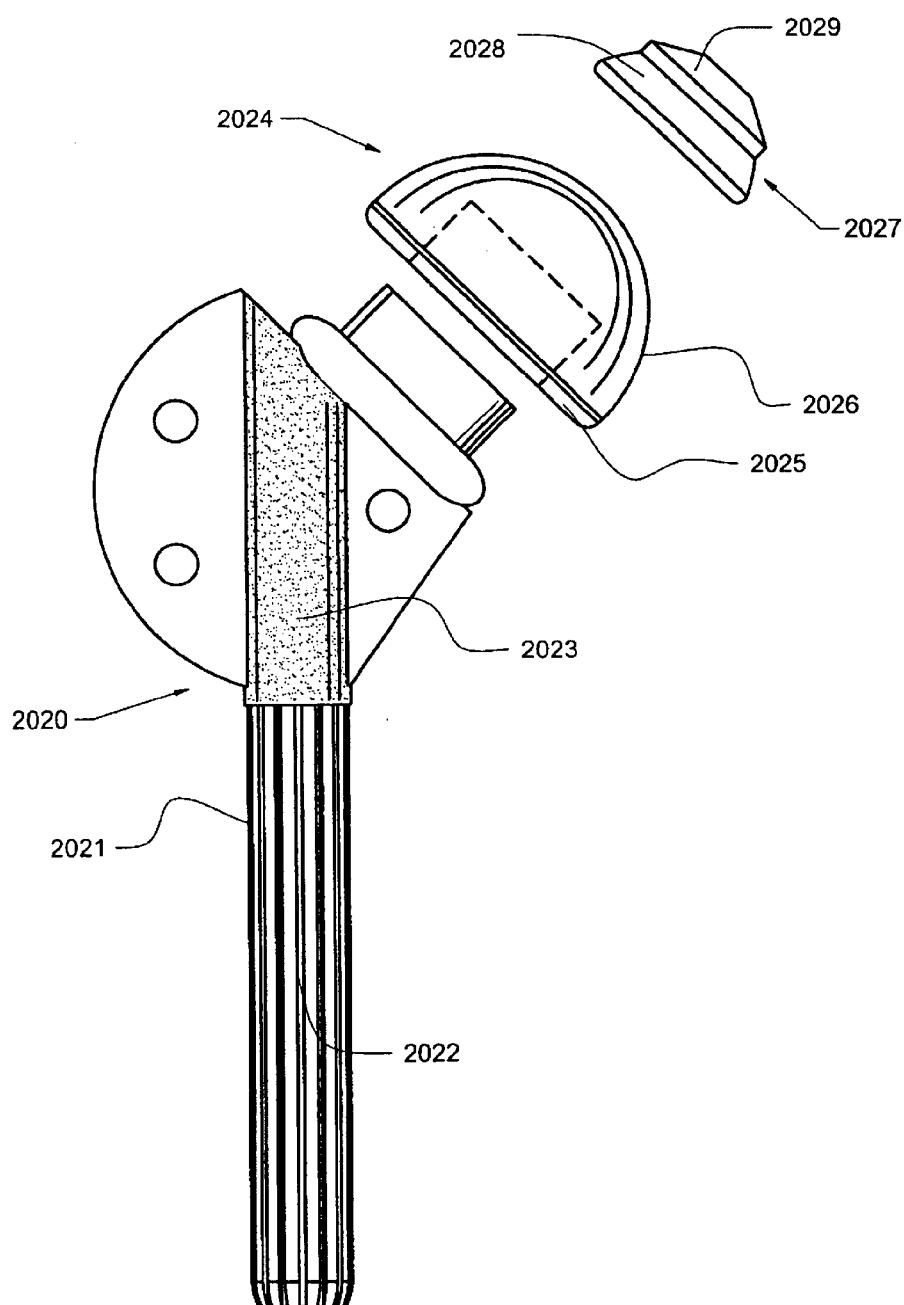
FIG. 2V depicts a shoulder joint of the invention.

FIG. 2V depicts a prosthetic shoulder joint 2020 of the invention. The particular configuration depicted is a modular joint but a non-modular joint, bi-angular, bi-polar or other shoulder joint could also be constructed according to the invention. The shoulder joint 2020 includes a humeral stem 2021 which may optionally include grooves or ridges 2022, a coated or textured bone mating surface 2023 and other features. A humeral head 2024 is provided that as depicted includes a polycrystalline diamond compact with a substrate 2025 and a polycrystalline diamond load bearing and articulation surface 2026. A glenoid component 2027 is depicted that includes a polycrystalline diamond compact providing a substrate 2029 supporting a polycrystalline diamond load bearing and articulation surface 2028.

Figure 2W:
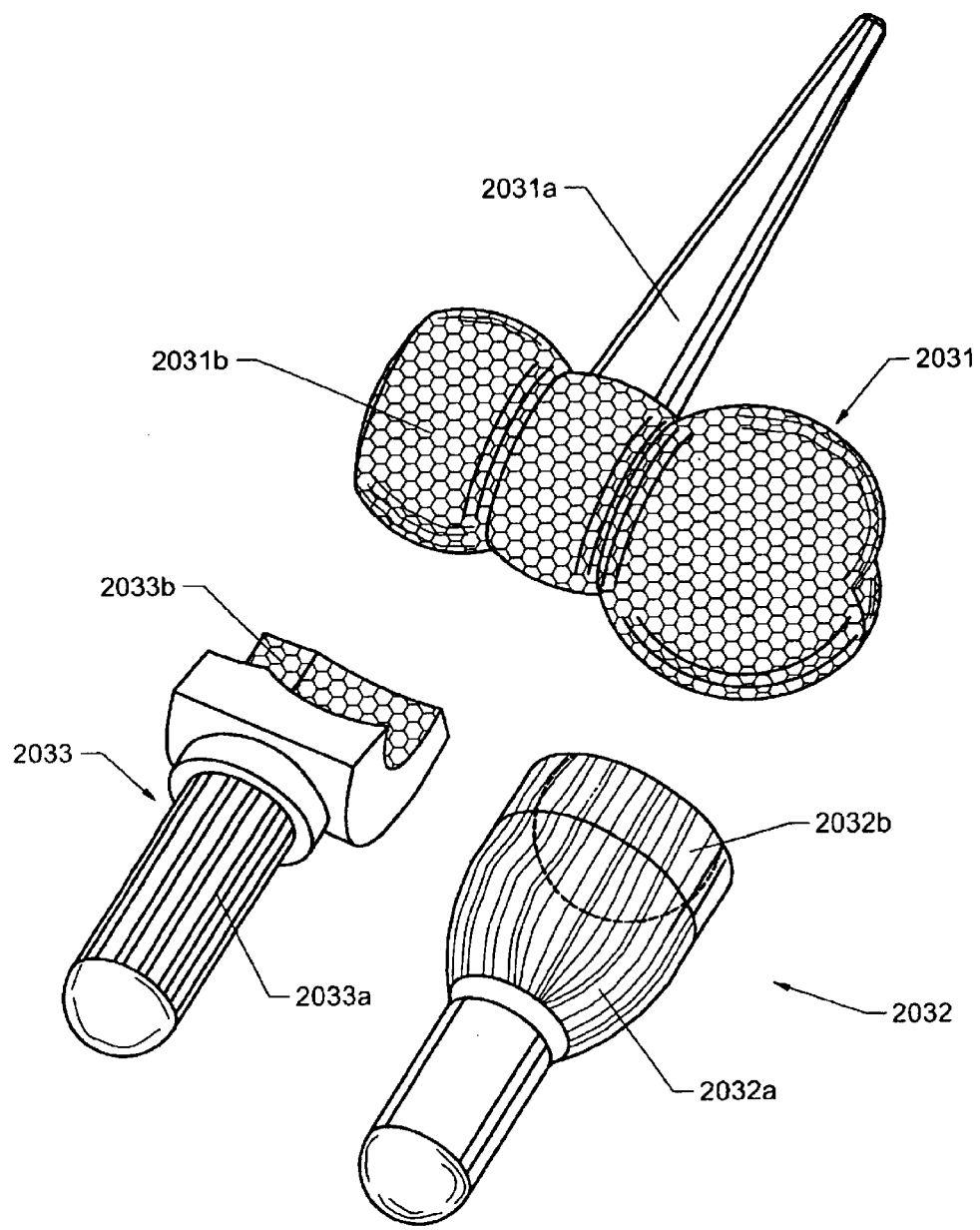
FIG. 2W depicts an elbow joint of the invention.

FIG. 2W depicts an unconstrained elbow joint 2030 of the invention. It includes humeral portion 2031, radial portion 2032 and ulnar potion 2033. These portions may be made from polycrystalline diamond compact or other preferred materials according to the invention. As depicted, humeral potion 2031, radial portion 2032 and ulnar portion 2033 each include a substrate 2031a, 2032a and 2033a and a diamond load bearing and articulation surface 2031b, 2032b and 2033c, respectively. Constrained elbow joints and single compartment elbow joint components may also be made according to the invention.

Figure 2X:
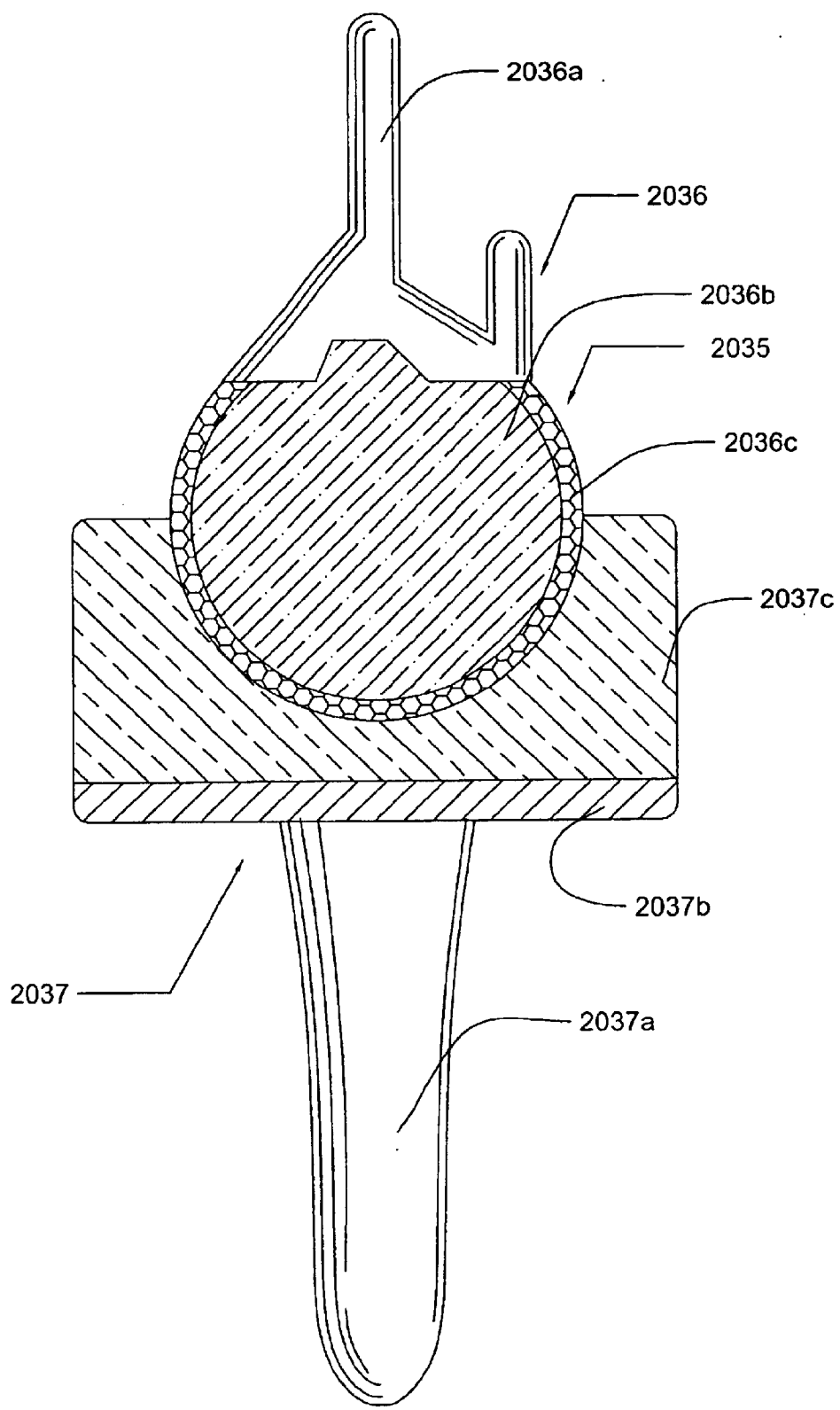
FIG. 2X depicts a prosthetic wrist joint of the invention.

FIG. 2X depicts a wrist joint 2035 according to the invention. The joint 2035 includes a first joint component 2036 and a second joint component 2037. The first joint component 2036 includes a bone attachment potion 2036a for attachment to a patient's bone. Affixed to the bone attachment portion 2036a is a substrate 2036b and a polycrystalline diamond load bearing and articulation surface 2036c comprising a polycrystalline diamond compact. The second joint component 2037 includes a bone attachment potion 2037a for attachment to a patient's bone. Affixed to the bone attachment portion 2037a is a substrate 2037b and a polycrystalline diamond load bearing and articulation surface 2037c comprising a polycrystalline diamond compact.

Figure 2Y:
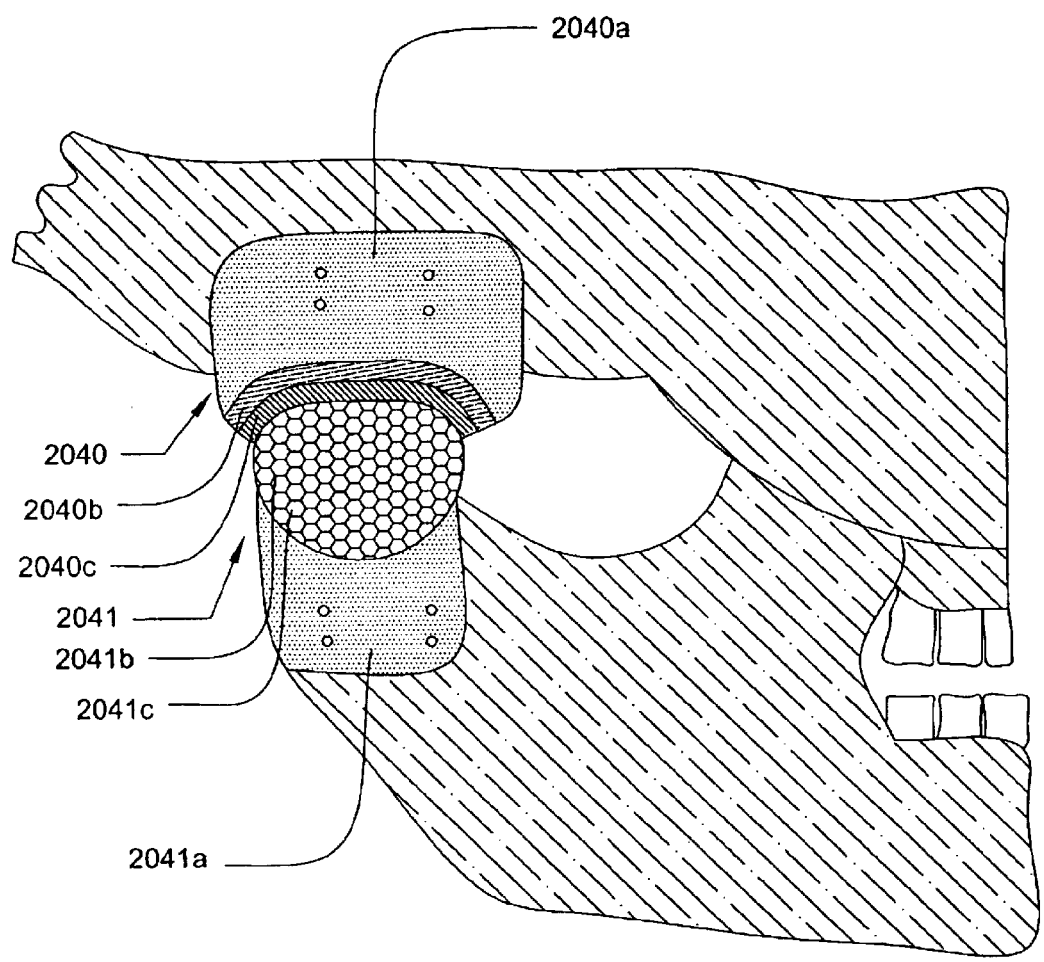
FIG. 2Y depicts a thrombomandibular joint of the invention.

FIG. 2Y depicts a prosthetic thorombomandibular joint of the invention. It includes a ramus portion 2040 and a mandibular portion 2041. The ramus portion 2040 includes an attachment plate 2040a for attaching to bone. The ramus portion 2041 includes a concave meniscus that is preferably a polycrystalline diamond compact having a substrate 2040b and a polycrystalline diamond load bearing and articulation surface 2040c. The mandibular portion 2041 includes an attachment plate 2041a for attaching to bone. It also includes a convex condyle 2041b that is preferably a polycrystalline diamond compact having a substrate (not shown) and a table of polycrystalline diamond 2041c thereon.

Figure 2Z:
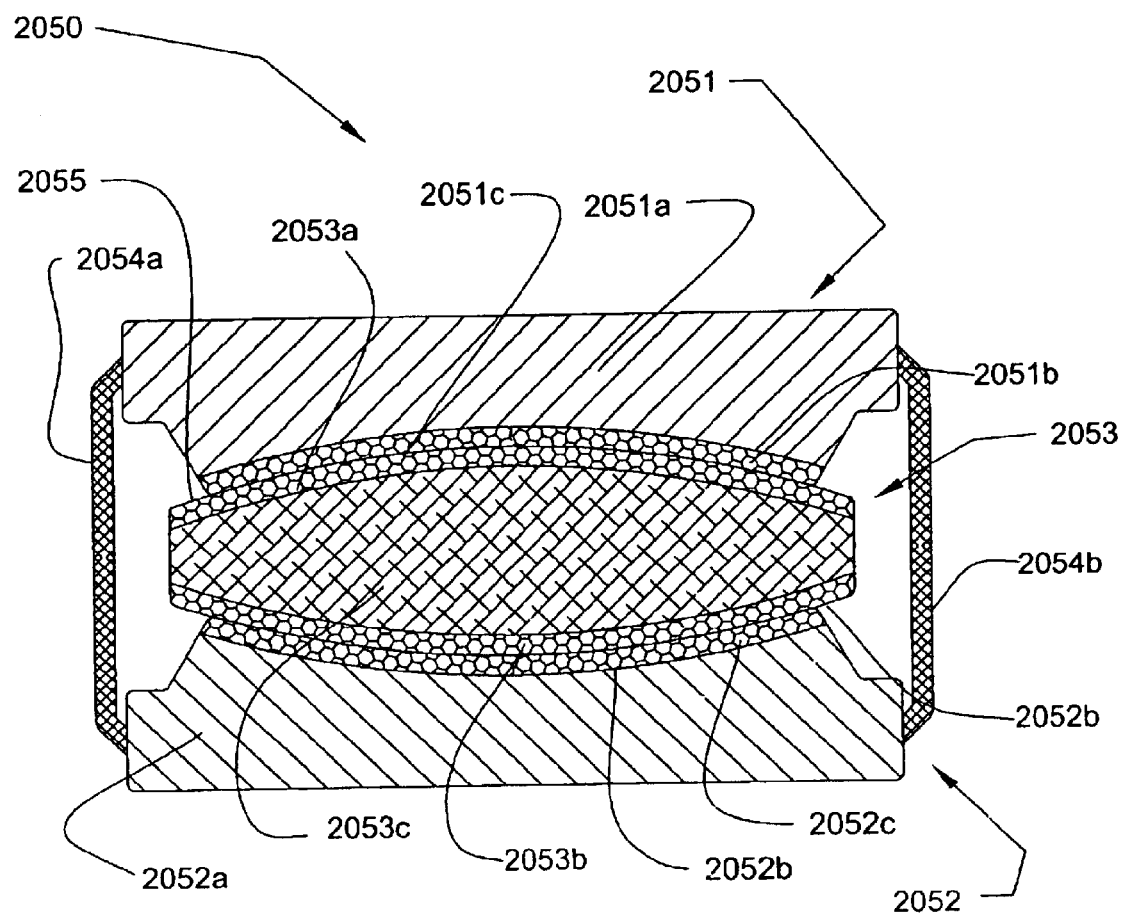
FIG. 2Z depicts an intervertrebal disc prosthesis of the invention.
Figure 2A:
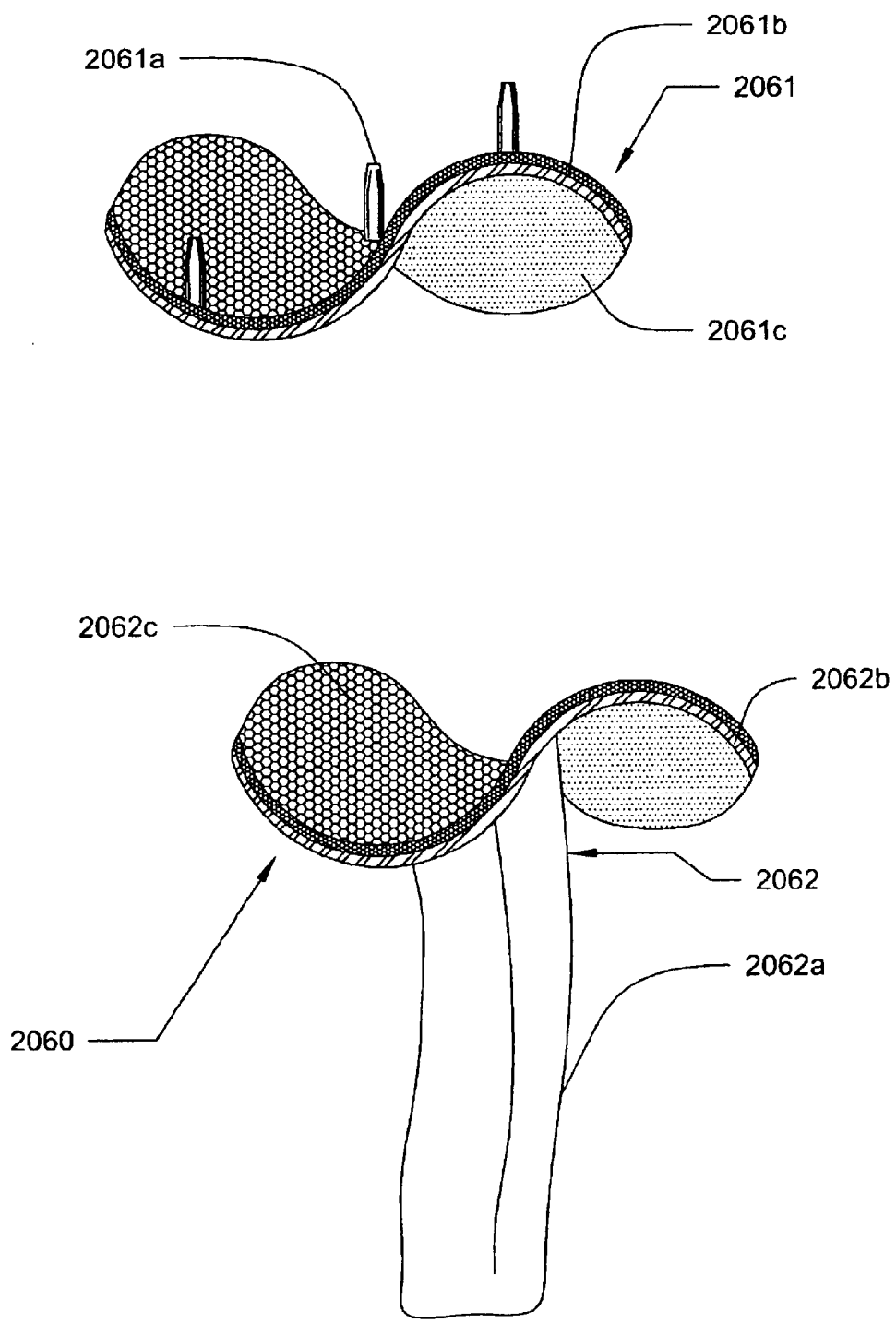
Figure 2A:
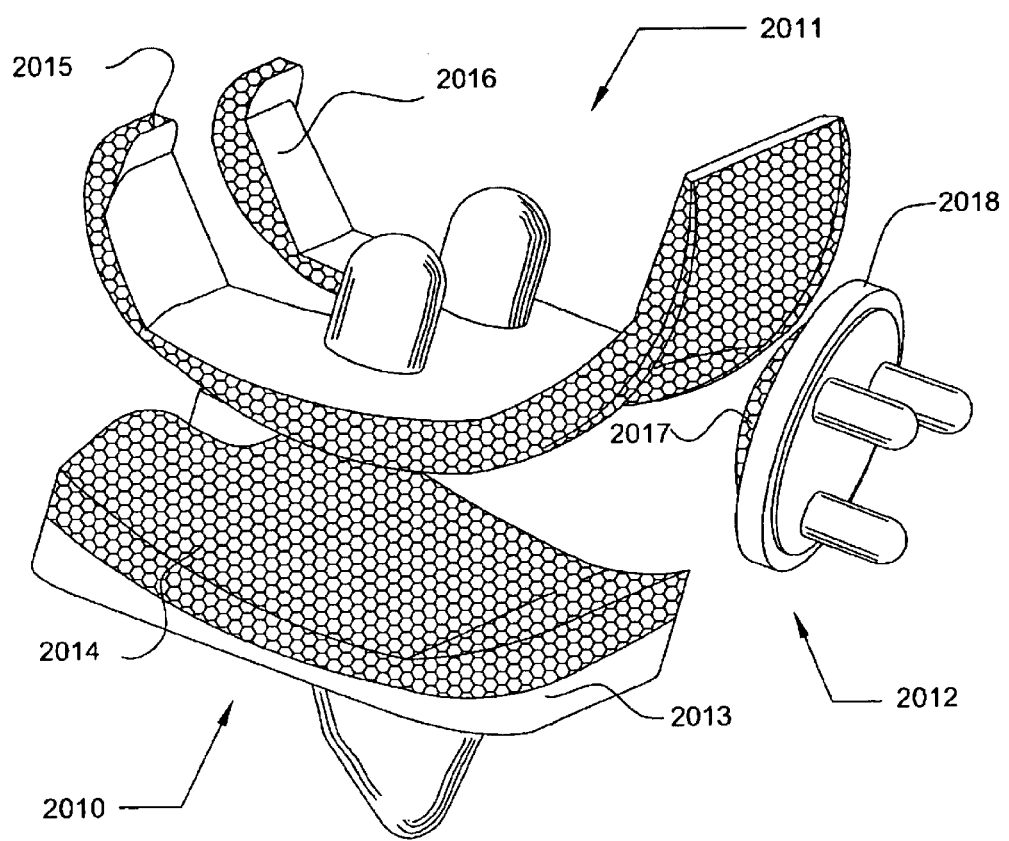
Figure 2A:
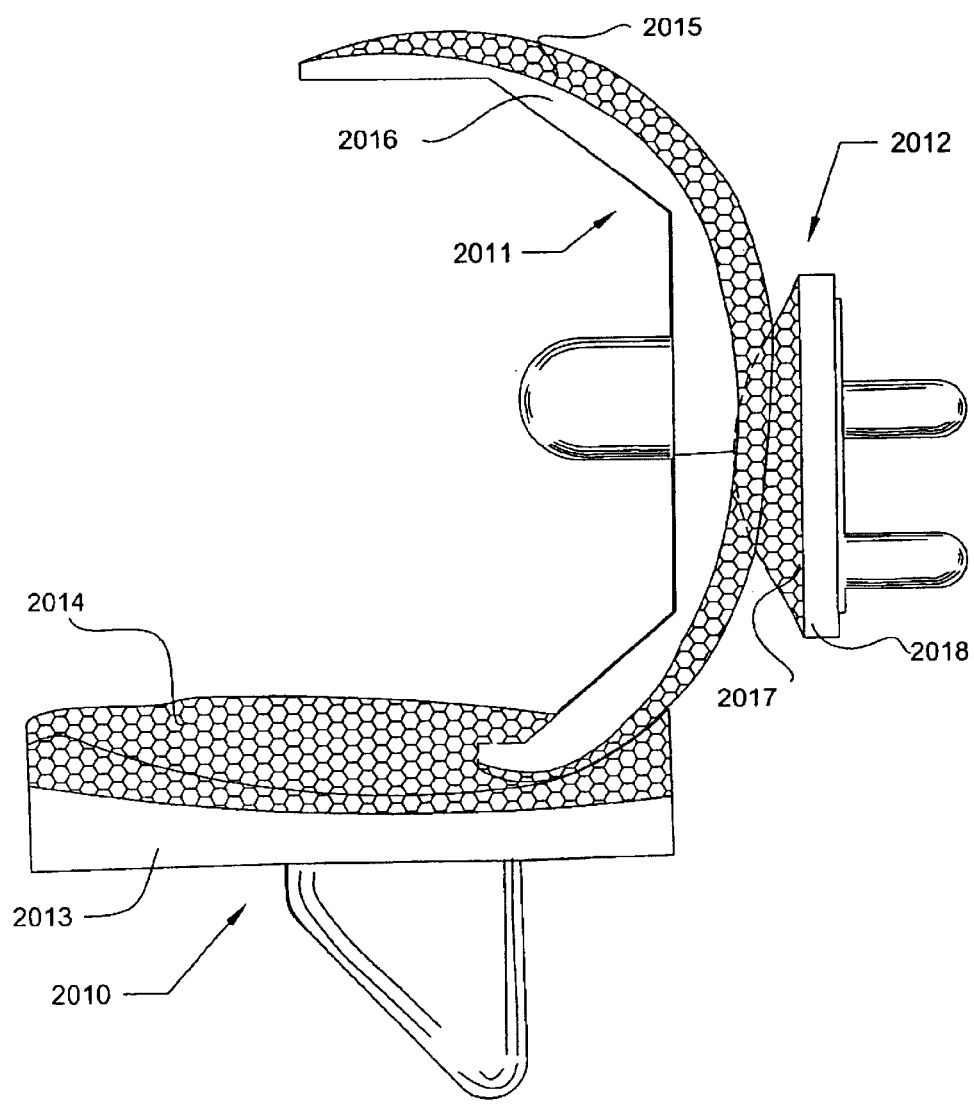

FIG. 2Z depicts an intervertebtral disc prosthesis 2050 of the invention. The disk prosthesis 2050 includes a top disk member 2051, a bottom disk member 2052 and a disk core 2053. The top disk member 2051 and bottom disk member 2052 are preferably held together by cables 2054a and 2054b or other attachment mechanisms to prevent overextension and dislocation. The top disk member 2051 includes a generally convex articulation portion 2051b. The articulation portion 2051b includes a polycrystalline diamond load bearing and articulation surface 2051c that is part of a polycrystalline diamond compact including a substrate 2051a. The bottom disk member 2052 includes a generally convex articulation portion 2052b. The articulation portion 2052b includes a polycrystalline diamond load bearing and articulation surface 2052c that is part of a polycrystalline diamond compact including a substrate 2052a. The two convex articulation portions form a cavity 2055 in which a disk core 2052 is found. The disk core 2055 permits sliding and rolling articulation of the top and bottom disk members with respect thereto. The disk core 2053 depicted includes a top convex articulation surface 2053a and a bottom convex articulation surface 2053b that are preferably polycrystalline diamond formed on a polycrystalline diamond compact that includes a substrate 2053c.

FIG. 2AA depicts a prosthetic joint useful in the carpometacaral joint in the thumb and in other areas of the body. The joint 2060 includes a first joint component 2061 having a bone attachment portion such as pegs or pins 2061a, a substrate 2061b, and a table of polycrystalline diamond 2061c which forms a load bearing and articulation surface. Opposing the first joint component 2061 is a second joint component 2062. The second joint component includes a bone attachment portion 2062a a substrate 2062b, and a table of polycrystalline diamond 2062c, which forms a load bearing and articulation surface for articulation against 2061c.

FIGS. 2AB and 2AC depict a prosthetic knee joint of the invention for total knee replacement. The joint includes a tibial component 2010, a femoral component 2011 and a patella component 2012. Preferably, each load bearing and articulation surface of the joint will be made from sintered polycrystalline diamond or another preferred material of the invention. As depicted, the tibial component includes a tray 2013 on which the load bearing and articulation portion 2014 is mounted. The tray 2013 may be a substrate to which is sintered polycrystalline diamond compact to serve as the load bearing and articulation portion 2014. Alternatively, the tray 2013 may be of the general configuration of those found in the prior art, and the load bearing and articulation portion 2014 may be solid polycrystalline diamond, a polycrystalline diamond compact including a substrate and a diamond table located on the substrate, or another appropriate load bearing and articulation surface material. The femoral component 2011 is depicted as having a load bearing and articulation surface 2015 located on a substrate 2016, but might be constructed as described for the tibial portion 2010 or otherwise. A patella component 2012 is provided which may be a polycrystalline diamond compact including a diamond table 2017 and a substrate 2018 or another structure as described herein.

FIGS. 2AD and 2AE depict side and front views, respectively, of a prosthetic joint useful for unicompartmental knee replacement. This joint is useful for treating disease of a single knee compartment where replacement of the entire knee joint is not necessary. The joint 2100 includes a femoral component 2101 with a polycrystalline diamond bearing surface 2102 and a substrate 2103. The tibial component 2104 is a tray with an appropriately shaped slot or receptacle 2105 for receiving a bearing insert 2106 therein. The slot 2105 permits anterior and posterior sliding motion in the joint. The bearing insert 2106 includes a protrusion 2107 for fitting in the slot 2105. The bearing insert 2106 also includes a substrate 2108 on which is found a polycrystalline diamond bearing surface 2109.

FIGS. 2AF and 2AG depict front and side views, respectively, of a sliding bearing rotating platform total knee joint 2030 of the invention. The joint 2030 includes a tibial tray 2031 with a receptacle therein 2032 for accepting a rotating platform 2033. The rotating platform 2033 has a protrusion 2034 for fitting into the receptacle 2032. The rotating platform 2033 accommodates rotational movement within the knee joint as indicated by arrows 2035a and 2035b. Sliding bearing inserts 2036a and 2036b fit into appropriately shaped slots in the rotating platform 2033 and permit anterior and posterior sliding motion in the knee joint. The bearing inserts 2036a and 2036b preferably include a diamond bearing surface 2037a and 2037b on a substrate 2038a and 2038b. A femoral component 2039 is provided which also preferably includes a diamond bearing surface 2040 on a substrate 2041.

The various joints mentioned above and other joints (including ankle, interphalangeal, and other joints) made using embodiments of the invention may be constructed in constrained and unconstrained configurations. Multi-compartment joints (such as knees) may be treated with a uni-compartmental prosthetic joint of the invention of a multi-compartmental joint of the invention. Ball and socket joints, hinge joints, sliding joints and other joints may be made according to the invention. In addition, all of the load bearing and articulations surfaces of a prosthetic joint or any subset of them may be made from a material or structure of the invention or by a method of the invention. If only a subset of the load bearing and articulation surfaces of a joint are made according to the invention, then the remaining portions of the joint may be made from other materials described herein or according to the prior art. Partial joint replacements (such as hemiarthroplasty and uni-compartment knee replacement) may also be accomplished using joint components of the invention. Prosthetic joints of any desired configuration, in addition to those depicted and discussed herein may be made according to the invention. Principles of the invention may be employed regardless of whether the joint is modular or non-modular, or whether an entire joint, a single joint component, or only an articulation surface is being manufactured.

C. Dimensions and Geometry of Preferred Joints

In the preferred hip joint of the invention, the ball includes at least a portion of a convex sphere and the socket includes at least a portion of a concave sphere. The spherically shaped portions of the ball and socket are preferably of similar radius so as to fit together with required tolerances. Appropriate tolerances for hard-hard bearing surfaces are known to persons of skill in the art. Very similar radiuses are desired for the cup and ball in a prosthetic hip joint so that they will entrain fluid for lubrication. It is also desired to utilize a cup and ball of similar radius in order to minimize stress fields for the articulation surface. In some preferred embodiments of the invention, the sphere on which the ball and socket spherical portions are based is a sphere that has a radius of about from less than 22 millimeters to more than about 60 millimeters. In a prosthetic joint, it is desirable to use the largest possible geometry that the patient's anatomy will permit in order to achieve the greatest range of motion and mechanical strength in excess of the supporting bone structures.

In those embodiments of the invention that include a diamond table on one of the articulation surfaces, the diamond table will typically be from submicron thickness to about 3000 microns thick or more. Some embodiments of the invention utilize a solid polycrystalline diamond component, such as a solid polycrystalline diamond ball or a solid polycrystalline diamond socket. In those cases, the diamond table dimension will equal the component dimension.

For ball and socket joints using a polycrystalline diamond compact with a substrate, it is expected that for ease of manufacturing, the polycrystalline diamond table will be from less than about 5 microns thick to more than about 2 millimeters thick in the most preferred embodiments of the invention. Other diamond joint surfaces might have thickness in the range of less than about 1 micron to more than about 10 microns, or solid polycrystalline diamond components could be used as described above.

Both the ball and cup should be as close to spherical as manufacturing and finishing processes allow. This will maximize the contact surface area of the ball and cup, in order to diffuse the contact load and to maximize wear life of the joint. It is also preferred that the ball have at least 180 degrees of articulating surface for rotation in the socket in order to approximate the range of motion of a natural joint.

In hemiarthroplasty, a small degree of asphericity may be desirable in order to promote ingress of synovial fluid, providing lubrication and nutrition to the cartilage counter-bearing surface.

In various embodiments of the invention, the geometry and dimensions of the bearing surface of the component may be designed to meet the needs of a particular application and may differ from that which is described above.

E. Attachment of Diamond in the Preferred Joint

1. Nature of the Diamond-Substrate Interface

In prior art prosthetic joints, a polyethylene articulation surface was cemented to a cup or mechanically fixed to a shell, such as by use of flanges, a locking ring, or tabs. Alternatively, the polyethylene articulation surface was injection molded onto an appropriate metal surface. None of the prior art provided a prosthetic joint with a diamond table articulation surface, a sintered polycrystalline diamond compact, or the transition zone of the invention.

In the preferred embodiment of the invention, a polycrystalline diamond compact provides unique chemical bonding and mechanical grip between the articulation surface and the substrate material, as compared to prior art cementing or mechanical fixation of a polyethylene articulation surface.

Some preferred prosthetic joint structures of the invention uses a polycrystalline diamond compact for at least one of the femoral head and/or the acetabular cup. A polycrystalline diamond compact, which utilizes a substrate material, will have a chemical bond between substrate material and the diamond crystals. The result of this structure is an extremely strong bond between the substrate and the diamond table.

Figure 4A:
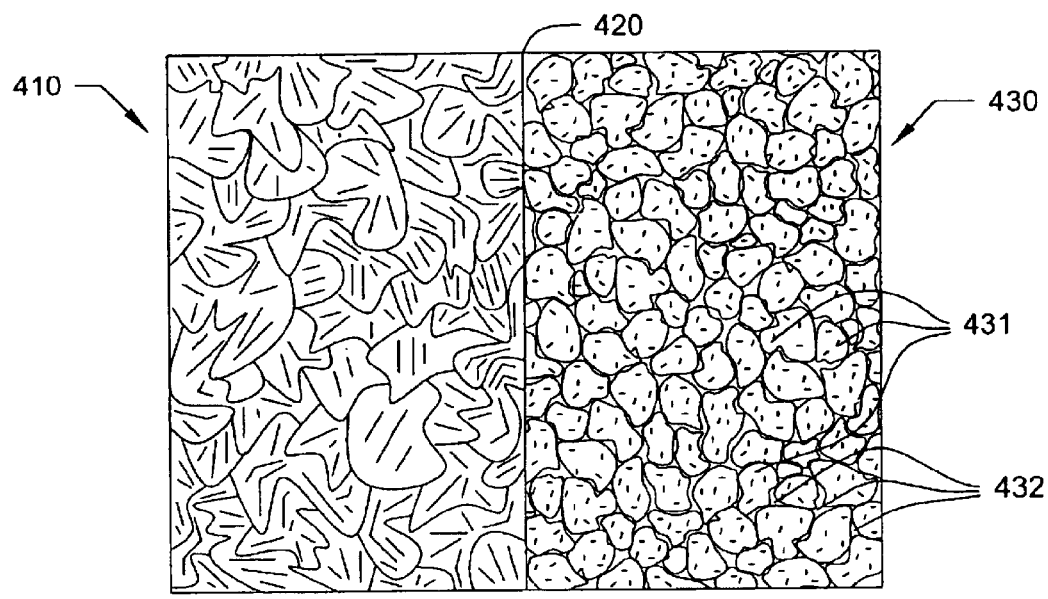
FIG. 4A depicts a quantity of diamond feedstock adjacent to a metal alloy substrate prior to sintering of the diamond feedstock and the substrate to create a polycrystalline diamond compact.
Figure 4B:
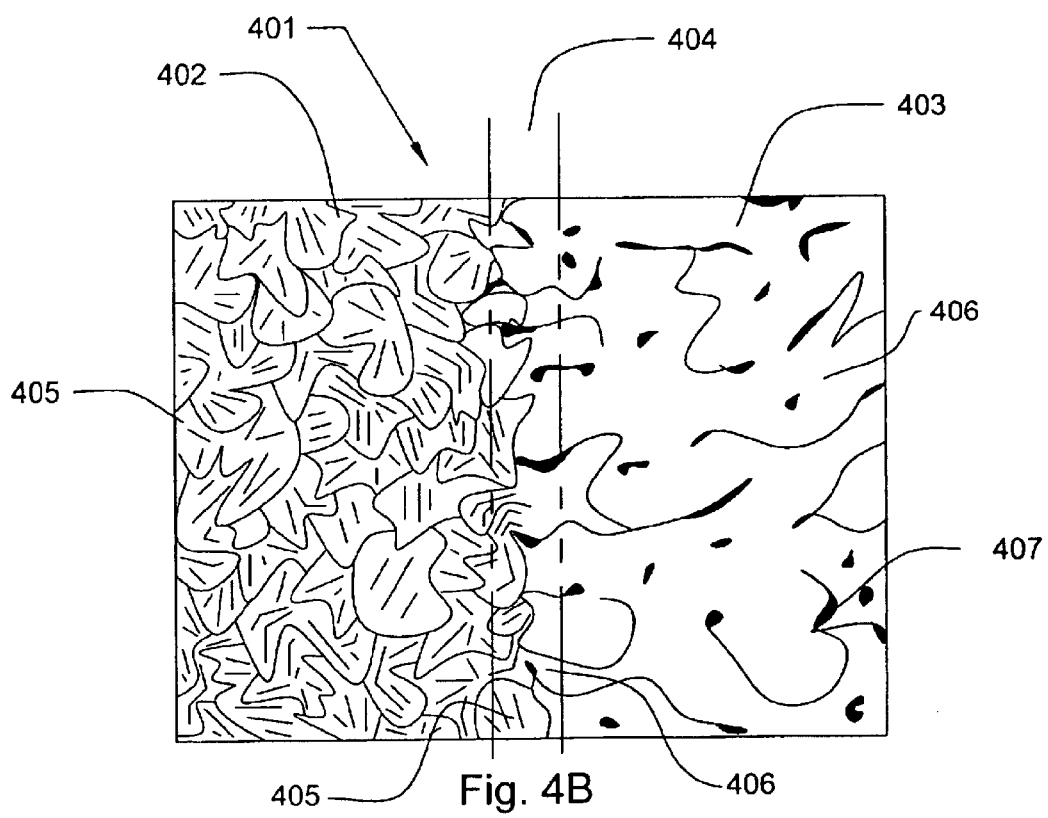
FIG. 4B depicts a sintered polycrystalline diamond compact in which the diamond table, the substrate, and the transition zone between the diamond table and the substrate are shown.
Figure 4B:
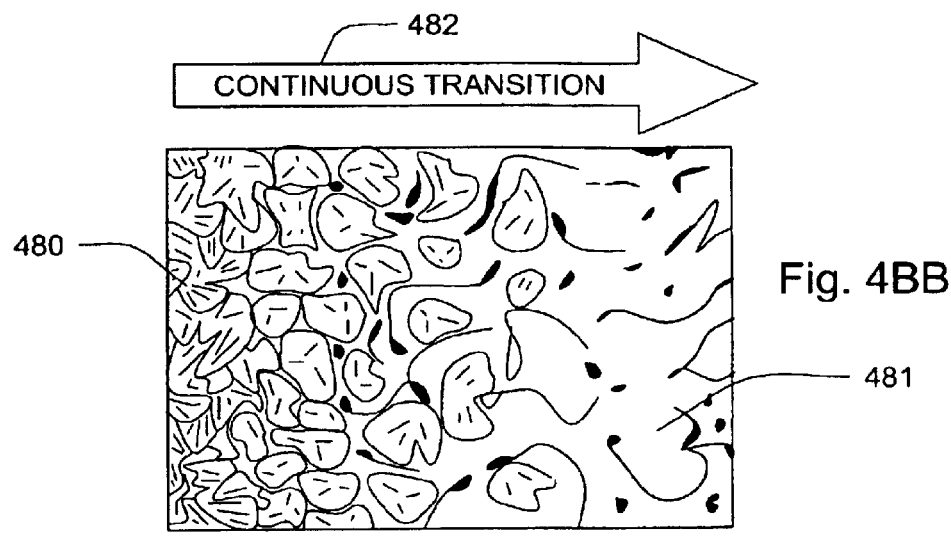

A method by which PDC is preferably manufactured is described later in this document. Briefly, it involves sintering diamond crystals to each other, and to a substrate under high pressure and high temperature. FIGS. 4A and 4B illustrate the physical and chemical processes involved manufacturing polycrystalline diamond compacts.

In FIG. 4A, a quantity of diamond feedstock 430 (such as diamond powder or crystals) is placed adjacent to a metal-containing substrate 410 prior to sintering. In the region of the diamond feedstock 430, individual diamond crystals 431 may be seen, and between the individual diamond crystals 431 there are interstitial spaces 432. If desired, a quantity of solvent-catalyst metal may be placed into the interstitial spaces 432.

The substrate 410 may be a suitable pure metal or alloy, or a cemented carbide containing a suitable metal or alloy as a cementing agent such as cobalt-cemented tungsten carbide. Preferably the substrate will be a metal with high tensile strength. In the preferred cobalt-chrome substrate of the invention, the cobalt-chrome alloy will serve as a solvent-catalyst metal for solvating diamond crystals during the sintering process.

The illustration shows the individual diamond crystals and the contiguous metal crystals in the metal substrate. The interface 420 between diamond powder and substrate material is a critical region where bonding of the diamond table to the substrate must occur. In some embodiments of the invention, a boundary layer of a third material different than the diamond and the substrate is placed at the interface 420. This interface boundary layer material, when present, may serve several functions including, but not limited to, enhancing the bond of the diamond table to the substrate, and mitigation of the residual stress field at the diamond-substrate interface.

Once diamond powder-or crystals and substrate are assembled as shown in FIG. 4A, the assembly is subjected to high pressure and high temperature as described later herein in order to cause bonding of diamond crystals to diamond crystals and to the substrate. The resulting structure of sintered polycrystalline diamond table bonded to a substrate is called a polycrystalline diamond compact (PDC). A compact, as the term is used herein, is a composite structure of two different materials, such as diamond crystals, and a substrate metal. The analogous structure incorporating cubic boron nitride crystals in the sintering process instead of diamond crystals is called polycrystalline cubic boron nitride compact (PCBNC). Many of the processes described herein for the fabrication and finishing of PDC structures and parts work in a similar fashion for PCBNC. In some embodiments of the invention, PCBNC may be substituted for PDC.

FIG. 4B depicts a polycrystalline diamond compact 401 after the high pressure and high temperature sintering of diamond feedstock to a substrate. Within the PDC structure, there is an identifiable volume of substrate 402, an identifiable volume of diamond table 403, and a transition zone 404 between diamond table and substrate containing diamond crystals and substrate material. Crystalline grains of substrate material 405 and sintered crystals of diamond 406 are depicted.

On casual examination, the finished compact of FIG. 4B will appear to consist of a solid table of diamond 403 attached to the substrate 402 with a discrete boundary. On very close examination, however, a transition zone 404 between diamond table 403 and substrate 402 can be characterized. This zone represents a gradient interface between diamond table and substrate with a gradual transition of ratios between diamond content and metal content. At the substrate side of the transition zone, there will be only a small percentage of diamond crystals and a high percentage of substrate metal, and on the diamond table side, there will be a high percentage of diamond crystals and a low percentage of substrate metal. Because of this gradual transition of ratios of polycrystalline diamond to substrate metal in the transition zone, the diamond table and the substrate have a gradient interface.

In the transition zone where diamond crystals and substrate metal are intermingled, chemical bonds are formed between the diamond and metal. From the transition zone 404 into the diamond table 403, the metal content diminishes and is limited to solvent-catalyst metal that fills the three-dimensional vein-like structure of interstitial voids or openings 407 within the sintered diamond table structure 403. The solvent-catalyst metal found in the voids or openings 407 may have been swept up from the substrate during sintering or may have been solvent-catalyst metal added to the diamond feedstock before sintering.

During the sintering process, there are three types of chemical bonds that are created; diamond-to-diamond bonds, diamond-to-metal bonds, and metal-to-metal bonds. In the diamond table, there are diamond-to-diamond bonds (sp3 carbon bonds) created when diamond particles partially solvate in the solvate-catalyst metal and then are bonded together. In the substrate and in the diamond table, there are metal-to-metal bonds created by the high pressure and high temperature sintering process. And in the gradient transition zone, diamond-to-metal bonds are created between diamond and solvent-catalyst metal.

The combination of these various chemical bonds and the mechanical grip exerted by solvent-catalyst metal in the diamond table such as in the interstitial spaces of the diamond structure diamond table provide extraordinarily high bond strength between the diamond table and the substrate. Interstitial spaces are present in the diamond structure and those spaces typically are filled with solvent-catalyst metal, forming veins of solvent-catalyst metal within the polycrystalline diamond structure. This bonding structure contributes to the extraordinary fracture toughness of the compact, and the veins of metal within the diamond table act as energy sinks halting propagation of incipient cracks within the diamond structure. The transition zone and metal vein structure provide the compact with a gradient of material properties between those of the diamond table and those of substrate material, further contributing to the extreme toughness of the compact. The transition zone can also be called an interface, a gradient transition zone, a composition gradient zone, or a composition gradient, depending on its characteristics. The transition zone distributes diamond/substrate stress over the thickness of the zone, reducing zone high stress of a distinct linear interface. The subject residual stress is created as pressure and temperature are reduced at the conclusion of the high pressure/high temperature sintering process due to the difference in pressure and thermal expansive properties of the diamond and substrate materials.

The diamond sintering process occurs under conditions of extremely high pressure and high temperature. According to the inventors' best experimental and theoretical understanding, the diamond sintering process progresses through the following sequence of events. At pressure, a cell containing feedstock of unbonded diamond powder or crystals (diamond feedstock) and a substrate is heated to a temperature above the melting point of the substrate metal 410 and molten metal flows or sweeps into the interstitial voids 407 between the adjacent diamond crystals 406. It is carried by the pressure gradient to fill the voids as well as being pulled in by the surface energy or capillary action of the large surface area of the diamond crystals 406. As the temperature continues to rise, carbon atoms from the surface of diamond crystals dissolve into this interstitial molten metal, forming a carbon solution.

At the proper threshold of temperature and pressure, diamond becomes the thermodynamically favored crystalline allotrope of carbon. As the solution becomes super saturated with respect to $C_d$ (carbon diamond), carbon from this solution begins to crystallize as diamond onto the surfaces of diamond crystals bonding adjacent diamond crystals together with diamond-diamond bonds into a sintered polycrystalline diamond structure 406. The interstitial metal fills the remaining void space forming the vein-like lattice structure 407 within the diamond table by capillary forces and pressure driving forces. Because of the crucial role that the interstitial metal plays in forming a solution of carbon atoms and stabilizing these reactive atoms during the diamond crystallization phase in which the polycrystalline diamond structure is formed, the metal is referred to as a solvent-catalyst metal.

FIG. 4BB depicts a polycrystalline diamond compact having both substrate metal 480 and diamond 481, but in which there is a continuous gradient transition 482 from substrate metal to diamond. In such a compact, the gradient transition zone may be the entire compact.

In some embodiments of the invention, a quantity of solvent-catalyst metal may be combined with the diamond feedstock prior to sintering. This is found to be necessary when forming thick PCD tables, solid PDC structures, or when using multimodal fine diamond where there is little residual free space within the diamond powder. In each of these cases, there is insufficient ingress of solvent-catalyst metal via the sweep mechanism to adequately mediate the sintering process as a solvent-catalyst. The metal may be added by direct addition of powder, or by generation of metal powder in situ with an attritor mill or by the well-known method of chemical reduction of metal salts deposited on diamond crystals. Added metal may constitute any amount from less than 1% by mass, to greater than 35%. This added metal may consist of the same metal or alloy as is found in the substrate, or may be a different metal or alloy selected because of its material and mechanical properties. Example ratios of diamond feedstock to solvent-catalyst metal prior to sintering include mass ratios of 70:30, 85:15, 90:10, and 95:15. The metal in the diamond feedstock may be added powder metal, metal added by an attritor method, vapor deposition or chemical reduction of metal into powder.

When sintering diamond on a substrate with an interface boundary layer, no solvent-catalyst metal from the substrate is available to sweep into the diamond table and participate in the sintering process. In this case, the boundary layer material, if composed of a suitable material, metal or alloy that can function as a solvent-catalyst, may serve as the sweep material mediating the diamond sintering process. In other cases where the desired boundary material cannot serve as a solvent-catalyst, a suitable amount of solvent-catalyst metal powder as described herein is added to the diamond crystal feed stock as described above. This assembly is then taken through the sintering process. In the absence of a substrate metal source, the solvent-catalyst metal for the diamond sintering process must be supplied entirely from the added metal powder. The boundary material bonds chemically to the substrate material, and bonds chemically to the diamond table and/or the added solvent-catalyst metal in the diamond table. The remainder of the sintering and fabrication process are the same as with the conventional solvent-catalyst sweep sintering and fabrication process.

For the sake of simplicity and clarity in this patent, the substrate, transition zone, and diamond table have been discussed as distinct layers. However, it is important to realize that the finished sintered object consists of a composite structure characterized by a continuous gradient transition from substrate material to diamond table rather than as distinct layers with clear and discrete boundaries, hence the term "compact".

In addition to the sintering processes described above, diamond parts suitable for use as bearings for such applications as total hips may also be fabricated as solid polycrystalline diamond structures without a substrate. These are formed by placing the diamond powder combined with a suitable amount of added solvent-catalyst metal powder as described above in a refractory metal can (typically Ta, Nb, Zr, or Mo) with a shape approximating the shape of the final part desired. This assembly is then taken through the sintering process. However, in the absence of a substrate metal source, the solvent-catalyst metal for the diamond sintering process must be supplied entirely from the added metal powder. With suitable finishing, objects thus formed may be used as is, or bonded to metal substrates to function as total joint articulations.

Sintering is the preferred method of creating a diamond table with a strong and durable bond to a substrate material. Other methods of producing a diamond table bonded to a substrate are possible. At present, these typically are not as strong or durable as those fabricated with the sintering process. It is also possible to use these methods to form diamond structures directly onto substrates suitable for use as prosthetic joint bearings. A table of polycrystalline diamond either with or without a substrate may be manufactured and later attached to a prosthetic joint in a location such that it will form a bearing surface. The attachment could be performed with any suitable method, including welding, brazing, sintering, diffusion welding, diffusion bonding, inertial welding, adhesive bonding, or the use of fasteners such as screws, bolts, or rivets. In the case of attaching a diamond table without a substrate to another object, the use of such methods as brazing, diffusion welding/bonding or inertia welding may be most appropriate.

2. Alternative Methods for Creating a Diamond Bearing Surface

Although high pressure/high temperature sintering is the preferred method for creating a diamond bearing surface, other methods for producing a volume of diamond may be employed as well. For example, either chemical vapor deposition (CVD), or physical vapor deposition (PVD) processes may be used. CVD produces a diamond layer by thermally cracking an organic molecule and depositing carbon radicals on a substrate. PVD produces a diamond layer by electrically causing carbon radicals to be ejected from a source material and to deposit on a substrate where they build a diamond crystal structure.

The CVD and PVD processes have some advantages over sintering. Sintering is performed in large, expensive presses at high pressure (such as 45–68 kilobars) and at high temperatures (such as 1200 to 1500 degrees Celsius). It is difficult to achieve and maintain desired component shape using a sintering process because of flow of high pressure mediums used and possible deformation of substrate materials.

In contrast, CVD and PVD take place at atmospheric pressure or lower, so there no need for a pressure medium and there is no deformation of substrates.

Another disadvantage of sintering is that it is difficult to achieve some geometries in a sintered polycrystalline diamond compact. When CVD or PVD are used, however, the gas phase used for carbon radical deposition can completely conform to the shape of the object being coated, making it easy to achieve a desired non-planar shape.

Another potential disadvantage of sintering polycrystalline diamond compacts is that the finished component will tend to have large residual stresses caused by differences in the coefficient of thermal expansion and modulus between the diamond and the substrate. While residual stresses can be used to improve strength of a part, they can also be disadvantageous. When CVD or PVD is used, residual stresses can be minimize because CVD and PVD processes do not involve a significant pressure transition (such from 68 Kbar to atmospheric pressure in high pressure and high temperature sintering) during manufacturing.

Another potential disadvantage of sintering polycrystalline diamond compacts is that few substrates have been found that are suitable for sintering. In the prior art, the typical substrate used was tungsten carbide. In the invention, non-planar components have been made using other substrates. When CVD or PVD are used, however, synthetic diamond can be placed on many substrates, including titanium, most carbides, silicon, molybdenum and others. This is because the temperature and pressure of the CVD and PVD coating processes are low enough that differences in coefficient of thermal expansion and modulus between diamond and the substrate are not as critical as they are in a high temperature and high pressure sintering process.

A further difficulty in manufacturing sintered polycrystalline diamond compacts is that as the size of the part to be manufactured increases, the size of the press must increase as well. Sintering of diamond will only take place at certain pressures and temperatures, such as those described herein. In order to manufacture larger sintered polycrystalline diamond compacts, ram pressure of the press (tonnage) and size of tooling (such as dies and anvils) must be increased in order to achieve the necessary pressure for sintering to take place. But increasing the size and capacity of a press is more difficult than simply increasing the dimensions of its components. There may be a practical physical size constraints on press size due to the manufacturing process used to produce press tooling.

Tooling for a press is typically made from cemented tungsten carbide. In order to make tooling, the cemented tungsten carbide is sintered in a vacuum furnace followed by pressing in a hot isosatic press ("HIP") apparatus. Hipping must be performed in a manner that maintains uniform temperature throughout the tungsten carbide in order to achieve uniform physical qualities and quality. These requirements impose a practical limit on the size tooling that can be produced for a press that is useful for sintering polycrystalline diamond compacts. The limit on the size tooling that can be produced also limits the size press that can be produced.

CVD and PVD manufacturing apparatuses may be scaled up in size with few limitations, allowing them to produce polycrystalline diamond compacts of almost any desired size.

CVD and PVD processes are also advantageous because they permit precise control of the thickness and uniformity of the diamond coating to be applied to a substrate. Temperature is adjusted within the range of 500 to 1000 degrees Celsius, and pressure is adjusted in a range of less than 1 atmosphere to achieve desired diamond coating thickness.

Another advantage of CVD and PVD processes is that they allow the manufacturing process to be monitored as it progresses. A CVD or PVD reactor can be opened before manufacture of a part is completed so that the thickness and quality of the diamond coating being applied to the part may be determined. From the thickness of the diamond coating that has already been applied, time to completion of manufacture can be calculated. Alternatively, if the coating is not of desired quality, the manufacturing processes may be aborted in order to save time and money.

In contrast, sintering of polycrystalline diamond compacts is performed as a batch process that cannot be interrupted, and progress of sintering cannot be monitored. The pressing process must be run to completion and the part may only be examined afterward.

CVD is performed in an apparatus called a reactor. A basic CVD reactor includes four components. The first component of the reactor is one or more gas inlets. Gas inlets may be chosen based on whether gases are premixed before introduction to the chamber or whether the gases are allowed to mix for the first time in the chamber. The second component of the reactor is one or more power sources for the generation of thermal energy. A power source is needed to heat the gases in the chamber. A second power source may be used to heat the substrate material uniformly in order to achieve a uniform coating of diamond on the substrate. The third component of the reactor is a stage or platform on which a substrate is placed. The substrate will be coated with diamond during the CVD process. Stages used include a fixed stage, a translating stage, a rotating stage and a vibratory stage. An appropriate stage must be chosen to achieved desired diamond coating quality and uniformity. The fourth component of the reactor is an exit port for removing exhaust gas from the chamber. After gas has reacted with the substrate, it must be removed from the chamber as quickly as possible so that it does not participate in other reactions, which would be deleterious to the diamond coating.

CVD reactors are classified according to the power source used. The power source is chosen to create the desired species necessary to carry out diamond thin film deposition. Some CVD reactor types include plasma-assisted microwave, hot filament, electron beam, single, double or multiple laser beam, arc jet and DC discharge. These reactors differ in the way they impart thermal energy to the gas species and in their efficiency in breaking gases down to the species necessary for deposition of diamond. It is possible to have an array of lasers to perform local heating inside a high pressure cell. Alternatively, an array of optical fibers could be used to deliver light into the cell.

The basic process by which CVD reactors work is as follows. A substrate is placed into the reactor chamber. Reactants are introduced to the chamber via one or more gas inlets. For diamond CVD, methane ($CH_4$) and hydrogen ($H_2$) gases are preferably brought into the chamber in premixed form. Instead of methane, any carbon-bearing gas in which the carbon has sp3 bonding may be used. Other gases may be added to the gas stream in order to control quality of the diamond film, deposition temperature, gain structure and growth rate. These include oxygen, carbon dioxide, argon, halogens and others.

The gas pressure in the chamber is preferably maintained at about 100 torr. Flow rates for the gases through the chamber are preferably about 10 standard cubic centimeters per minute for methane and about 100 standard cubic centimeters per minute for hydrogen. The composition of the gas phase in the chamber is preferably in the range of 90–99.5% hydrogen and 0.5–10% methane.

When the gases are introduced into the chamber, they are heated. Heating may be accomplished by many methods. In a plasma-assisted process, the gases are heated by passing them through a plasma. Otherwise, the gases may be passed over a series of wires such as those found in a hot filament reactor.

Heating the methane and hydrogen will break them down into various free radicals. Through a complicated mixture of reactions, carbon is deposited on the substrate and joins with other carbon to form crystalline diamond by sp3 bonding. The atomic hydrogen in the chamber reacts with and removes hydrogen atoms from methyl radicals attached to the substrate surface in order to create molecular hydrogen, leaving a clear solid surface for further deposition of free radicals.

If the substrate surface promotes the formation of sp2 carbon bonds, or if the gas composition, flow rates, substrate temperature or other variables are incorrect, then graphite rather than diamond will grow on the substrate.

There are many similarities between CVD reactors and processes and PVD reactors and processes. PVD reactors differ from CVD reactors in the way that they generate the deposition species and in the physical characteristics of the deposition species. In a PVD reactor, a plate of source material is used as a thermal source, rather than having a separate thermal source as in CVD reactors. A PVD reactor generates electrical bias across a plate of source material in order to generate and eject carbon radicals from the source material. The reactor bombards the source material with high energy ions. When the high energy ions collide with source material, they cause ejection of the desired carbon radicals from the source material. The carbon radicals are ejected radially from the source material into the chamber. The carbon radicals then deposit themselves onto whatever is in their path, including the stage, the reactor itself, and the substrate.

Figure 4C:
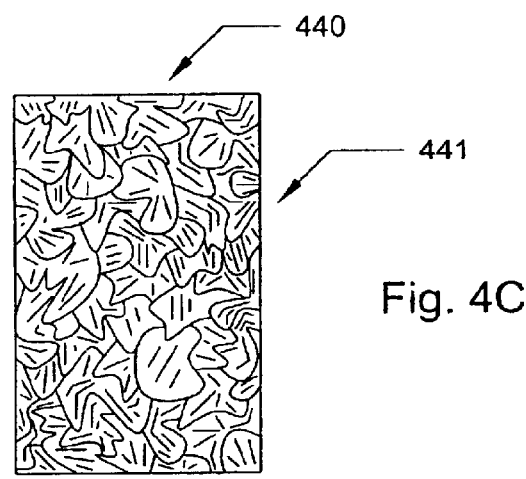
FIG. 4C depicts a substrate prior to use of a CVD or PVD process for form a volume of diamond on the substrate.
Figure 4D:
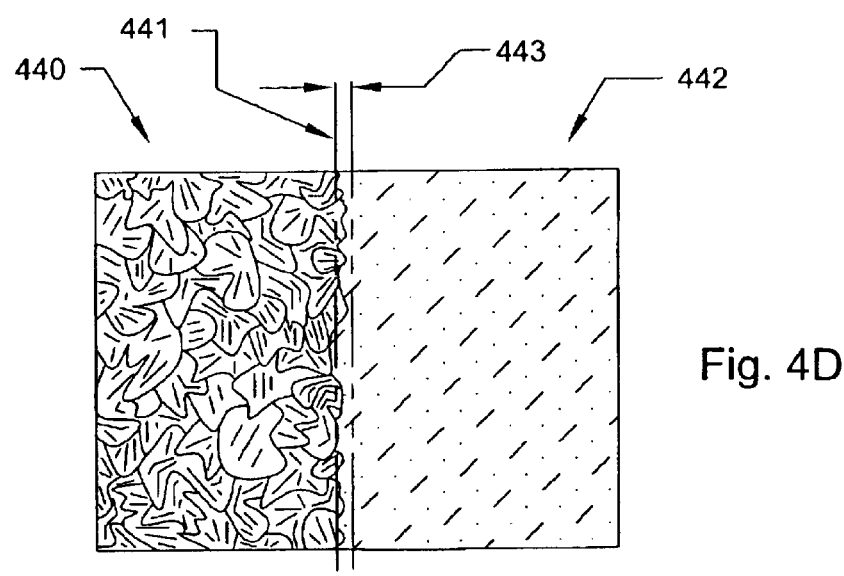
FIG. 4D depicts a diamond compact formed by a CVD or PVD process.

Referring to FIG. 4C, a substrate 440 of appropriate material is depicted having a deposition face 441 on which diamond may be deposited by a CVD or PVD process. FIG. 4D depicts the substrate 440 and the deposition face 441 on which a volume of diamond 442 has been deposited by CVD or PVD processes. A small transition zone 443 is present in which both diamond and substrate are located. In comparison to FIG. 4B, it can be seen that the CVD or PVD diamond deposited on a substrate lacks the more extensive gradient transition zone of sintered polycrystalline diamond compacts because there is no sweep of solvent-catalyst metal through the diamond table in a CVD or PVD process.

Both CVD and PVD processes achieve diamond deposition by line of sight. Means (such as vibration and rotation) are provided for exposing all desired surfaces for diamond deposition. If a vibratory stage is to be used, the bearing surface will vibrate up and down with the stage and thereby present all bearing surfaces to the free radical source.

There are several methods, which may be implemented in order to coat cylindrical objects with diamond using CVD or PVD processes. If a plasma assisted microwave process is to be used to achieve diamond deposition, then the object to receive the diamond must be directly under the plasma in order to achieve the highest quality and most uniform coating of diamond. A rotating or translational stage may be used to present every aspect of the bearing surface to the plasma for diamond coating. As the stage rotates or translates, all portions of the bearing surface may be brought directly under the plasma for coating in such a way to achieve sufficiently uniform coating.

If a hot filament CVD process is used, then the bearing surface should be placed on a stationary stage. Wires or filaments (typically tungsten) are strung over the stage so that their coverage includes the bearing surface to be coated. The distance between the filaments and the bearing surface and the distance between the filaments themselves may be chosen to achieve a uniform coating of diamond directly under the filaments.

Diamond bearing surfaces can be manufactured by CVD and PVD process either by coating a substrate with diamond or by creating a free standing volume of diamond, which is later mounted for use. A free standing volume of diamond may be created by CVD and PVD processes in a two-step operation. First, a thick film of diamond is deposited on a suitable substrate, such as silicon, molybdenum, tungsten or others. Second, the diamond film is released from the substrate.

As desired, segments of diamond film may be cut away, such as by use of a Q-switched YAG laser. Although diamond is transparent to a YAG laser, there is usually a sufficient amount of sp2 bonded carbon (as found in graphite) to allow cutting to take place. If not, then a line may be drawn on the diamond film using a carbon-based ink. The line should be sufficient to permit cutting to start, and once started, cutting will proceed slowly.

After an appropriately-sized piece of diamond has been cut from a diamond film, it can be attached to a desired object in order to serve as a bearing surface. For example, the diamond may be attached to a substrate by welding, diffusion bonding, adhesion bonding, mechanical fixation or high pressure and high temperature bonding in a press.

Although CVD and PVD diamond on a substrate do not exhibit a gradient transition zone that is found in sintered polycrystalline diamond compacts, CVD and PVD process can be conducted in order to incorporate metal into the diamond table. As mentioned elsewhere herein, incorporation of metal into the diamond table enhances adhesion of the diamond table to its substrate and can strengthen the polycrystalline diamond compact. Incorporation of diamond into the diamond table can be used to achieve a diamond table with a coefficient of thermal expansion and compressibility different from that of pure diamond, and consequently increasing fracture toughness of the diamond table as compared to pure diamond. Diamond has a low coefficient of thermal expansion and a low compressibility compared to metals. Therefore the presence of metal with diamond in the diamond table achieves a higher and more metal-like coefficient of thermal expansion and the average compressibility for the diamond table than for pure diamond. Consequently, residual stresses at the interface of the diamond table and the substrate are reduced, and delamination of the diamond table from the substrate is less likely.

A pure diamond crystal also has low fracture toughness. Therefore, in pure diamond, when a small crack is formed, the entire diamond component fails catastrophically. In comparison, metals have a high fracture toughness and can accommodate large cracks without catastrophic failure. Incorporation of metal into the diamond table achieves a greater fracture toughness than pure diamond. In a diamond table having interstitial spaces and metal within those interstitial spaces, if a crack forms in the diamond and propagates to an interstitial space containing metal, the crack will terminate at the metal and catastrophic failure will be avoided. Because of this characteristic, a diamond table with metal in its interstitial spaces is able to sustain much higher forces and workloads without catastrophic failure compared to pure diamond.

Diamond-diamond bonding tends to decrease as metal content in the diamond table increases. CVD and PVD processes can be conducted so that a transition zone is established. However, it is preferred for the bearing surface to be essentially pure polycrystalline diamond for low wear properties.

Generally CVD and PVD diamond is formed without large interstitial spaces filled with metal. Consequently, most PVD and CVD diamond is more brittle or has a lower fracture toughness than sintered polycrystalline diamond compacts. CVD and PVD diamond may also exhibit the maximum residual stresses possible between the diamond table and the substrate. It is possible, however, to form CVD and PVD diamond film that has metal incorporated into it with either a uniform or a functionally gradient composition.

One method for incorporating metal into a CVD or PVD diamond film it to use two different source materials in order to simultaneously deposit the two materials on a substrate in a CVD of PVD diamond production process. This method may be used regardless of whether diamond is being produced by CVD, PVD or a combination of the two.

Another method for incorporating metal into a CVD diamond film chemical vapor infiltration. This process would first create a porous layer of material, and then fill the pores by chemical vapor infiltration. The porous layer thickness should be approximately equal to the desired thickness for either the uniform or gradient layer. The size and distribution of the pores can be sued to control ultimate composition of the layer. Deposition in vapor infiltration occurs first at the interface between the porous layer and the substrate. As deposition continues, the interface along which the material is deposited moves outward from the substrate to fill pores in the porous layer. As the growth interface moves outward, the deposition temperature along the interface is maintained by moving the sample relative to a heater or by moving the heater relative to the growth interface. It is imperative that the porous region between the outside of the sample and the growth interface be maintained at a temperature that does not promote deposition of material (either the pore-filling material or undesired reaction products). Deposition in this region would close the pores prematurely and prevent infiltration and deposition of the desired material in inner pores. The result would be a substrate with open porosity an poor physical properties.

Another alternative manufacturing process that may be used to produce bearing surfaces and components of the invention involves use of energy beams, such as laser energy, to vaporize constituents in a substrate and redeposit those constituents on the substrate in a new form, such as in the form of a diamond coating. As an example, a metal, polymeric or other substrate may be obtained or produced containing carbon, carbides or other desired constituent elements. Appropriate energy, such as laser energy, may be directed at the substrate to cause constituent elements to move from within the substrate to the surface of the substrate adjacent the area of application of energy to the substrate. Continued application of energy to the concentrated constituent elements on the surface of the substrate can be used to cause vaporization of some of those constituent elements. The vaporized constituents may then be reacted with another element to change the properties and structure of the vaporized constituent elements.

Next, the vaporized and reacted constituent elements (which may be diamond) may be diffused into the surface of the substrate. A separate fabricated coating may be produced on the surface of the substrate having the same or a different chemical composition than that of the vaporized and reacted constituent elements. Alternatively, some of the changed constituent elements which were diffused into the substrate may be vaporized and reacted again and deposited as a coating on the. By this process and variations of it, appropriate coatings such as diamond, cubic boron nitride, diamond like carbon, B, C, SiC, TiC, TiN, TiB, cCN, $Cr_3C_2$, and $Si_3N_4$ may be formed on a substrate.

In other manufacturing environments, high temperature laser application, electroplating, sputtering, energetic laser excited plasma deposition or other methods may be used to place a volume of diamond, diamond-like material, a hard material or a superhard material in a location in which will serve as a bearing surface.

In light of the disclosure herein, those of ordinary skill in the art will comprehend the apparatuses, materials and process conditions necessary for the formation and use of high quality diamond on a substrate using any of the manufacturing methods described herein in order to create a diamond bearing surface.

F. Manufacturing the Diamond Portion of Preferred Structures

This section provides information related to manufacturing the preferred prosthetic hip joint and other structures having similar geometry.

1. The Nature of the Problem

In areas outside of prosthetic joints, in particular in the field of rock drilling cutters, polycrystalline diamond compacts have been used for some time. Historically those cutters have been cylindrical in shape with a planar diamond table at one end. The diamond surface of a cutter is much smaller than the bearing surface needed in most prosthetic joints. Thus, polycrystalline diamond cutter geometry and manufacturing methods are not directly applicable to prosthetic joints.

The particular problem posed by the manufacture of a prosthetic hip joint is how to produce a concave spherical polycrystalline diamond compact acetabular cup and a matching convex spherical polycrystalline diamond compact femoral head. In the manufacture of a spherical polycrystalline diamond compact, symmetry becomes a dominant consideration in performing loading, sealing, and pressing/sintering procedures. The spherical component design requires that pressures be applied radially in making the part. During the high pressure sintering process, described in detail below, all displacements must be along a radian emanating from the center of the sphere that will be produced in order to achieve the spherical geometry. To achieve this in high temperature/high pressure pressing, an isostatic pressure field must be created. During the manufacture of such spherical parts, if there is any deviatoric stress component, it will result in distortion of the part and may render the manufactured part useless.

Special considerations that must be taken into account in making spherical polycrystalline diamond compacts are discussed below.

a. Modulus

Most polycrystalline diamond compacts include both a diamond table and a substrate. The material properties of the diamond and the substrate may be compatible, but the high pressure and high temperature sintering process in the formation of a polycrystalline diamond compact may result in a component with excessively high residual stresses. For example, for a polycrystalline diamond compact using tungsten carbide as the substrate, the sintered diamond has a Young's modulus of approximately 120 million p.s.i., and cobalt cemented tungsten carbide has a modulus of approximately 90 million p.s.i. Modulus refers to the slope of the curve of the stress plotted against the stress for a material. Modulus indicates the stiffness of the material. Bulk modulus refers to the ratio of isostatic strain to isostatic stress, or the unit volume reduction of a material versus the applied pressure or stress.

Because diamond and most substrate materials have such a high modulus, a very small stress or displacement of the polycrystalline diamond compact can induce very large stresses. If the stresses exceed the yield strength of either the diamond or the substrate, the component will fail. The strongest polycrystalline diamond compact is not necessarily stress free. In a polycrystalline diamond compact with optimal distribution of residual stress, more energy is required to induce a fracture than in a stress free component. Thus, the difference in modulus between the substrate and the diamond must be noted and used to design a component that will have the best strength for its application with sufficient abrasion resistance and fracture toughness.

b. Coefficient of Thermal Expansion

The extent to which diamond and its substrate differ in how they deform relative to changes in temperature also affects their mechanical compatibility. Coefficient of thermal expansion ("CTE") is a measure of the unit change of a dimension with unit change in temperature or the propensity of a material to expand under heat or to contract when cooled. As a material experiences a phase change, calculations based on CTE in the initial phase will not be applicable. It is notable that when compacts of materials with different CTE's and moduluses are used, they will stress differently at the same stress.

Polycrystalline diamond has a coefficient of thermal expansion (as above and hereafter referred to as "CTE") on the order of 2–4 micro inches per inch ($10^{-6}$ inches) of material per degree ($\mu in/in° C.$). In contrast, carbide has a CTE on the order of 6–8 $\mu in/in° C$. Although these values appear to be close numerically, the influence of the high modulus creates very high residual stress fields when a temperature gradient of a few hundred degrees is imposed upon the combination of substrate and diamond. The difference in coefficient of thermal expansion is less of a problem in prior art cylindrical polycrystalline diamond compacts with a planar diamond table than in the manufacture of spherical components or components with other complex geometries for prosthetic joints. When a spherical polycrystalline diamond compact is manufactured, differences in the CTE between the diamond and the substrate can cause high residual stress with subsequent cracking and failure of the diamond table, the substrate or both at any time during or after high pressure/high temperature sintering.

c. Dilatoric and Deviatoric Stresses

The diamond and substrate assembly will experience a reduction of free volume during the sintering process. The sintering process, described in detail below, involves subjecting the substrate and diamond assembly to pressure ordinarily in the range of about 40 to about 68 kilobar. The pressure will cause volume reduction of the substrate. Some geometrical distortion of the diamond and/or the substrate may also occur. The stress that causes geometrical distortion is called deviatoric stress, and the stress that causes a change in volume is called dilatoric stress. In an isostatic system, the deviatoric stresses sum to zero and only the dilatoric stress component remains. Failure to consider all of these stress factors in designing and sintering a polycrystalline diamond component with complex geometry (such as concave and convex spherical polycrystalline diamond compacts) will likely result in failure of the process.

d. Free Volume Reduction of Diamond Feedstock

As a consequence of the physical nature of the feedstock diamond, large amounts of free volume are present unless special preparation of the feedstock is undertaken prior to sintering. It is necessary to eliminate as much of the free volume in the diamond as possible, and if the free volume present in the diamond feedstock is too great, then sintering may not occur. It is also possible to eliminate the free volume during sintering if a press with sufficient ram displacement is employed. Is important to maintain a desired uniform geometry of the diamond and substrate during any process which reduces free volume in the feedstock, or a distorted or faulty component may result.

e. Selection of Solvent-Catalyst Metal

Formation of synthetic diamond in a high temperature and high pressure press without the use of a solvent-catalyst metal is not a viable method at this time. A solvent-catalyst metal is required to achieve desired crystal formation in synthetic diamond. The solvent-catalyst metal first solvates carbon preferentially from the sharp contact points of the diamond feedstock crystals. It then recrystallizes the carbon as diamond in the interstices of the diamond matrix with diamond-diamond bonding sufficient to achieve a solid with 95 to 97% of theoretical density with solvent metal 5–3% by volume. That solid distributed over the substrate surface is referred to herein as a polycrystalline diamond table. The solvent-catalyst metal also enhances the formation of chemical bonds with substrate atoms.

When the polycrystalline diamond compact to be manufactured is intended for use in a biomedical application, it is essential to select a solvent metal which will be biocompatible. Prior art solvent-catalyst metals for polycrystalline diamond compact formation are not biocompatible, so new solvent metals which will perform satisfactorily and which are biocompatible must be found.

A preferred method for adding the solvent-catalyst metal to diamond feedstock is by causing it to sweep from the substrate that contains solvent-catalyst metal during high pressure and high temperature sintering. Powdered solvent-catalyst metal may also be added to the diamond feedstock before sintering, particularly if thicker diamond tables are desired. An attritor method may also be used to add the solvent-catalyst metal to diamond feedstock before sintering. If too much or too little solvent-catalyst metal is used, then the resulting part may lack the desired mechanical properties, so it is important to select an amount of solvent-catalyst metal and a method for adding it to diamond feedstock that is appropriate for the particular part to be manufactured.

f. Diamond Feedstock Particle Size and Distribution

The wear characteristics of the finished diamond product are integrally linked to the size of the feedstock diamond and also to the particle distribution. Selection of the proper size(s) of diamond feedstock and particle distribution depends upon the service requirement of the specimen and also its working environment. The wear resistance of polycrystalline diamond is enhanced if smaller diamond feedstock crystals are used and a highly diamond-diamond bonded diamond table is achieved.

Although polycrystalline diamond may be made from single modal diamond feedstock, use of multi-modal feedstock increases both impact strength and wear resistance. The use of a combination of large crystal sizes and small crystal sizes of diamond feedstock together provides a part with high impact strength and wear resistance, in part because the interstitial spaces between the large diamond crystals may be filled with small diamond crystals. During sintering, the small crystals will solvate and reprecipitate in a manner that binds all of the diamond crystals into a strong and tightly bonded compact.

g. Diamond Feedstock Loading Methodology

Contamination of the diamond feedstock before or during loading will cause failure of the sintering process. Great care must be taken to ensure the cleanliness of diamond feedstock and any added solvent-catalyst metal or binder before sintering.

In order to prepare for sintering, clean diamond feedstock, substrate, and container components are prepared for loading. The diamond feedstock and the substrate are placed into a refractory metal container called a "can" which will seal its contents from outside contamination. The diamond feedstock and the substrate will remain in the can while undergoing high pressure and high temperature sintering in order to form a polycrystalline diamond compact. The can will preferably be sealed by electron beam welding at high temperature and in a vacuum.

Enough diamond aggregate (powder or grit) is loaded to account for linear shrinkage during high pressure and high temperature sintering. The method used for loading diamond feedstock into a can for sintering affects the general shape and tolerances of the final part. In particular, the packing density of the feedstock diamond throughout the can should be as uniform as possible in order to produce a good quality sintered polycrystalline diamond compact structure. In loading, bridging of diamond can be avoided by staged addition and packing.

The degree of uniformity in the density of the feedstock material after loading will affect geometry of the polycrystalline diamond compact. Loading of the feedstock diamond in a dry form versus loading diamond combined with a binder and the subsequent process applied for the removal of the binder will also affect the characteristics of the finished polycrystalline diamond compact. In order to properly pre-compact diamond for sintering, the pre-compaction pressures should be applied under isostatic conditions.

h. Selection of Substrate Material

The unique material properties of diamond and its relative differences in modulus and CTE compared to most potential substrate materials diamond make selection of an appropriate polycrystalline diamond substrate a formidable task. When the additional constraints of biocompatibility is placed on the substrate, the choice is even more difficult. Most biocompatible metals are not compatible with the material properties of synthetic diamond. A great disparity in material properties between the diamond and the substrate creates challenges successful manufacture of a polycrystalline diamond component with the needed strength and durability. Even very hard substrates appear to be soft compared to polycrystalline diamond. The substrate and the diamond must be able to withstand not only the pressure and temperature of sintering, but must be able to return to room temperature and atmospheric pressure without delaminating, cracking or otherwise failing. Further, even among those materials that are believed to be biocompatible, it is expedient to use only those which meet governmental regulatory guidelines for products such as prosthetic joints.

Selection of substrate material also requires consideration of the intended application for the part, impact resistance and strengths required, and the amount of solvent-catalyst metal that will be incorporated into the diamond table during sintering. Substrate materials must be selected with material properties that are compatible with those of the diamond table to be formed.

i. Substrate Geometry

In the invention, it is preferred to manufacture spherical, hemispherical, partially spherical, arcuate and other complex concave and convex geometries of polycrystalline diamond compacts, which may later be cut, machined and otherwise finished to serve as femoral heads, acetabular cups, other joint surfaces, other bearing surfaces, and other wear-resistant surfaces. Formation of such parts requires consideration of the unique geometry of the substrate. In particular, the spherical geometry of the desired finished product requires that forces applied to the substrate and diamond feedstock during sintering be along a radian emanating from the center of the sphere to be produced.

Further, it is important to consider whether to use a substrate which has a smooth surface or a surface with topographical features. Substrate surfaces may be formed with a variety of topographical features so that the diamond table is fixed to the substrate with both a chemical bond and a mechanical grip. Use of topographical features on the substrate provides a greater surface area for chemical bonds and with the mechanical grip provided by the topographical features, can result in a stronger and more durable component.

2. Preferred Materials and Manufacturing Processes

The inventors have discovered and determined materials and manufacturing processes for constructing the preferred polycrystalline diamond compacts for use in a prosthetic joint. These materials and methods will have application outside of the field of prosthetics as well. It is also possible to manufacture the invented bearing surfaces by methods and using materials other than those listed below.

The steps described below, such as selection of substrate material and geometry, selection of diamond feedstock, loading and sintering methods, will affect each other, so although they are listed as separate steps that must be taken to manufacture a polycrystalline diamond compact, no step is completely independent of the others, and all steps must be standardized to ensure success of the manufacturing process.

a. Select Substrate Material

In order to manufacture any polycrystalline diamond component, an appropriate substrate should be selected. For the manufacture of a polycrystalline diamond component to be used in a prosthetic joint, the inventors prefer use of the substrates listed in the table below.

TABLE 2

SOME SUBSTRATES FOR BIOMEDICAL APPLICATIONS

| SUBSTRATE | ALLOY NAME | REMARKS |
|---|---|---|
| Titanium | Ti6/4 (TiAlVa) ASTM F-1313 (TiNbZr) ASTM F-620 ASTM F-1580 TiMbHf Nitinol (TiNi+other) | A thin tantalum barrier is preferably placed on the titanium substrate before loading diamond feedstock. Approved biocompatible material. |
| Cobalt chrome | ASTM F-799 | Contains cobalt, chromium and molybdenum. Wrought product. Approved biocompatible material. |
| Cobalt chrome | ASTM F-90 | Contains cobalt, chromium, tungsten and nickel. Approved biocompatible material. |
| Cobalt chrome | ASTM F-75 | Contains cobalt, chromium and molybdenum. Cast product. Approved biocompatible material. |
| Cobalt chrome | ASTM F-562 | Contains cobalt, chromium, molybdenum and nickel. Approved biocompatible material. |
| Cobalt chrome | ASTM F-563 | Contains cobalt, chromium, molybdenum, tungsten, iron and nickel. Approved biocompatible material. |
| Tantalum | ASTM F-560 (unalloyed) | Approved biocompatible refractory metal. |
| Platinum | various | |
| Niobium | ASTM F-67 (unalloyed) | Approved biocompatible refractory metal. |
| Maganese | Various | May include Cr, Ni, Mg, molybdenum. |
| Cobalt cemented tungsten carbide | WC | Not approved in the U.S. for prosthetic applications at the time of writing. |
| Cobalt chrome cemented tungsten carbide | CoCr cemented WC | CoCr is an approved biocompatible material. |
| Cobalt chrome cemented chrome carbide | CoCr cemented CrC | CoCr is an approved biocompatible material. |
| Cobalt chrome cemented silicon carbide | CoCr cemented SiC | CoCr is an approved biocompatible material. |
| Fused silicon carbide | SiC | |
| Cobalt chrome molybdenum | CoCrMo | A thin tungsten or tungsten/cobalt layer is placed on the substrate before loading diamond feedstock. |
| Stainless steel | Various | Approved biocompatible material. |

The CoCr used is preferably either CoCrMo or CoCrW. The preceding substrates are examples only. In addition to these substrates, other materials may be appropriate for use as substrates for construction of prosthetic joints and other bearing surfaces.

When titanium is used as the substrate, it is sometimes preferred by the inventors to place a thin tantalum barrier layer on the titanium substrate. The tantalum barrier prevents mixing of the titanium alloys with cobalt alloys used in the diamond feedstock. If the titanium alloys and the cobalt alloys mix, it possible that a detrimentally low melting point eutectic inter-metallic compound will be formed during the high pressure and high temperature sintering process. The tantalum barrier bonds to both the titanium and cobalt alloys, and to the polycrystalline diamond that contains cobalt solvent-catalyst metals. Thus, a polycrystalline diamond compact made using a titanium substrate with a tantalum barrier layer and diamond feedstock that has cobalt solvent-catalyst metals can be very strong and well formed. Alternatively, the titanium substrate may be provided with an alpha case oxide coating (an oxidation layer) forming a barrier which prevents formation of a eutectic metal.

If a cobalt chrome molybdenum substrate is used, it is preferred to place either a thin tungsten layer or a thin tungsten and cobalt layer on the substrate before loading of the diamond feedstock in order to control formation of chrome carbide (CrC) during sintering.

In addition to those listed, other appropriate substrates may be used for forming polycrystalline diamond compact bearing surfaces. Further, it is possible within the scope of the invention to form a diamond bearing surface for use without a substrate. It is also possible to form a bearing surface from any of the superhard materials and other bearing materials listed herein, in which case a substrate may not be needed. Additionally, if it is desired to use a type of diamond or carbon other than polycrystalline diamond, substrate selection may differ. For example, if a diamond bearing surface is to be created by use of chemical vapor deposition or physical vapor deposition, then use of a substrate appropriate for those manufacturing environments and for the compositions used will be necessary.

b. Determination of Substrate Geometry

1.) General Substrate Configuration

A substrate geometry appropriate for the compact to be manufactured and appropriate for the materials being used should be selected. In order to manufacture a concave spherical acetabular cup or a convex spherical femoral head as preferred in some embodiments of the invention, it is necessary to select a substrate geometry that will facilitate the manufacture of those parts. In order to ensure proper diamond formation and avoid compact distortion, forces acting on the diamond and the substrate during sintering must be strictly radial. Therefore the preferred substrate geometry at the contact surface with diamond feedstock for manufacturing an acetabular cup, a femoral head, or any other spherical component is generally spherical.

As mentioned previously, there is a great disparity in the material characteristics of synthetic diamond and most available substrate materials. In particular, modulus and CTE are of concern. But when applied in combination with each other, some substrates can form a stable and strong spherical polycrystalline diamond compact. The table below lists physical properties of some preferred substrate materials.

TABLE 3

MATERIAL PROPERTIES OF SOME PREFERRED SUBSTRATES

| SUBSTRATE MATERIAL | MODULUS | CTE |
|---|---|---|
| Ti 6/4 | 16.5 million psi | 5.4 |
| CoCrMo | 35.5 million psi | 16.9 |
| CoCrW | 35.3 million psi | 16.3 |

Use of either titanium or cobalt chrome substrates alone for the manufacture of spherical polycrystalline diamond compacts may result in cracking of the diamond table or separation of the substrate from the diamond table. In particular, it appears that titanium's dominant property during high pressure and high temperature sintering is compressibility while cobalt chrome's dominant property during sintering is CTE. In some embodiments of the invention, a substrate of two or more layers may be used in order to achieve dimensional stability during and after manufacturing.

Referring to the table below, some combinations of substrate materials that may be used for making spherical polycrystalline diamond compacts are listed.

TABLE 4

SPHERICAL SUBSTRATE COMBINATIONS
for Making Convex PCD Spheres

| SUBSTRATE CORE | SUBSTRATE SHELL | REMARKS |
| --- | --- | --- |
| Ti 6/4 ASTM F-136 sphere | CoCr ASTM F-799 | Alpha case oxide coating on titanium or tantalum barrier layer on titanium. |
| Ti 6/4 ASTM F-136 sphere | CoCr ASTM F-90 | Alpha case oxide coating on titanium or tantalum barrier layer on titanium. |
| CoCr ASTM F-799 sphere | Ti 6/4 ASTM F-136 | Tantalum barrier layer on titanium. |
| CoCr ASTM F-90 sphere | Ti 6/4 ASTM F-136 | Tantalum barrier layer on titanium. |
| CoCr ASTM F-799 sphere | None | Substrate surface topographical features used, as described below. |
| $Al_2O_3$ ceramic core sphere | None | |

The alpha case oxide coating is used to seal the titanium from reacting with the cobalt chrome. The tantalum barrier layer can be in the range of about 0.002 to 0.010 inches thick with 0.008 believed to be optimal.

A two piece substrate as mentioned above may be used to achieve dimensional stability in spherical parts. A two piece substrate may overcome differences in CTE and modulus between diamond and the substrate. It appears that use of a substrate with a plurality of layers overcomes the tendencies of the materials to expand and contract at different rates, which if not addressed will cause cracking of the diamond.

A spherical substrate having at least two distinct layers of different substrate materials can be employed to stabilize the component and prevent the substrate from shrinking away from the diamond table, thus resulting in the successful manufacture of spherical polycrystalline diamond compacts.

Figure 5A:
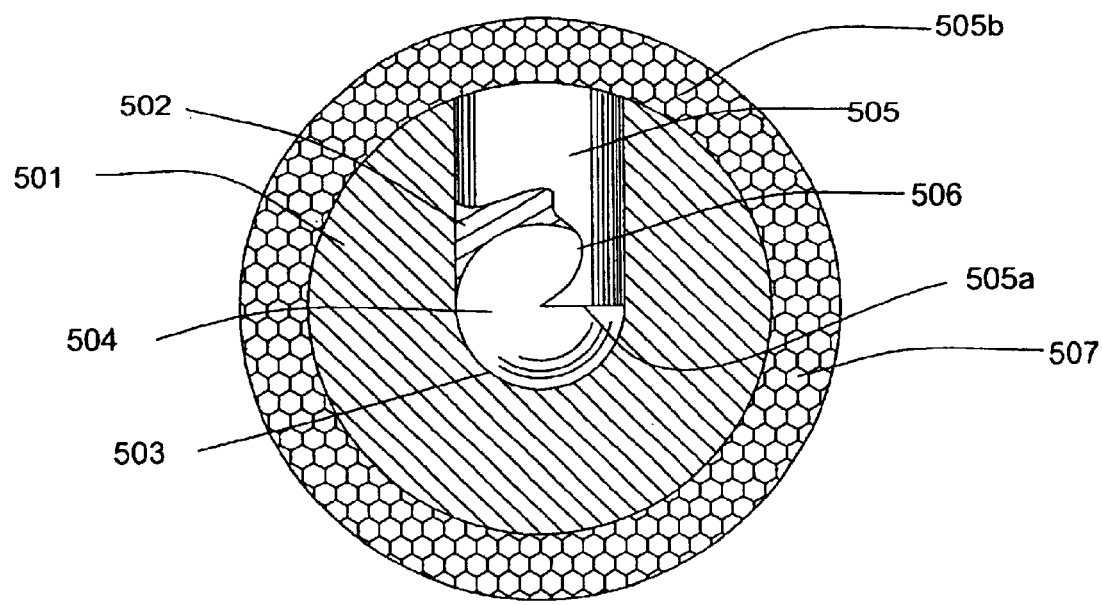
FIGS. 5A and 5B depict two-layer substrates useful for making spherical or partially spherical polycrystalline diamond compacts.
Figure 5B:
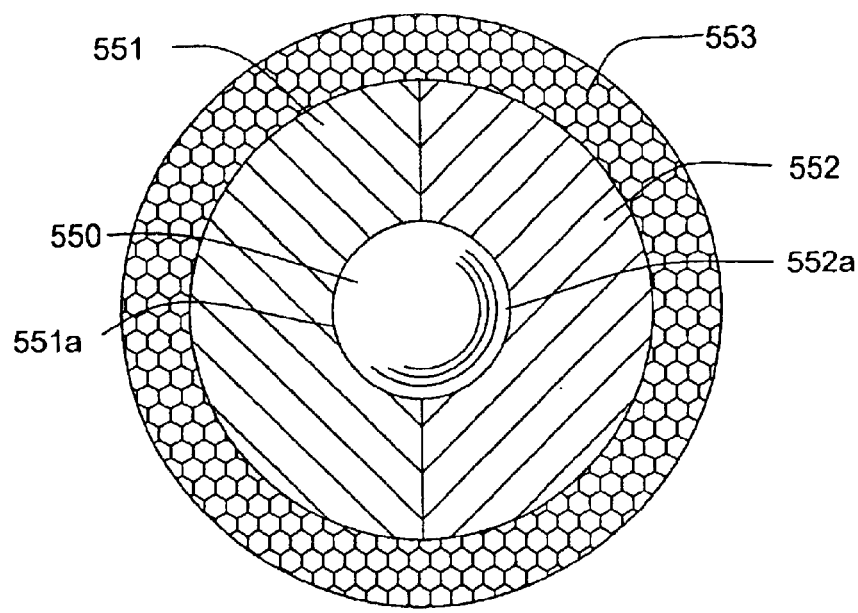

Referring to FIGS. 5A–5F, various substrate structures of the invention for making a generally spherical polycrystalline diamond compact are depicted. FIGS. 5A and 5B depict two-layer substrates.

In FIG. 5A, a solid first sphere 501 of a substrate material intended to be used as the substrate shell or outer layer was obtained. The dimensions of the first sphere 501 are such that the dimension of the first sphere 501 with a diamond table on its exterior will approximate the intended dimension of the component prior to final finishing. Once the first sphere 501 of the substrate is obtained, a hole 502 is bored into its center. The hole 502 is preferably bored, drilled, cut, blasted or otherwise formed so that the terminus 503 of the hole 502 is hemispherical. This is preferably achieved by using a drill bit or end mill with a round or ball end having the desired radius and curvature.

Then a second sphere 504 of a substrate material is obtained. The second sphere 504 is smaller than the first sphere 501 and is be placed in hole 502 in the first sphere 501. The substrates materials of spheres 501 and 504 are preferably selected form those listed in the tables above. They may also be of other appropriate materials. The second sphere 504 and the hole 502 and its terminus 503 should fit together closely without excessive tolerance or gap.

A plug 505 preferably of the same substrate material as first sphere 501 is formed or obtained. The plug 505 has a first end 505a and a second end 505b and substrate material therebetween in order to fill the hole 502 except for that portion of the hole 502 occupied by the second sphere 504 adjacent the hole terminus 503. The plug 505 preferably has a concave hemispherical receptacle 506 at its first end 505a so that plug 505 will closely abut second sphere 504 across about half the spherical surface of second sphere 504. The plug 505 is generally cylindrical in shape. The substrate assembly including one substrate sphere placed inside of another may then be loaded with diamond feedstock 507 and sintered under high pressure at high temperature to form a spherical polycrystalline diamond compact.

Referring to FIG. 5B, another substrate geometry for manufacturing spherical polycrystalline diamond compacts of the invention is depicted. An inner core sphere 550 of appropriate substrate material is selected. Then an outer substrate first hemisphere 551 and outer substrate second hemisphere 552 are selected. Each of the outer substrate first and second hemispheres 551 and 552 are formed so that they each have a hemispherical receptacle 551a and 552a shaped and sized to accommodate placement of the hemispheres about the exterior of the inner core sphere 550 and thereby enclose and encapsulate the inner core sphere 550. The substrates materials of inner core sphere 550 and hemispheres 551 and 552 are preferably selected form those listed in the tables above or other appropriate materials.

With the hemispheres and inner core sphere assembled, diamond feedstock 553 may be loaded about the exterior of the hemispheres and high temperature and high pressure sintering may proceed in order to form a spherical polycrystalline diamond compact.

Although FIGS. 5A and 5B depict two-layer substrates, it is possible to use multiple layer substrates (3 or more layers) for the manufacture of polycrystalline diamond compacts or polycrystalline cubic boron nitride compacts. The selection of a substrate material, substrate geometry, substrate surface topographical features, and substrates having a plurality of layers (2 or more layers) of the same or different materials depend at least in part on the thermo-mechanical properties of the substrate, the baro-mechanical properties of the substrate, and the baro-mechanical properties of the substrate.

Figure 5C:
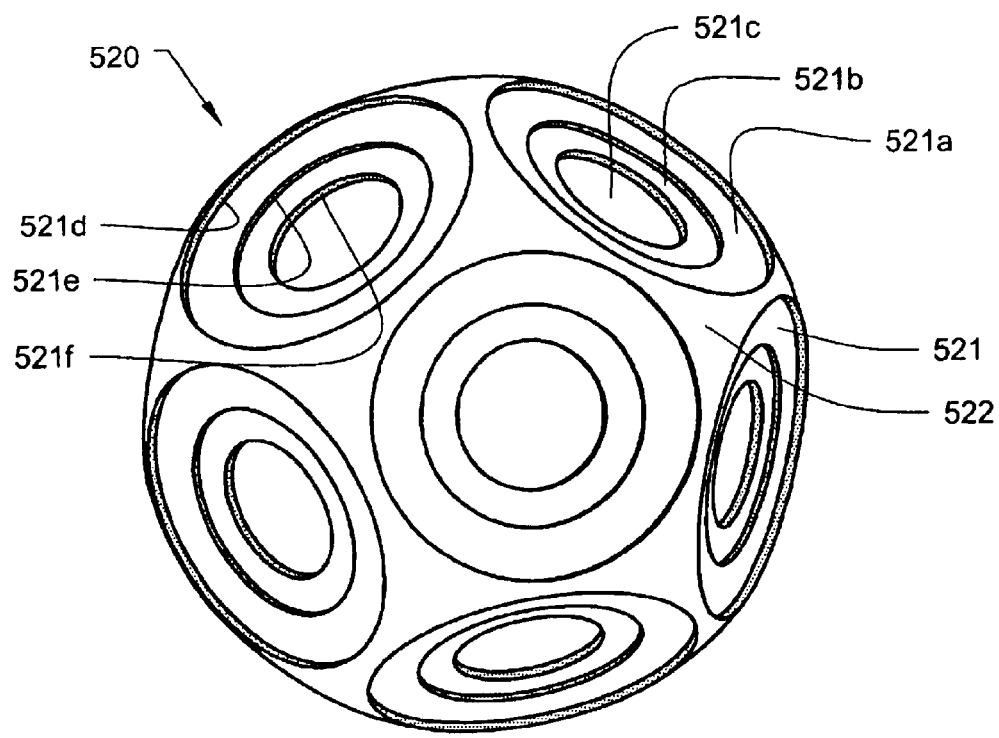
FIGS. 5C–5G depict alternative substrate configurations for making spherical or partially spherical polycrystalline diamond compacts with continuous and segmented bearing surfaces.

Referring to FIG. 5C, another substrate configuration for making generally spherical polycrystalline diamond compacts is depicted. The substrate 520 is in the general form of a sphere. The surface of the sphere includes substrate surface topography intended to enhance fixation of a diamond table to the substrate. The substrate has a plurality of depressions 521 formed on its surface. Each depression 521 is formed as three different levels of depression 521a, 521b and 521c. The depressions are depicted as being concentric circles, each of approximately the same depth, but their depths could vary, the circles need not be concentric, and the shape of the depressions need not be circular. The depression walls 521d, 521e and 521f are depicted as being parallel to a radial axis of the depressions which axis is normal to a tangent to the theoretical spherical extremity of the sphere, but could have a different orientation if desired. As depicted, the surface of the substrate sphere 522 has no topographical features other than the depressions already mentioned, but could have protrusions, depressions or other modifications as desired. The width and depth dimensions of the depressions 521 may be varied according to the polycrystalline diamond compact that is being manufactured.

Diamond feedstock may be loaded against the exterior of the substrate sphere 520 and the combination may be sintered at diamond stable pressures to produce a spherical polycrystalline diamond compact. Use of substrate surface topographical features on a generally spherical substrate provides a'superior bond between the diamond table and the substrate as described above and permits a polycrystalline diamond compact to be manufactured using a single layer substrate. That is because of the gripping action between the substrate and the diamond table achieved by use of substrate surface topographical features.

Figure 5D:
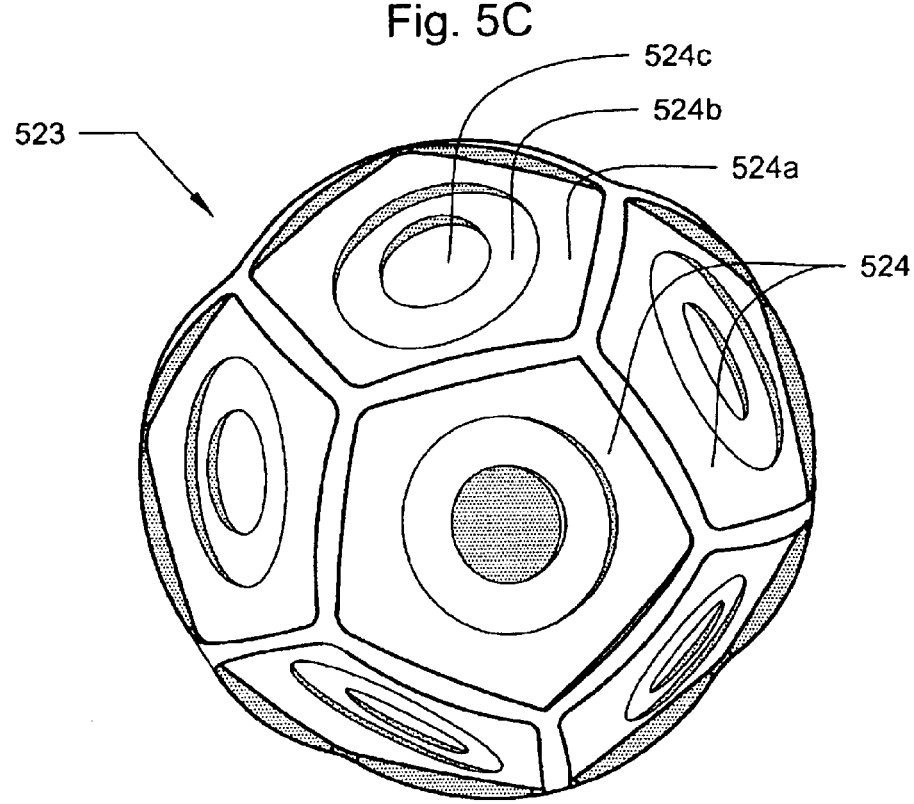

Referring to FIG. 5D, a segmented spherical substrate 523 is depicted. The substrate has a plurality of surface depressions 524 equally spaced about its exterior surface. These depressions as depicted are formed in levels of three different depths. The first level 524a is formed to a predetermined depth and is of pentagonal shape about its outer periphery. The second level 524b is round in shape and is formed to a predetermined depth which may be different from the predetermined depth of the pentagon. The third level 524c is round in shape in is formed to a predetermined depth which may be different from each of the other depths mentioned above. Alternatively, the depressions may be formed to only one depth, may all be pentagonal, or may be a mixture of shapes. The depressions may be formed by machining the substrate sphere.

Figure 5E:
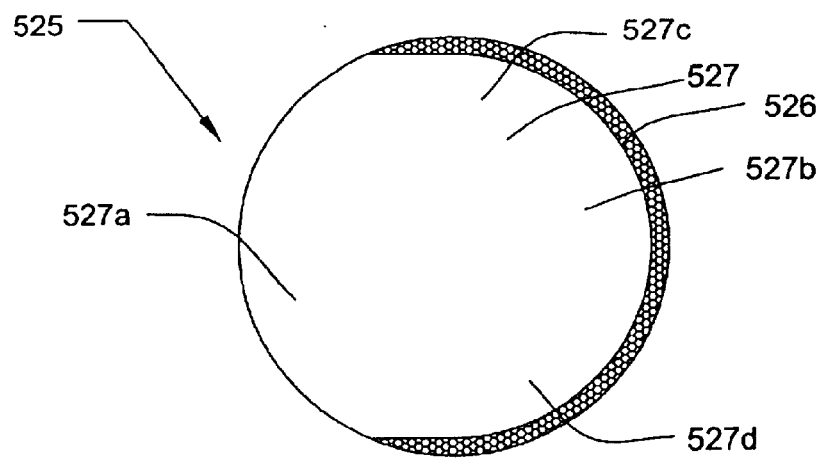

Referring to FIG. 5E, a cross section of an alternative substrate configuration for making a polycrystalline diamond compact is shown. A polycrystalline diamond compact 525 is shown. The compact 525 is spherical. The compact 525 includes a diamond table 526 sintered to a substrate 527. The substrate is partially spherical in shape at its distal side 527a and is dome-shaped on its proximal side 527b. Alternatively, the proximal side 527b of the substrate 527 may be described as being partially spherical, but the sphere on which it is based has a radius of smaller dimension than the radius of the sphere on which the distal side 527a of the substrate is based. Each of the top 527c and bottom 527d are formed in a shape convenient to transition from the proximal side 527b substrate partial sphere to the distal side 527a substrate partial sphere. This substrate configuration has advantages in that it leaves a portion of substrate exposed for drilling and attaching fixation components without disturbing residual stress fields of the polycrystalline diamond table. It also provides a portion of the substrate that does not have diamond sintered to it, allowing dilatation of the substrate during sintering without disruption of the diamond table. More than 180 degrees of the exterior of the substrate sphere has diamond on it, however, so the part is useful as a femoral head or other articulation surface.

Figure 5F:
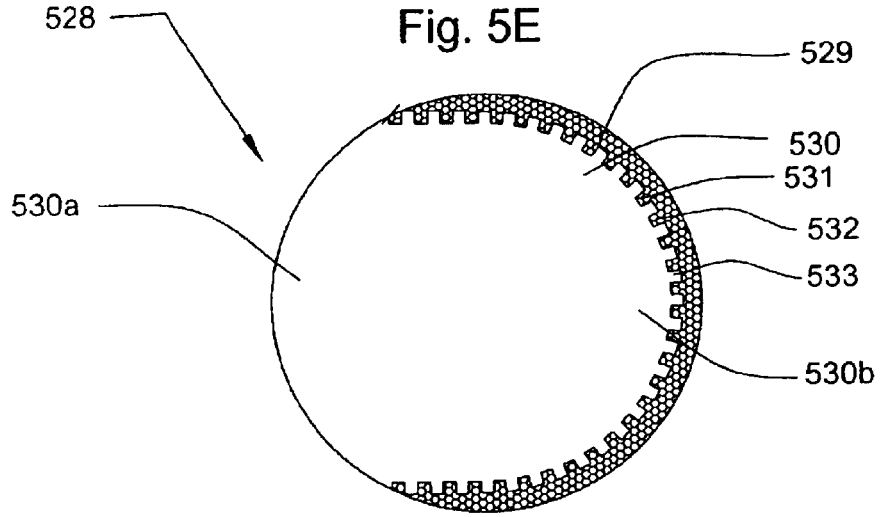

Referring to FIG. 5F, a cross section of an alternative substrate configuration for making a polycrystalline diamond compact is shown. A polycrystalline diamond compact 528 is depicted having a diamond table 529 and a substrate 530. The substrate has topographical features 531 for enhancing strength of the diamond to substrate interface. The topographical features may include rectangular protrusions 532 spaced apart by depressions 533 or corridors. The distal side of the substrate is formed based on a sphere of radius r. The proximal side of the substrate 530b is formed based on a sphere of radius r', where r>r'. Usually the surface modifications will be found beneath substantially all of the diamond table.

Figure 5G:
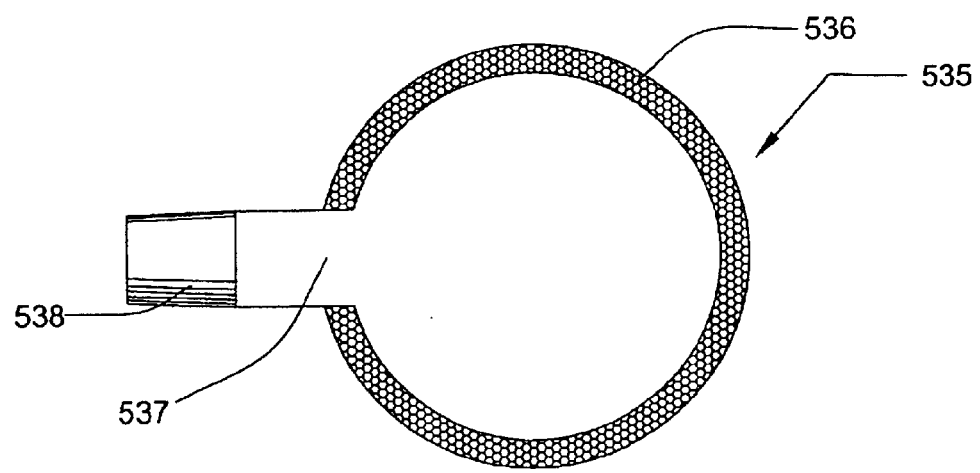

Referring to FIG. 5G, a femoral head 535 of a prosthetic hip joint is depicted. The femoral head 535 that includes a diamond table 536 sintered to a substrate 536. The substrate is configured as a sphere with a protruding cylindrical shape. The head 535 is formed so that a quantity of substrate protrudes from the spherical shape of the head to form a neck 538 which may be attached to an appropriate body by any known attachment method, such as by self-locking taper fit, welding, threads or other attachment mechanisms. The use of a neck 538 preformed on the substrate that is used to manufacture a polycrystalline diamond compact 535 provides an attachment point on the polycrystalline diamond compact that may be utilized without disturbing the residual stress field of the compact. The neck 538 depicted is an integral component of a stem 540.

Any of the previously mentioned substrate configurations and substrate topographies and variations and derivatives of them may be used to manufacture a polycrystalline diamond compact for use in a prosthetic or other load bearing or articulation surface environment.

In various embodiments of the invention, a single layer substrate may be utilized. In other embodiments of the invention, a two-layer substrate may be utilized, as discussed. Depending on the properties of the components being used, however, it may be desired to utilize a substrate that includes three, four or more layers. Such multi-layer substrates are intended to be comprehended within the scope of the invention.

Figure 6A:
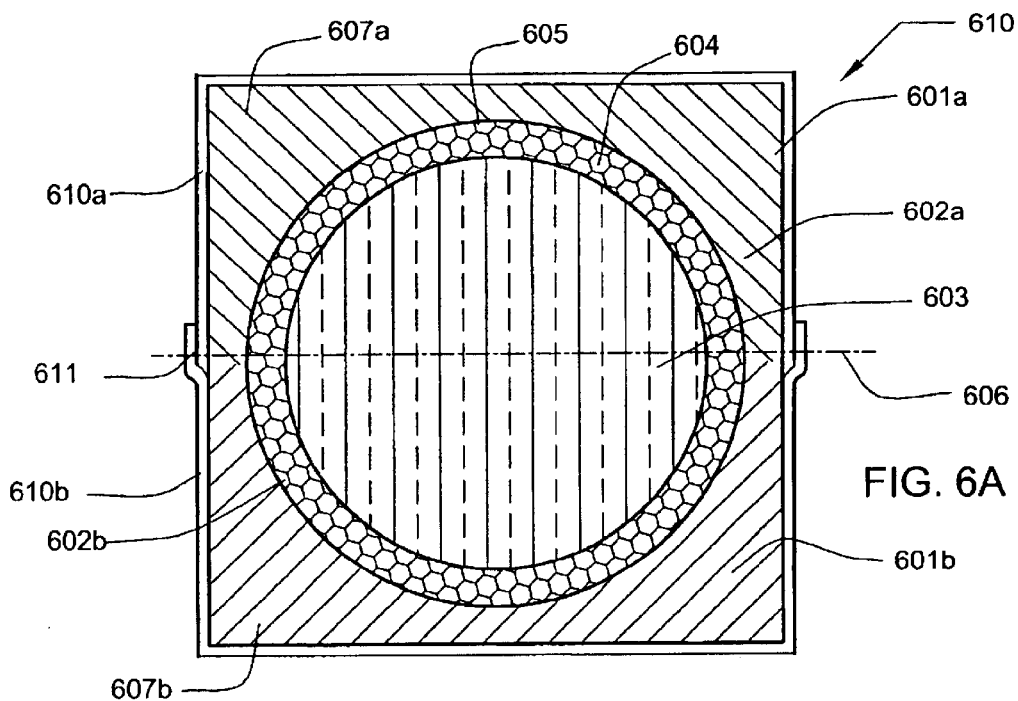
FIG. 6A depicts an assembly useful for making a convex spherical polycrystalline diamond compact.
Figure 6B:
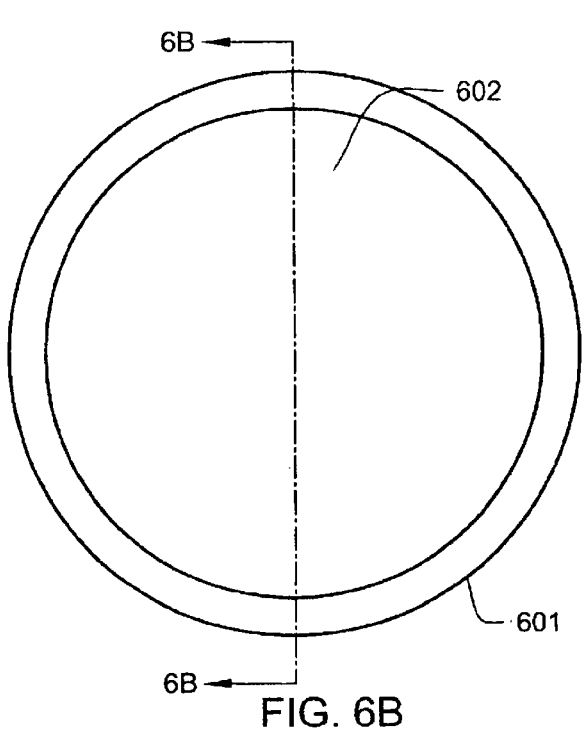
FIGS. 6B and 6C depict a substrate useful for making concave spherical polycrystalline diamond compacts.
Figure 6C:
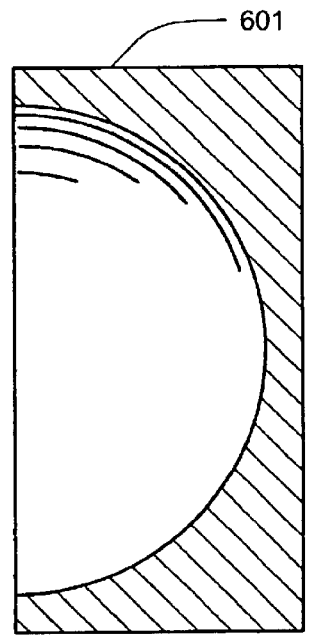

The preferred substrate geometry for manufacturing an acetabular cup or other concave spherical, hemispherical or partially spherical polycrystalline diamond compact of the invention differs from that used to manufacture a convex spherical polycrystalline diamond compact. Referring to FIGS. 6A–6C below, the preferred substrate geometry and assembly for manufacturing a concave spherical polycrystalline diamond compact (such as that used in an acetabular cup) are depicted. The substrate 601 (and 601a and 601b) is preferably in the form of a cylinder with a hemispherical receptacle 602 (and 602a and 602b) formed into one of its ends.

Two substrate cylinders 601a and 601b are placed so that their hemispherical receptacles 602a and 602b are adjacent each other, thus forming a spherical cavity 604 between them. A sphere 603 of an appropriate substrate material is located in the cavity 604. Diamond feedstock 605 is located in the cavity 604 between the exterior of the sphere 603 and the concave surfaces of the receptacles 602a and 602b of the substrate cylinders 601a and 601b. The assembly is placed into a refractory metal can 610 for sintering. The can has a first cylinder 610a and a second cylinder 601b. The two cylinders join at a lip 611.

After such an assembly is sintered, the assembly may be slit, cut or ground along the center line 606 in order to form a first cup assembly 607a and a second cup assembly 607b. The preferred substrate materials for the cylinders 602a and 602b are CoCrMo (ASTM F-799) and CoCrW (ASTM F-90), and the preferred substrate material for the sphere 603 is preferably CoCrMo (ASTM F-799), although any appropriate substrate material may be used, including some of those listed in the tables.

While two layer substrates have been discussed above for manufacturing concave and convex spherical polycrystalline diamond compacts, it is also possible to use substrates consisting of more than two layers of material or substrates of a single type of material in manufacturing spherical polycrystalline diamond compacts.

2.) Substrate Surface Topography

Depending on the application; it may be advantageous to include substrate surface topographical features on a substrate that is to be formed into a polycrystalline diamond compact. Regardless whether a one-piece, a two-piece of a multi-piece substrate is used, it may be desirable to modify the surface of the substrate or provide topographical features on the substrate in order to increase the total surface area of diamond to enhance substrate to diamond contact and to provide a mechanical grip of the diamond table.

The placement of topographical features on a substrate serves to modify the substrate surface geometry or contours from what the substrate surface geometry or contours would be if formed as a simple planar or non-planar figure. Substrate surface topographical features may include one or more different types of topographical features which result in protruding, indented or contoured features that serve to increase surface, mechanically interlock the diamond table to the substrate, prevent crack formation, or prevent crack propagation.

Substrate surface topographical features or substrate surface modifications serve a variety of useful functions. Use of substrate topographical features increases total substrate surface area of contact between the substrate and the diamond table. This increased surface area of contact between diamond table and substrate results in a greater total number of chemical bonds between diamond table and substrate than if the substrate surface topographical features were absent, thus achieving a stronger polycrystalline diamond compact.

Substrate surface topographical features also serve to create a mechanical interlock between the substrate and the diamond table. The mechanical interlock is achieved by the nature of the substrate topographical features and also enhances strength of the polycrystalline diamond compact.

Substrate surface topographical features may also be used to distribute the residual stress field of the polycrystalline diamond compact over a larger surface area and over a larger volume of diamond and substrate material. This greater distribution can be used to keep stresses below the threshold for crack initiation and/or crack propagation at the diamond table/substrate interface, within the diamond itself and within the substrate itself.

Substrate surface topographical features increase the depth of the gradient interface or transition zone between diamond table and substrate, in order to distribute the residual stress field through a longer segment of the composite compact structure and to achieve a stronger part.

Substrate surface modifications can be used to created a sintered polycrystalline diamond compact that has residual stresses that fortify the strength of the diamond layer and yield a more robust polycrystalline diamond compact with greater resistance to breakage than if no surface topographical features were used. This is because in order to break the diamond layer, it is necessary to first overcome the residual stresses in the part and then overcome the strength of the diamond table.

Substrate surface topographical features redistribute forces received by the diamond table. Substrate surface topographical features cause a force transmitted through the diamond layer to be re-transmitted from single force vector along multiple force vectors. This redistribution of forces travelling to the substrate avoids conditions that would deform the substrate material at a more rapid rate than the diamond table, as such differences in deformation can cause cracking and failure of the diamond table.

Substrate surface topographical features may be used to mitigate the intensity of the stress field between the diamond and the substrate in order to achieve a stronger part.

Substrate surface topographical features may be used to distribute the residual stress field throughout the polycrystalline diamond compact structure in order to reduce the stress per unit volume of structure.

Substrate surface topographical features may be used to mechanically interlock the diamond table to the substrate by causing the substrate to compress over an edge of the diamond table during manufacturing. Dovetailed, hemispherical and lentate modifications act to provide force vectors that tend to compress and enhance the interface of diamond table and substrate during cooling as the substrate dilitates radially.

Substrate surface topographical features may also be used to achieve a manufacturable form. As mentioned herein, differences in coefficient of thermal expansion and modulus between diamond and the chosen substrate may result in failure of the polycrystalline diamond compact during manufacturing. For certain parts, the stronger interface between substrate and diamond table that may be achieved when substrate topographical features are used can achieve a polycrystalline diamond compact that can be successfully manufactured. But if a similar part of the same dimensions is to be made using a substrate with a simple substrate surface rather than specialized substrate surface topographical features, the diamond table may crack or separate from the substrate due to differences in coefficient of thermal expansion or modulus of the diamond and the substrate.

Examples of useful substrate surface topographical features include waves, grooves, ridges, other longitudinal surface features (any of which may be arranged longitudinally, lattitudinally, crossing each other at a desired angle, in random patterns, and in geometric patterns), three dimensional textures, spherical segment depressions, spherical segment protrusions, triangular depressions, triangular protrusions, arcuate depressions, arcuate protrusions, partially spherical depressions, partially spherical protrusions, cylindrical depressions, cylindrical protrusions, rectangular depressions, rectangular protrusions, depressions of n-sided polygonal shapes where n is an integer, protrusions of n-sided polygonal shapes, a waffle pattern of ridges, a waffle iron pattern of protruding structures, dimples, nipples, protrusions, ribs, fenestrations, grooves, troughs or ridges that have a cross-sectional shape that is rounded, triangular, arcuate, square, polygonal, curved, or otherwise, or other shapes. Machining, pressing, extrusion, punching, injection molding and other manufacturing techniques for creating such forms may be used to achieve desired substrate topography. Although for illustration purposes, some sharp corners are depicted on substrate topography or other structures in the drawings, in practice it is expected that all corners will have a small radius to achieve a component with superior durability.

Figure 3D:
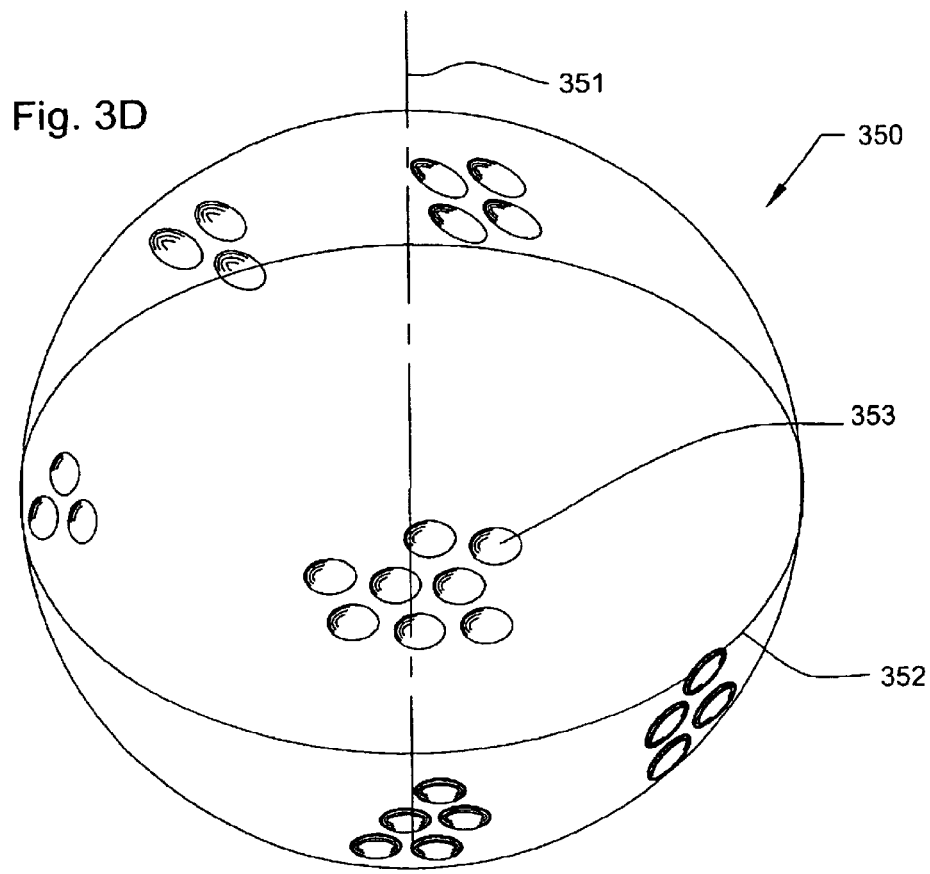
FIGS. 3A–3U depict substrate surface topographical features desirable in some embodiments of the invention.
Figure 3H:
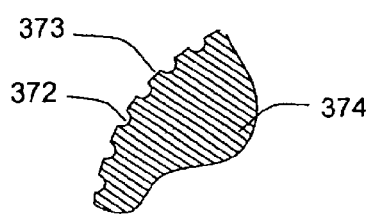
Figure 3E:
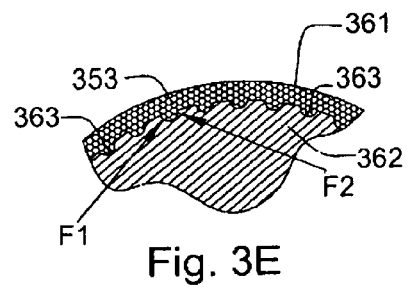
Figure 3F:
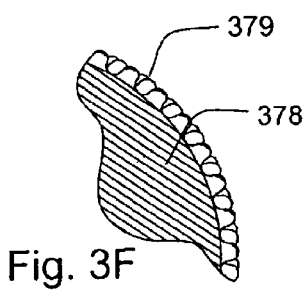
Figure 3G:
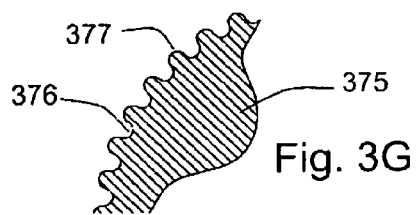
Figure 3:
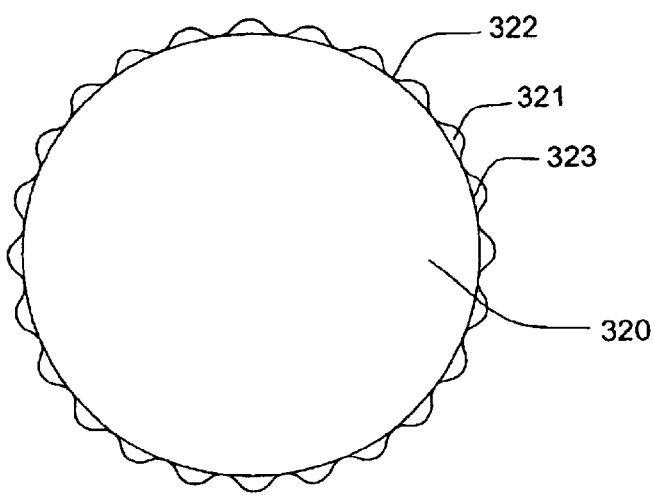
Figure 3J:
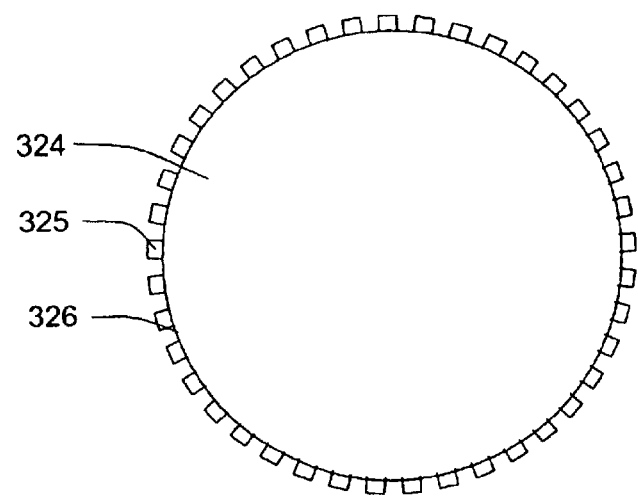
Figure 3K:
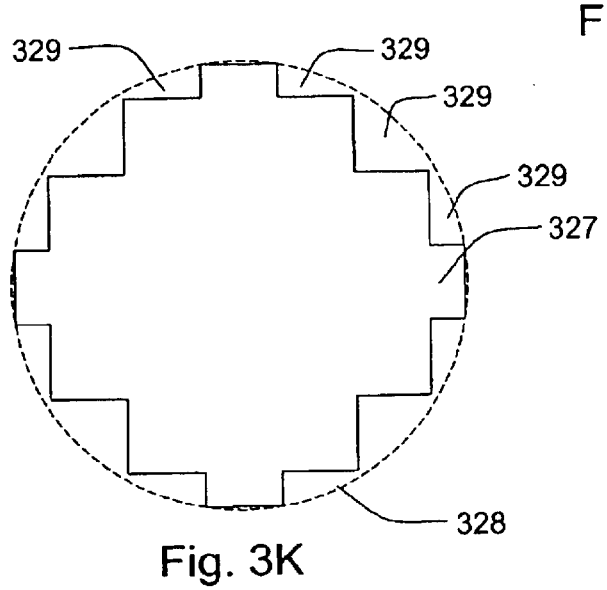
Figure 3L:
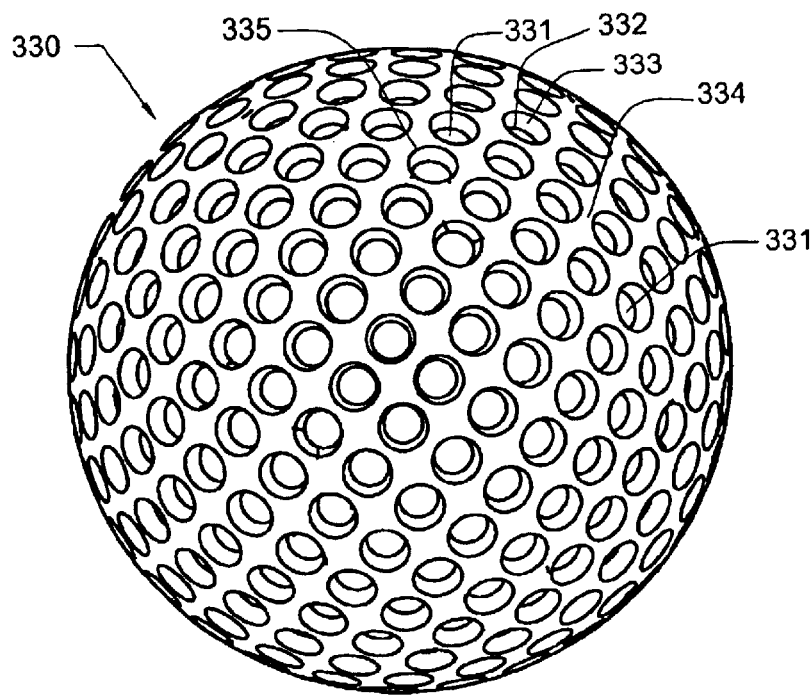
Figure 3M:
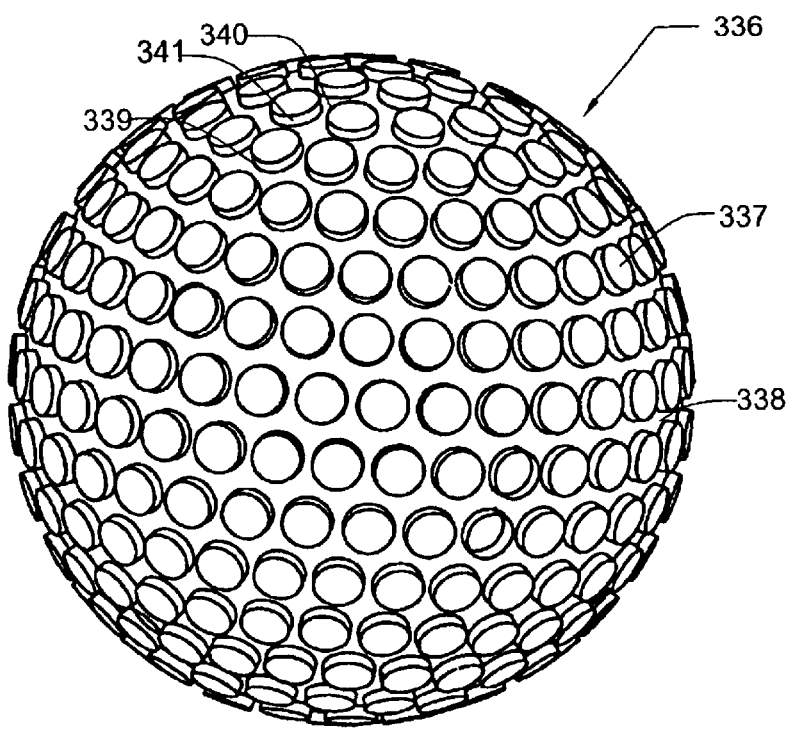
Figure 3N:
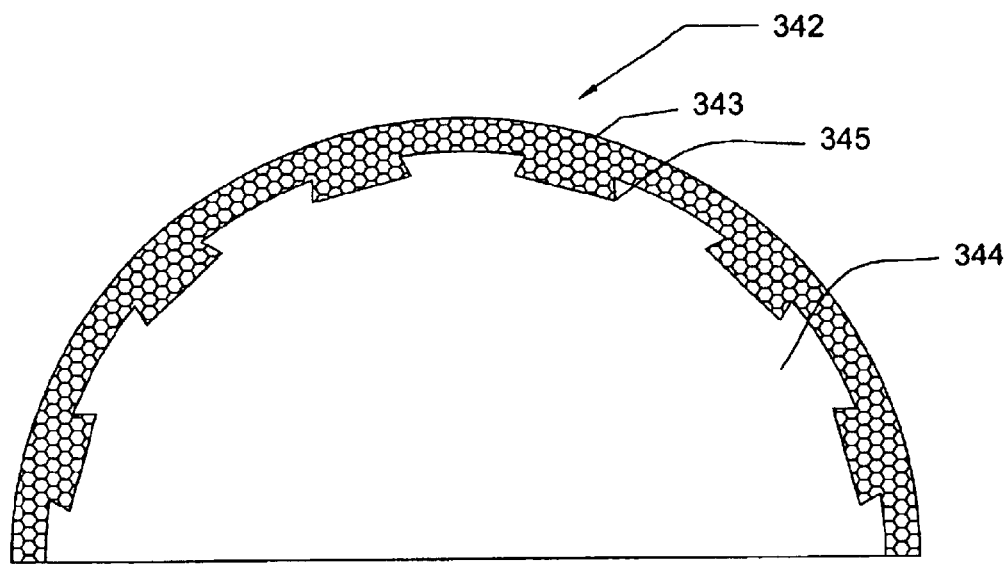
Figure 3:
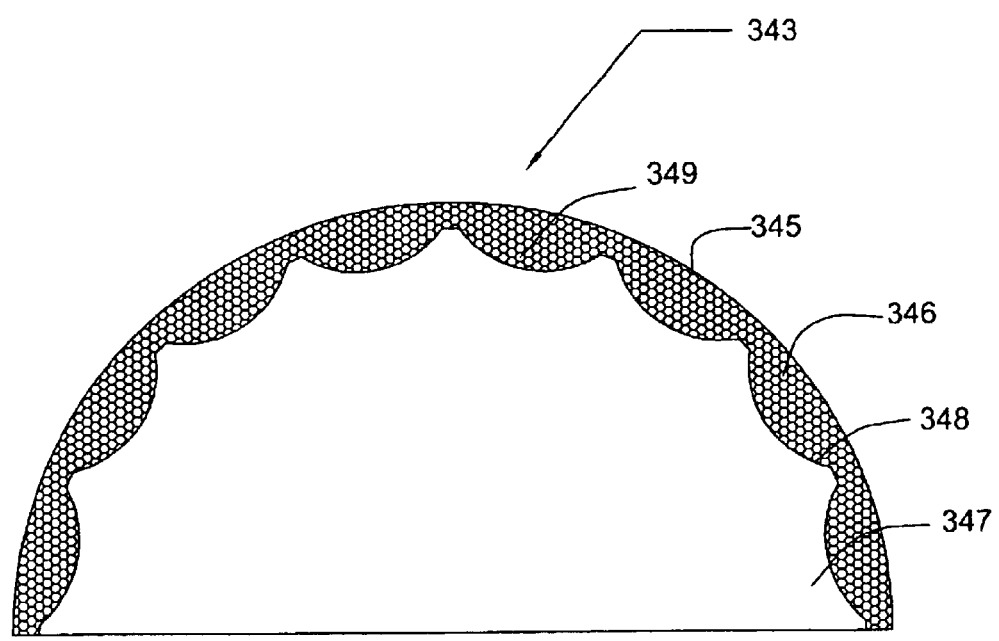
Figure 3P:
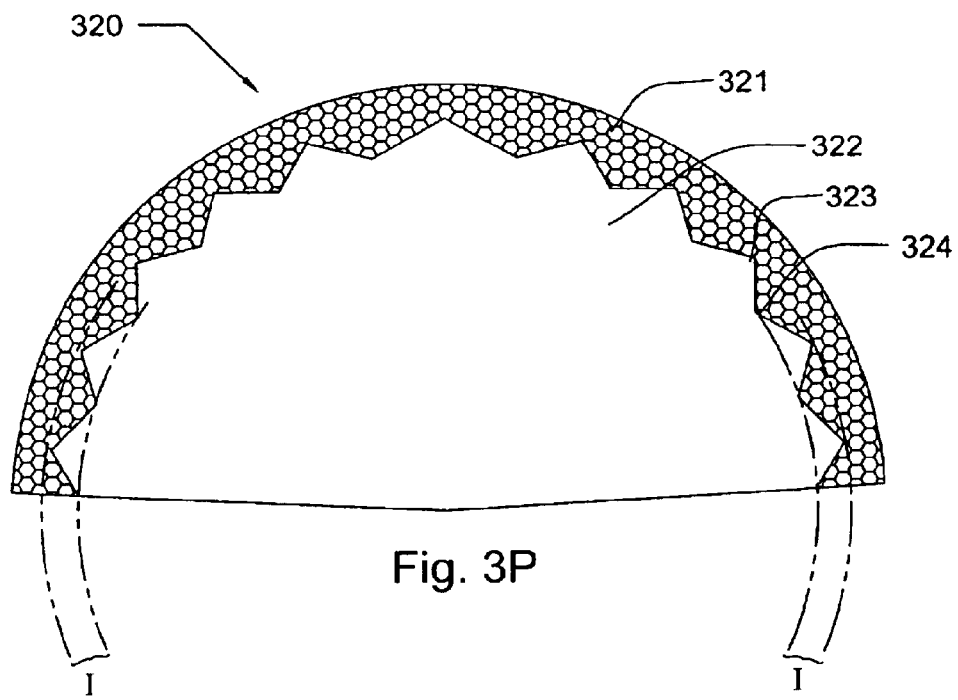
Figure 3Q:
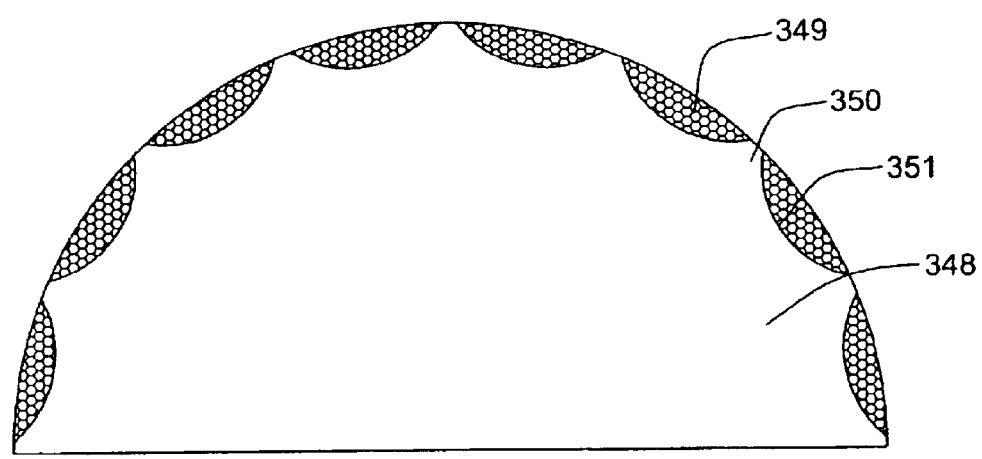
Figure 3R:
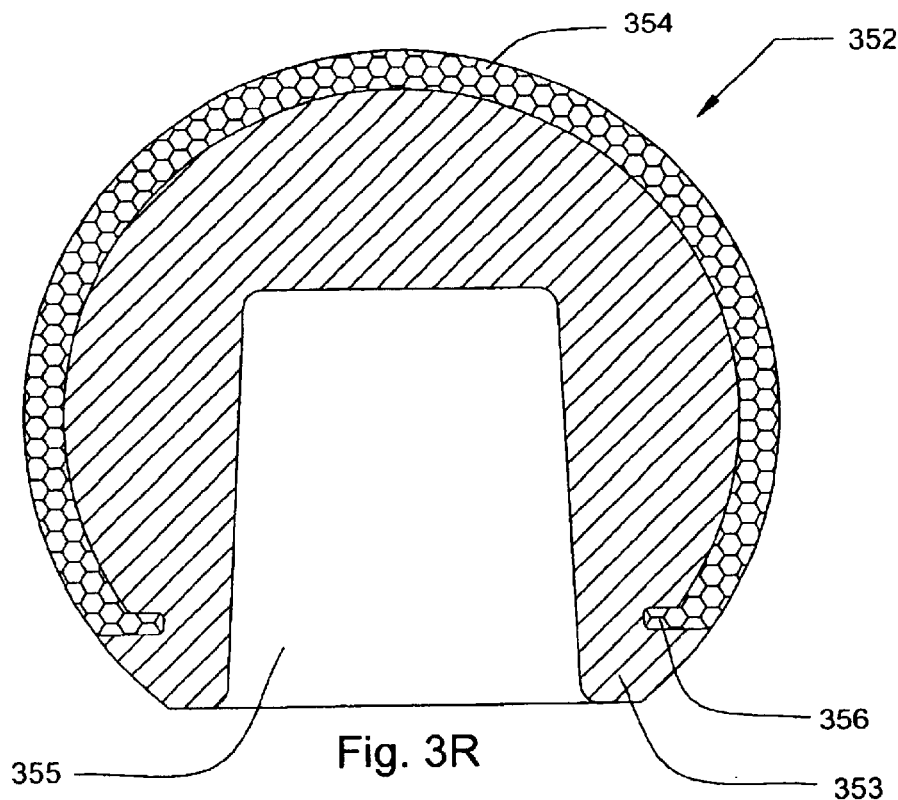
Figure 3S:
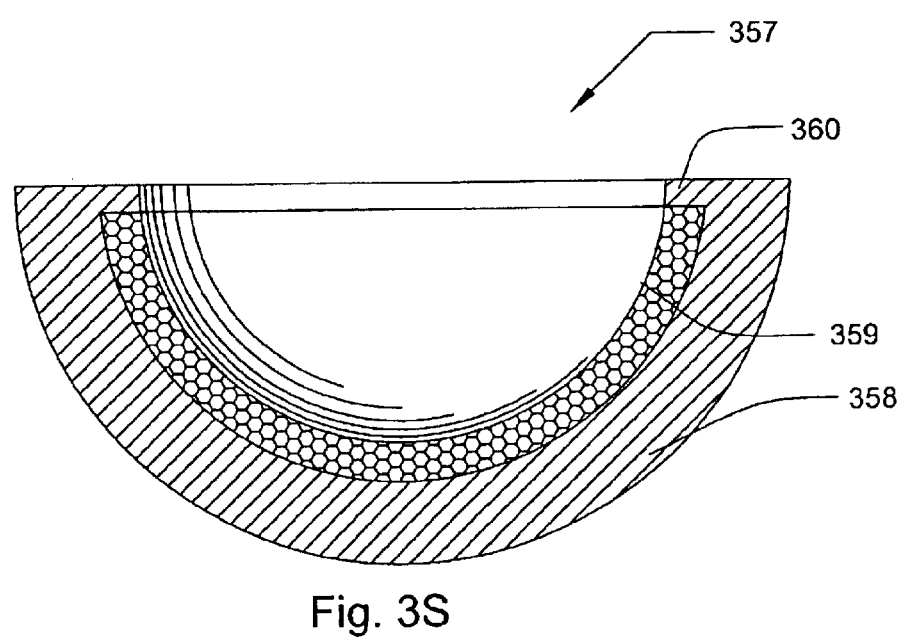
Figure 3T:
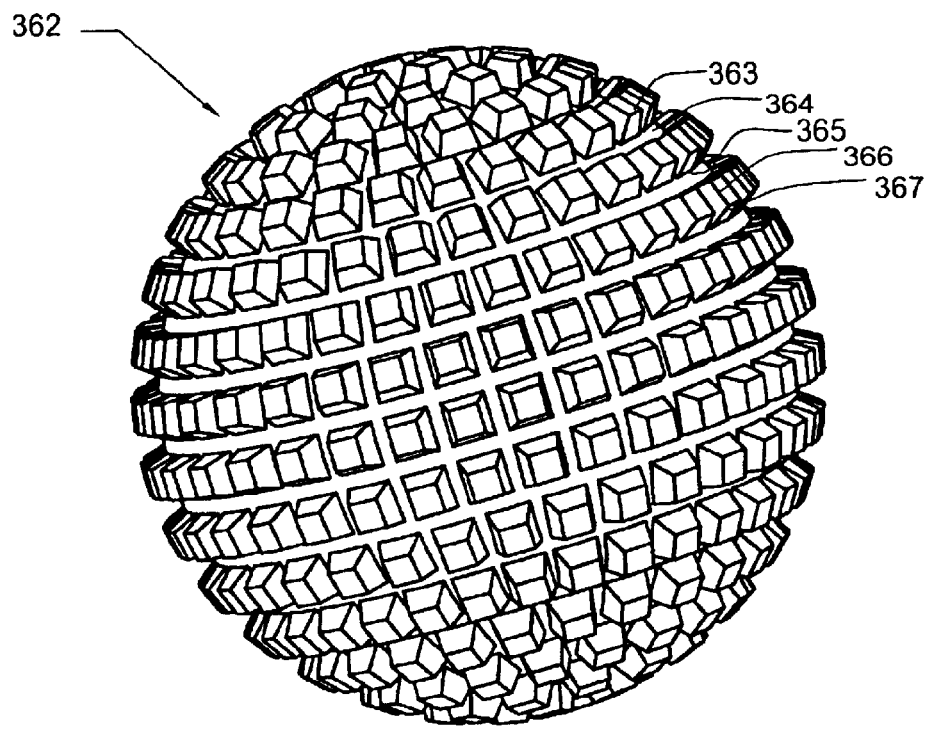
Figure 3U:
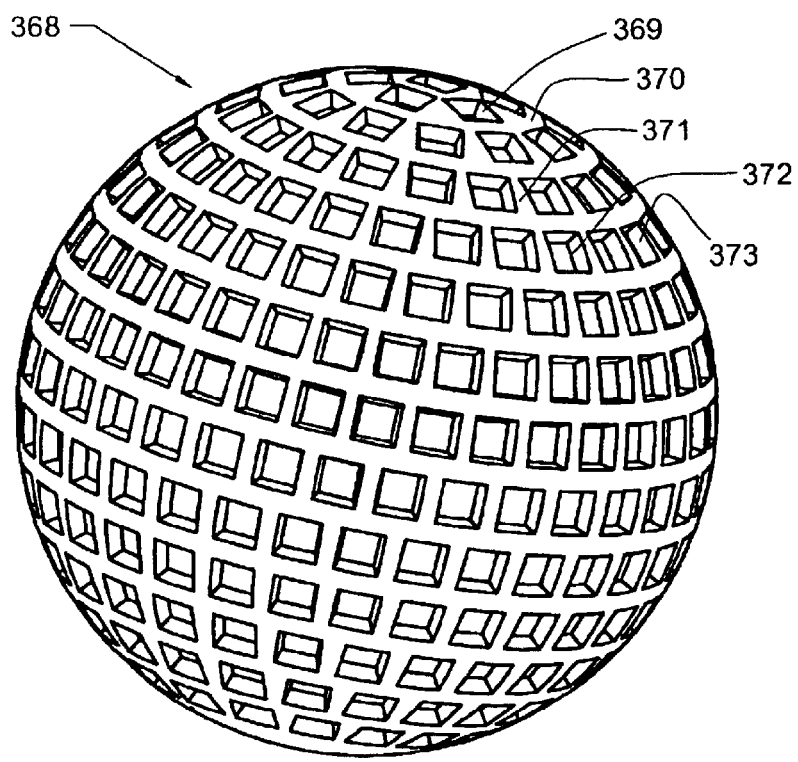

FIGS. 3A–3U depict a few possible substrate surface modifications. Referring to FIG. 3A, a femoral head is depicted that features concave and convex substrate surface topographical features. A femoral head 380 is shown that has a diamond table 382 sintered to a substrate 383. The substrate 383 has surface topography that includes concave arcuate grooves 384 and convex arcuate ridges 385 radiating from a point on the substrate. The diamond 382 covers the substrate topographical features, resulting in a greater surface area of contact between the diamond table and the substrate than if a simple rounded substrate were employed.

FIG. 3B shows redistribution of a force applied to the femoral head 380 of FIG. 3A. When a force F1 is applied to the head 380, that force F1 is redistributed along force vectors F2 and F3, as shown. Thus, although on the diamond table 382 a single force vector is received, that force vector is broken down into smaller forces and transmitted through the substrate 383. This redistribution of forces decreases the possibility of a differential in rates of deformation of the diamond table and the substrate and therefore reduces the chance of the diamond table cracking and failing.

FIG. 3C depicts use of substrate topographical features on a femoral head in a prosthetic joint. The acetabular cup 386 is mounted in the pelvic bone 387. The cup 386 has a polycrystalline diamond table 388 attached to a substrate 389. The femoral head 390 includes a table of polycrystalline diamond 391 on a substrate 392.

The substrate 392 has surface topography including grooves 393 oriented so that they will be generally vertical when the joint is in standing use in a patient. The primary force vector F1 is generally parallel to the grooves 393 in a standing position. The force zone 394 due to walking is shown in bone above the cup. Use of substrate surface topography that includes grooves that are generally vertically oriented in a standing patient achieves wider redistribution of forces.

FIG. 3D depicts a convex sphere 350 of appropriate substrate material. The sphere 350 has a polar axis 351 and an equator 352. A plurality of surface modifications 353 were formed in the surface of the sphere 350. The surface modifications are arranged in a close offset configuration. The surface modifications can range from less than about 0.001 inch to more than about 0.750 inch diameter cylindrical depressions having a depth of from less than about 0.001 inch to more than about 0.750 inch or otherwise as desired. Very small surface topographical features can be created by use of a laser. In most embodiments of the invention, substrate surface topographical features will cover from about 1% to about 99% of the surface of the substrate beneath the diamond table. The substrate surface topographical features will have a depth of from about 1% of the radius of the part to about 50% of the radius of the part. Discrete substrate surface topographical features will have a dimension measured along a tangent to the substrate surface of from about 1% to about 50% of the radius of the part.

FIG. 3E depicts a cross section of a polycrystalline diamond compact formed using a spherical substrate with a modified substrate surface, such as that depicted in FIG. 3A. The compact 360 has a diamond layer 361 sintered to a substrate 362. The substrate 362 has surface modifications 363 in which diamond 361 is found. The substrate in the vicinity of the surface modification 363 tends to grip the diamond at force lines F1 and F2, thus adding a mechanical gripping advantage to the chemical bonds of the polycrystalline diamond compact, and resulting in a very strong part.

FIG. 3F depicts substrate surface convex rounded protrusions 379 or nipples on a substrate 378. The nipples or protrusions are depicted as being rounded or arcuate. FIG. 3G depicts substrate surface protruding ridges 377 and grooves 376 on a substrate 375. FIG. 3H depicts a substrate 374 having elevated ridges 273 and rounded or arcuate grooves 372 between the ridges. This substrate surface configuration may be made by machining grooves that are round in cross section in a spherical substrate. The ridges 377 are substrate material left between the grooves that have been machined.

FIG. 3I depicts a convex spherical substrate 320. Absent specialized substrate surface topographical features, the substrate 320 would be in the form of a simple sphere as depicted by circle 323. This substrate 320 includes rounded or arcuate wavelike forms on its exterior surface that take the shape of protruding ridges 322 and depressed grooves 321.

FIG. 3J depicts a convex spherical substrate 324. The substrate 324 includes protruding rectangular forms 325 which form a waffle-like pattern on the surface of the substrate 324. Between each protruding form 325 is a gap, groove, trough, or alley 326.

FIG. 3K depicts a substrate 327. Such a substrate may have been simple convex spherical as indicated by dashed circle 328, but has been machined to have its present form. The substrate 327 has had polygonal shapes 329 formed into its surface to create specialized topographical features for an interface with a diamond table.

FIG. 3L depicts a generally spherical substrate 330 having a plurality of depressions 331 formed in its surface. The surface 334 of the substrate sphere 330 is spherical in shape except for the depressions 331. The depressions have a circular upper rim 335, a circular bottom 332, and a sidewall 333 of a desired depth. As desired, the maximum diameter of the rim 335 of a depression may have the same or greater dimension than the maximum diameter of the bottom 332 of the same depression. If the two diameters are the same, then the depression will have a cylindrical shape. If the rim 335 has a greater diameter than the bottom 333, then the depression will have a frusto-conical shape. Diamond may be bonded on a substrate as depicted in FIG. 3L in table that has a thickness that completely covers the outside surface of the substrate. In that case, the diamond table will be thicker in areas above a depression than in other areas. If such a diamond table is used, then from outward appearance, the substrate surface topographical features will not be discernible. Alternatively, diamond may be bonded in the depressions only, leaving the substrate between depressions exposed. Such a configuration is discussed in more detail with respect to FIG. 3Q.

FIG. 3M depicts a generally spherical substrate 336 having a plurality of protrusions 337 on its surface. The surface 338 of the substrate sphere 336 is spherical in shape except for the protrusions 337. The protrusions have a circular lower rim 339, a circular upper rim 340, and a sidewall 341 of a desired height. The protrusion tops 342 may be of any desired shape, such as flat, domed, partially spherical, arcuate, or otherwise. As desired, the maximum diameter of the lower rim 339 and the upper rim 340 may differ. If the two diameters are the same and the sidewall 341 is straight, then the protrusion will have a generally cylindrical shape. If the rim 339 has a greater diameter than the rim 340, then the protrusion will have a generally frusto-conical shape. A diamond table may be attached to the substrate of FIG. 3M to that the diamond table completely covers the substrate surface modifications and the areas between them. In such a configuration, from outward appearance the substrate surface modifications would not be discernible. Alternatively, diamond may be attached to the substrate only between the substrate surface modifications, creating a web or network of exposed diamond having discontinuous areas of exposed substrate material.

FIG. 3N depicts a spherical polycrystalline diamond compact 342 including a diamond table 343 and a substrate 344. The substrate 344 includes topographical surface modifications. The surface modifications include dovetail depressions 345 formed in the substrate. Polycrystalline diamond has formed in the dovetail to create a tight mechanical interlock between the diamond table and the substrate. This structure may be achieved by forming depressions in the surface of a substrate that do not have a dovetail shape. During sintering, the dovetail interlock between the substrate and the diamond table can be formed due to differences in the coefficient of thermal expansion and modulus between diamond and the substrate material.

FIG. 3O depicts a partially spherical polycrystal line diamond compact 345 having a diamond table 346 and a substrate 347. The diamond table 346 presents a continuous diamond load bearing and articulation surface. The substrate 347 has been formed with surface topography intended to effect a stronger bond with the diamond table. The substrate 347 includes hemispherical or lentate modifications 348 formed on the substrate outer surface. The modifications depicted are concave partially spherical depressions on the substrate surface. Polycrystalline diamond forms in the depressions 349. During sintering, as the polycrystalline diamond compact cools, the substrate tends to dilatate radially. The hemispherical depressions of this surface modification provide force vectors that compress and enhance the interface between the diamond table and the substrate, to achieve a much stronger bond between the diamond table and the substrate. Thus, a mechanical grip or interlock is created between the diamond table and the substrate both as a result of the differences in CTE between the diamond and the substrate and as a result of the substrate topographical features.

FIG. 3P depicts a partially spherical polycrystalline diamond compact 320. The compact 320 includes a diamond table 321 and a substrate 322. The substrate 322 has topographical features that include ridges 323 and troughs 324 that are triangular in cross section. The use of substrate topographical features such as these provides a gradient interface or transition zone between the diamond and the substrate as described elsewhere herein. The gradient interface I found in a polycrystalline diamond compact that has substrate topographical features is typically of greater depth than that found in a polycrystalline diamond compact that has a substrate with a simple surface. Consequently, the residual stress field in a polycrystalline diamond compact that has substrate topographical features is distributed through a longer segment of the composite compact structure, and is distributed over a greater volume of diamond and substrate materials. The result is a polycrystalline diamond compact that is stronger and more stable than that which may be achieved without the use of substrate topographical features.

FIG. 3Q depicts a partially spherical polycrystalline diamond compact. The compact includes a substrate 348 formed with diamond receptacles, depressions or indentations 351. On sintering, polycrystalline diamond 349 is formed in the depressions 351 in order to create a load bearing and articulation surface that includes discontinuous or segmented areas of diamond. Between the diamond areas 349, there is exposed substrate material 350 on the load bearing and articulation surface. During finish polishing, the lesser hardness of the substrate material compared to diamond will tend to cause the exposed substrate 350 to be relieved, presenting a load bearing and articulation surface on which the primary contact and articulation is provided by the diamond patches 349. If desired, the exposed substrate 350 may be machined or polished to provide sufficient relief to serve as a channel for communicating lubricating fluids to the load bearing and articulation surface.

FIG. 3R depicts a spherical ball 352 that has a substrate 353 and a diamond table 354. The substrate 353 includes a receptacle 355 for receiving an attachment mechanism. The diamond table 354 covers less than the entire surface of the substrate 353. As depicted, the diamond table 354 has a hemispherical configuration. The substrate 353 has been prepared with an annular groove or ring 356 about its equator. The diamond table 354 is thicker in the area of the annular groove 356 and occupies the annular groove 356 in order to provide strong bonding at the edge of the diamond table 354.

FIG. 3S depicts a cup 357 having a substrate 358 and a diamond table load bearing and articulation surface 359. The substrate 358 includes a lip 360 which interlocks the diamond table 359 in place in the cup 357. Although the lip 360 structure may be formed in the substrate 358 prior to sintering of the polycrystalline diamond compact, the lip 360 structure may also be formed or enhanced by dilatation of the substrate material during sintering. The lip reduces or eliminates edge effect at the extreme radial interface of the diamond table 359 and the substrate 358 in order to provide a stronger and more durable component.

FIG. 3T depicts a generally spherical substrate 362 having a plurality of truncated pyramid-like or polygonal protrusions 363 on its surface. The surface 364 of the substrate sphere 362 is generally spherical in shape except for the protrusions 363. The protrusions have a square or rectangular lower perimeter 365, a square or rectangular upper perimeter 366 and a side wall 37 of desired height. The protrusion tops 366 may differ to form a plurality of different angles between the lower and upper perimeters. If the two perimeters are the same dimension and the sidewall 367 is straight, then the protrusions will have a generally square or rectangular shape. If the upper perimeter 366 has a smaller dimension than the lower perimeter, then the protrusion will have a generally truncated pyramid shape. If the upper perimeter 366 is larger than the lower perimeter 365, the protrusion will have a generally inverted truncated pyramid shape. A diamond table may attach to the substrate of FIG. 3T so that the diamond table completely covers the substrate surface modifications and the areas between them. In such a configuration, from outward appearance, the substrate surface modifications would not be discernable. Alternatively, diamond may be attached to the substrate only between the substrate surface modifications, creating a web or network of exposed diamond having discontinuous areas of exposed substrate material.

FIG. 3U depicts a generally spherical substrate 368 having a plurality of depressions 369 formed into its surface. The surface 370 of the substrate sphere 368 is spherical in shape except for the depressions 369. The depressions have a square or rectangular upper perimeter 37, a square or rectangular bottom 372, and a sidewall 373 of a desired depth. As desired, the maximum upper perimeter 371 of a depression may have the same dimension of the bottom perimeter 372 of the same depression. If the perimeters are the same, then the depression will have a rectangular square shape. If the upper perimeter 371 has a greater dimension than the bottom perimeter 352, then the depression will have an inverted truncated pyramid shape. Diamond may be bonded on a substrate as depicted in FIG. 3U in a table that has a thickness that completely covers the outside surface of the substrate. In that case the diamond table will be thicker in areas above a depression than in other areas. If such a diamond table is used, then from outward appearance, the substrate surface topographical features will not be discernible. Alternatively, diamond may be bonded in the depressions only, leaving the substrate between depressions exposed.

Although many substrate topographies have been depicted in convex spherical substrates, those surface topographies may be applied to convex spherical substrate surfaces, other non-planar substrate surfaces, and flat substrate surfaces. Substrate surface topographies which are variations or modifications of those shown, and other substrate topographies which increase component strength or durability may also be used.

C. Diamond Feedstock Selection

It is anticipated that typically the diamond particles used will be in the range of less than 1 micron to more than 100 microns. In some embodiments of the invention, however, diamond particles as small as 1 nanometer may be used. Smaller diamond particles are preferred for smoother bearing surfaces. Commonly, diamond particle sizes will be in the range of 0.5 to 2.0 microns or 0.1 to 10 microns.

A preferred diamond feedstock is shown in the table below.

TABLE 3

EXAMPLE BIMODAL DIAMOND FEEDSTOCK

| MATERIAL | AMOUNT |
| --- | --- |
| 4 to 8 micron diamond | about 90% |
| 0.5 to 1.0 micron diamond | about 9% |
| Titanium carbonitride powder | about 1% |

This formulation mixes some smaller and some larger diamond crystals so that during sintering, the small crystals may dissolve and then recrystallize in order to form a lattice structure with the larger diamond crystals. Titanium carbonitride powder may optionally be included in the diamond feedstock in order to prevent excessive diamond grain growth during sintering in order to produce a finished product that has smaller diamond crystals.

Another diamond feedstock example is provided in the table below.

TABLE 4

EXAMPLE TRIIMODAL DIAMOND FEEDSTOCK

| MATERIAL | AMOUNT |
| --- | --- |
| Size x diamond crystals | about 90% |
| Size 0.1 x diamond crystals | about 9% |
| Size 0.01 x diamond crystals | about 1% |

The trimodal diamond feedstock described above can be used with any suitable diamond feedstock having a first size or diameter "x", a second size 0.1x and a third size 0.01x. This ratio of diamond crystals allows packing of the feedstock to about 89% theoretical density, closing most interstitial spaces and providing the densest diamond table in the finished polycrystalline diamond compact.

Another diamond feedstock example is provided in the table below.

TABLE 5

EXAMPLE TRIIMODAL DIAMOND FEEDSTOCK

| MATERIAL | AMOUNT |
| --- | --- |
| Size x diamond crystals | about 88–92% |
| Size 0.1 x diamond crystals | about 8–12% |
| Size 0.01 x diamond crystals | about 0.8–1.2% |

Another diamond feedstock example is provided in the table below.

TABLE 6

EXAMPLE TRIIMODAL DIAMOND FEEDSTOCK

| MATERIAL | AMOUNT |
| --- | --- |
| Size x diamond crystals | about 85–95% |
| Size 0.1 x diamond crystals | about 5–15% |
| Size 0.01 x diamond crystals | about 0.5–1.5% |

Another diamond feedstock example is provided in the table below.

TABLE 7

EXAMPLE TRIIMODAL DIAMOND FEEDSTOCK

| MATERIAL | AMOUNT |
| --- | --- |
| Size x diamond crystals | about 80–90% |
| Size 0.1 x diamond crystals | about 10–20% |
| Size 0.01 x diamond crystals | about 0–2% |

In some embodiments of the invention, the diamond feedstock used will be diamond powder having a greatest dimension of about 100 nanometers or less. In some embodiments of the invention it is preferred to include some solvent-catalyst metal with the diamond feedstock to aid in the sintering process, although in many applications there will be a significant solvent catalyst metal sweep from the substrate during sintering as well.

d. Solvent Metal Selection

It has already been mentioned that solvent metal will sweep from the substrate through the diamond feedstock during sintering in order to solvate some diamond crystals so that they may later recrystallize and form a diamond-diamond bonded lattice network that characterizes polycrystalline diamond. It is preferred, however, to include some solvent-catalyst metal in the diamond feedstock only when required to supplement the jet sweep of solvent-catalyst metal from the substrate.

Traditionally, cobalt, nickel and iron have been used as solvent metals for making polycrystalline diamond. In prosthetic joints, however, the solvent metal must be biocompatible. The inventors prefer use of a solvent metal such as CoCrMo or CoCrW. Platinum and other materials could also be used for a binder.

It is important not just to add the solvent metal to diamond feedstock, but also to include solvent metal in an appropriate proportion and to mix it evenly with the feedstock. The inventors prefer the use of about 86% diamond feedstock and 15% solvent metal by mass (weight), but anticipate that useful ratios of diamond feedstock to solvent metal will include 5:95, 10:90, 20:80, 30:70, 40:60, 50:50, 60:40, 65:35, 75:25, 80:20, 90:10, 95:5, 97:3, 98:2, 99:1, 99.5:0.5, 99.7:0.3, 99.8:0.2, 99.9:0.1 and others.

In order to mix the diamond feedstock with solvent-catalyst metal, first the amounts of feedstock and solvent metal to be mixed may be placed together in a mixing bowl, such as a mixing bowl made of the desired solvent-catalyst metal. Then the combination of feedstock and solvent metal may be mixed at an appropriate speed (such as 200 rpm) with dry methanol and attritor balls for an appropriate time period, such as 30 minutes. The attritor balls, the mixing fixture and the mixing bowl are preferably made from the solvent-catalyst metal. The methanol may then be decanted and the diamond feedstock separated from the attritor balls. The feedstock may then be dried and cleaned by firing in a molecular hydrogen furnace at about 1000 degrees Celsius for about 1 hour. The feedstock is then ready for loading and sintering. Alternatively, it may be stored in conditions which will preserve its cleanliness. Appropriate furnaces which may be used for firing also include hydrogen plasma furnaces and vacuum furnaces.

e. Loading Diamond Feedstock

The loading technique for diamond feedstock used is critical to the success of the final product. As mentioned previously, the diamond feedstock must be loaded to uniform density in order to produce a component that lacks unwanted distortion.

Figure 7:
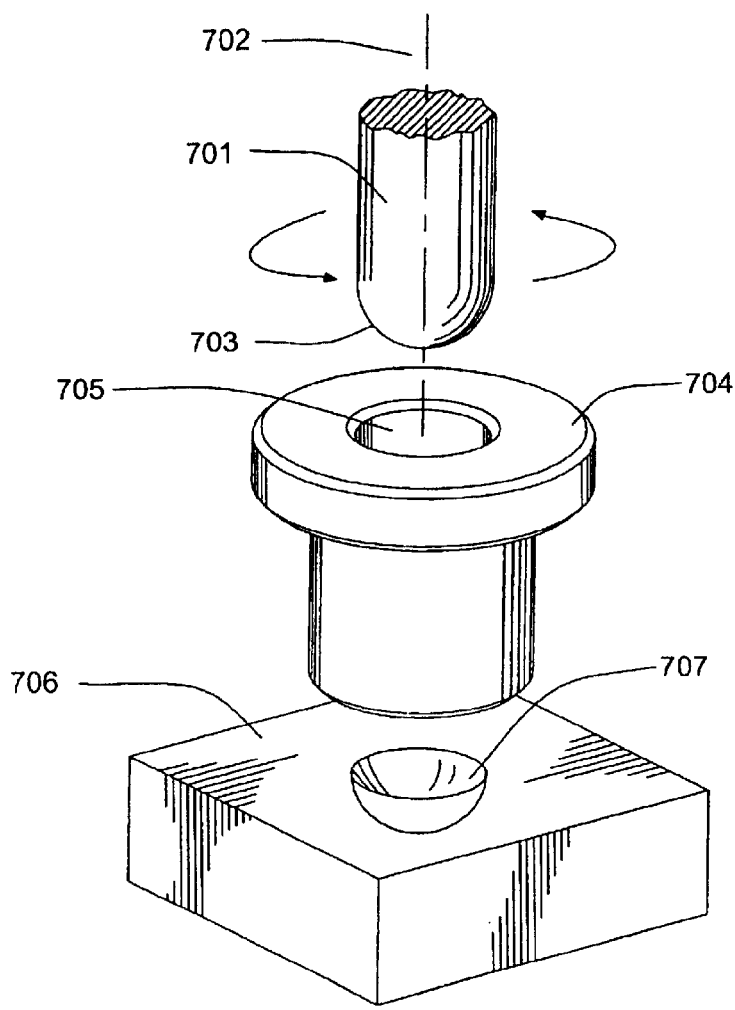
FIG. 7 depicts a device, which may be used for loading diamond feedstock prior to sintering.

Referring to FIG. 7, an apparatus for carrying out a preferred loading technique is depicted. The apparatus includes a spinning rod 701 with a longitudinal axis 702, the spinning rod being capable of spinning about its longitudinal axis. The spinning rod 701 has an end 703 matched to the size and shape of the part to be manufactured. For example, if the part to be manufactured is a femoral head or an acetabular cup, the spinning rod end 703 should be hemispherical.

A compression ring 704 is provided with a bore 705 through which the spinning rod 701 may project. A die 706 or can is provided with a cavity 707 also matched to the size and shape of the part to be made.

In order to load diamond feedstock, the spinning rod is placed into a drill chuck and the spinning rod is aligned with the center point of the die. The depth to which the spinning rod stops in relation to the cavity of the die is controlled with a set screw and monitored with a dial indicator.

The die is charged with a known amount of diamond feedstock material. The spinning rod is then spun about its longitudinal axis and lowered into the die cavity to a predetermined depth. The spinning rod contacts and rearranges the diamond feedstock during this operation. Then the spinning of the spinning rod is stopped and the spinning rod is locked in place.

The compression ring is then lowered around the outside of the spinning rod to a point where the compression ring contacts diamond feedstock in the cavity of the die. The part of the compression ring that contacts the diamond is annular. The compression ring is tamped up and down to compact the diamond. This type of compaction is used to distribute diamond material throughout the cavity to the same density and may be done in stages to prevent bridging. Packing the diamond with the compaction ring causes the density of the diamond around the equator of the sample caused to be very uniform and the same as that of the polar region in the cavity. In this configuration, the diamond sinters in a truly spherical fashion and the resulting part maintains its sphericity to close tolerances.

Another method which may be employed to maintain a uniform density of the feedstock diamond is the use of a binder. A binder is added to the correct volume of feedstock diamond, and then the combination is pressed into a can. Some binders which might be used include polyvinyl butyryl, polymethyl methacrylate, polyvinyl formol, polyvinyl chloride acetate, polyethylene, ethyl cellulose, methylabietate, paraffin wax, polypropylene carbonate and polyethyl methacrylate.

In a preferred embodiment of the invention, the process of binding diamond feedstock includes four steps. First, a binder solution is prepared. A binder solution may be prepared by adding about 5 to 25% plasticizer to pellets of poly(propylene carbonate), and dissolving this mixture in solvent such as 2-butanone to make about a 20% solution by weight.

Plasticizers that may be used include nonaqueous binders generally, glycol, dibutyl phthalate, benzyl butyl phthalate, alkyl benzyl phthalate, diethylhexyl phthalate, diisoecyl phthalate, diisononyl phthalate, dimethyl phthalate, dipropylene glycol dibenzoate, mixed glycols dibenzoate, 2-ethylhexyl diphenyl dibenzoate, mixed glycols dibenzoate, 2-ethylhexyl diphenyl phosphate, isodecyl diphenyl phosphate, isodecyl diphenl phosphate, tricrestyl phosphate, tributoxy ethyl phosphate, dihexyl adipate, triisooctyl trimellitate, dioctyl phthalate, epoxidized linseed oil, epoxidized soybean oil, acetyl triethyl citrate, propylene carbonate, various phthalate esters, butyl stearate, glycerin, polyalkyl glycol derivatives, diethyl oxalate, paraffin wax and triethylene glycol. Other appropriate plasticizers may be used as well.

Solvents that may be used include 2-butanone, methylene chloride, chloroform, 1,2-dichloroethne, trichlorethylene, methyl acetate, ethyl acetate, vinyl acetate, propylene carbonate, n-propyl acetate, acetonitrile, dimethylformamide, propionitrile, n-mehyl-2-pyrrolidene, glacial acetic acid, dimethyl sulfoxide, acetone, methyl ethyl ketone, cyclohexanone, oxysolve 80a, caprotactone, butyrolactone, tetrahydrofuran, 1,4 dioxane, propylene oxide, cellosolve acetate, 2-methoxy ethyl ether, benzene, styrene, xylene, ethanol, methanol, toluene, cyclohexane, chlorinated hydrocarbons, esters, ketones, ethers, ethyl benzene and various hydrocarbons. Other appropriate solvents may be used as well.

Second, diamond is mixed with the binder solution. Diamond may be added to the binder solution to achieve about a 2–25% binder solution (the percentage is calculated without regard to the 2-butanone).

Third, the mixture of diamond and binder solution is dried. This may be accomplished by placing the diamond and binder solution mixture in a vacuum oven for about 24 hours at about 50 degrees Celsius in order to drive out all of the solvent 2-butanone. Fourth, the diamond and binder may be pressed into shape. When the diamond and binder is removed from the oven, it will be in a clump that may be broken into pieces which are then pressed into the desired shape with a compaction press. A pressing spindle of the desired geometry may be contacted with the bound diamond to form it into a desired shape. When the diamond and binder have been pressed, the spindle is retracted. The preferred final density of diamond and binder after pressing is at least about 2.6 grams per cubic centimeter.

Figure 7A:
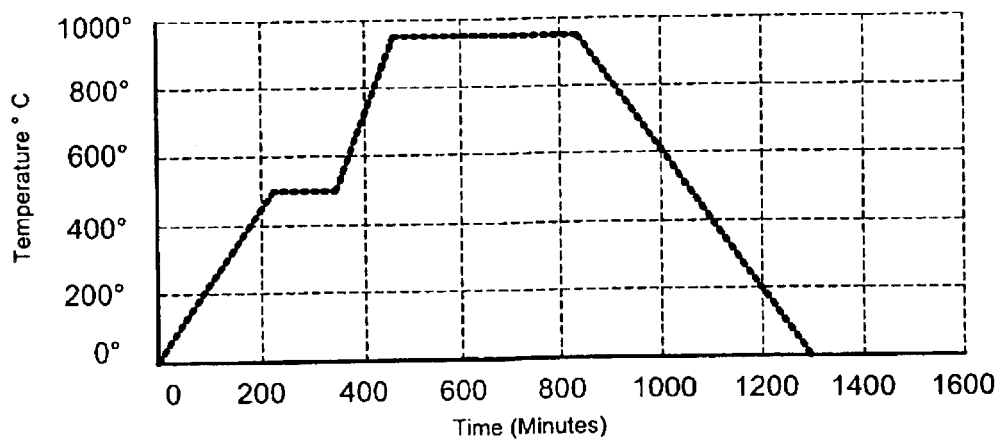
FIG. 7A depicts a furnace cycle for removal of a binder material from diamond feedstock prior to sintering.

If a volatile binder is used, it should be removed from the shaped diamond prior to sintering. The shaped diamond is placed into a furnace and the binding agent is either gasified or pyrolized for a sufficient length of time such that there is no binder remaining. Polycrystalline diamond compact quality is reduced by foreign contamination of the diamond or substrate, and great care must be taken to ensure that contaminants and binder are removed during the furnace cycle. Ramp up and the time and temperature combination are critical for effective pyrolization of the binder. For the binder example given above, the debinding process preferably used to remove the binder is as follows. Reviewing FIG. 7A while reading this description may be helpful.

First, the shaped diamond and binder are heated to from ambient temperature to about 500 degrees Celsius. The temperature is preferably increased by about 2 degrees Celsius per minute until about 500 degrees Celsius is reached. Second, the temperature of the bound and shaped diamond is maintained at about 500 degrees Celsius for about 2 hours. Third, the temperature of the diamond is increased again. The temperature is preferably increased from about 500 degrees Celsius by about 4 degrees per minute until a temperature of about 950 degrees Celsius is reached. Fourth, the diamond is maintained at about 950 degrees Celsius for about 6 hours. Fifth, the diamond is then permitted to return to ambient temperature at a temperature decrease of about 2 degrees per minute.

In some embodiments of the invention, it may be desirable to preform bound diamond feedstock by an appropriate process, such as injection molding. The diamond feedstock may include diamond crystals of one or more sizes, solvent-catalyst metal, and other ingredients to control diamond recrystallization and solvent-catalyst metal distribution. Handling the diamond feedstock is not difficult when the desired final curvature of the part is flat, convex dome or conical. However, when the desired final curvature of the part has complex contours, such as illustrated herein, providing uniform thickness and accuracy of contours of the polycrystalline diamond compact is more difficult when using powder diamond feedstock. In such cases it may be desirable to perform the diamond feedstock before sintering.

If it is desired to perform diamond feedstock prior to loading into a can for sintering, rather than placing powder diamond feedstock into the can, the steps described herein and variations of them may be followed. First, as already described, a suitable binder is added to the diamond feedstock. Optionally, powdered solvent-catalyst metal and other components may be added to the feedstock as well. The binder will typically be a polymer chosen for certain characteristics, such as melting point, solubility in various solvents, and CTE. One or more polymers may be included in the binder. The binder may also include an elastomer and/or solvents as desired in order to achieve desired binding, fluid flow and injection molding characteristics. The working volume of the binder to be added to a feedstock preferably will be equal to or slightly more than the measured volume of empty space in a quantity of lightly compressed powder. Since binders typically consist of materials such as organic polymers with relatively high CTE's, the working volume should be calculated for the injection molding temperatures expected. The binder and feedstock should be mixed thoroughly to assure uniformity of composition. When heated, the binder and feedstock will have sufficient fluid character to flow in high pressure injection molding. The heated feedstock and binder mixture is then injected under pressure into molds of desired shape. The molded part then cools in the mold until set, and the mold can then be opened and the part removed. Depending on the final polycrystalline diamond compact geometry desired, one or more molded diamond feedstock component can be created and placed into a can for polycrystalline diamond compact sintering. Further, use of this method permits diamond feedstock to be molded into a desired form and then stored for long periods of time prior to use in the sintering process, thereby simplifying manufacturing and resulting in more efficient production.

As desired, the binder may be removed from the injection molded diamond feedstock form. A variety of methods are available to achieve this. For example, by simple vacuum or hydrogen furnace treatment, the binder may be removed from the diamond feedstock form. In such a method, the form would be brought up to a desired temperature in a vacuum or in a very low pressure hydrogen (reducing) environment. The binder will then volatilize with increasing temperature and will be removed from the form. The form may then be removed from the furnace. When hydrogen is used, it helps to maintain extremely clean and chemically active surfaces on the diamond crystals of the diamond feedstock form.

An alternative method for removing the binder from the form involves utilizing two or polymer (such as polyethylene) binders with different molecular weights. After initial injection molding, the diamond feedstock form is placed in a solvent bath which removes the lower molecular weight polymer, leaving the higher molecular weight polymer to maintain the shape of the diamond feedstock form. Then the diamond feedstock form is placed in a furnace for vacuum or very low pressure hydrogen treatment for removal of the higher molecular weight polymer.

Partial or complete binder removal from the diamond feedstock form may be performed prior to assembly of the form in a pressure assembly for polycrystalline diamond compact sintering. Alternatively, the pressure assembly including the diamond feedstock form may be placed into a furnace for vacuum or very low pressure hydrogen furnace treatment and binder removal.

Diamond feedstock may be selected and loaded in order to create different types of gradients in the diamond table. These include an interface gradient diamond table, an incremental gradient diamond table, and a continuous gradient diamond table.

If a single type or mix of diamond feedstock is loaded adjacent a substrate, as discussed elsewhere herein, sweep of solvent-catalyst metal through the diamond will create an interface gradient in the gradient transition zone of the diamond table.

An incremental gradient diamond table may be created by loading diamond feedstocks of differing characteristics (diamond particle size, diamond particle distribution, metal content, etc.) in different strata or layers before sintering. For example, a substrate is selected, and a first diamond feedstock containing 60% solvent-catalyst metal by weight is loaded in a first strata adjacent the substrate. Then a second diamond feedstock containing 40% solvent-catalyst metal by weight is loaded in a second strata adjacent the first strata. Optionally, additional strata of diamond feedstock may be used. For example, a third strata of diamond feedstock containing 20% solvent-catalyst metal by weight may be loaded adjacent the second strata.

A continuous gradient diamond table may be created by loading diamond feedstock in a manner that one or more of its characteristics continuously vary from one depth in the diamond table to another. For example, diamond particle size may vary from large near a substrate (in order to create large interstitial spaces in the diamond for solvent-catalyst metal to sweep into) to small near the diamond bearing surface in order to create a part that is strongly bonded to the substrate but that has a very low friction bearing surface.

The diamond feedstocks of the different strata may be of the same or different diamond particle size and distribution. Solvent-catalyst metal may be included in the diamond feedstock of the different strata in weight percentages of from about 0% to more than about 80%. In some embodiments, diamond feedstock will be loaded with no solvent-catalyst metal in it, relying on sweep of solvent-catalyst metal from the substrate to achieve sintering. Use of a plurality of diamond feedstock strata, the strata having different diamond particle size and distribution, different solvent-catalyst metal by weight, or both, allows a diamond table to be made that has different physical characteristics at the interface with the substrate than at the load bearing and articulation surface. This allows a polycrystalline diamond compact to be manufactured which has a diamond table very firmly bonded to its substrate, and which has very favorable characteristics at the load bearing and articulation surface in order to achieve low friction articulation, impact resistance, and durability.

f. Reduction of Free Volume in Diamond Feedstock

As mentioned earlier, it may be desirable to remove free volume in the diamond feedstock before sintering is attempted. The inventors have found this is a useful procedure when producing spherical concave and convex parts. If a press with sufficient anvil travel is used for high pressure and high temperature sintering, however, this step may not be necessary. Preferably free volume in the diamond feedstock will be reduced so that the resulting diamond feedstock is at least about 95% theoretical density and preferably closer to about 97% of theoretical density.

Referring to FIGS. 8 and 8A, an assembly used for precompressing diamond to eliminate free volume is depicted. In the drawing, the diamond feedstock is intended to be used to make a convex spherical polycrystalline diamond part. The assembly may be adapted for precompressing diamond feedstock for making polycyrstalline diamond compacts of other complex shapes.

The assembly depicted includes a cube 801 of a pressure transfer medium. A cube is made from pyrophillite or other appropriate pressure transfer material such as a synthetic pressure medium and is intended to undergo pressure from a cubic press with anvils simultaneously pressing the six faces of the cube. A cylindrical cell rather than a cube would be used if a belt press were utilized for this step.

The cube 801 has a cylindrical cavity 802 or passage through it. The center of the cavity 802 will receive a spherical refractory metal can 810 loaded with diamond feedstock 806 that is to be precompressed. The diamond feedstock 806 may have a substrate with it.

The can 810 consists of two hemispherical can halves 810a and 810b, one of which overlaps the other to form a slight lip 812. The can is preferably an appropriate refractory metal such as niobium, tantalum, molybdenum, etc. The can is typically two hemispheres, one which is slightly larger to accept the other being slid inside of it to fully enclosed the diamond feedstock. A rebated area or lip is provided in the larger can so that the smaller can will satisfactorily fit therein. The seam of the can is sealed with an appropriate sealant such as dry hexagonal boronitride or a synthetic compression medium. The sealant forms a barrier that prevents the salt pressure medium from penetrating the can. The can seam may also be welded by plasma, laser, or electron beam processes.

An appropriately shaped pair of salt domes 804 and 807 surround the can 810 containing the diamond feedstock 806. In the example shown, the salt domes each have a hemispherical cavity 805 and 808 for receiving the can 810 containing the spherical diamond feedstock 806. The salt domes and the can and diamond feedstock are assembled together so that the salt domes encase the diamond feedstock. A pair of cylindrical salt disks 803 and 809 are assembled on the exterior of the salt domes 804 and 807. All of the aforementioned components fit within the bore 802 of the pressure medium cube 801.

The entire pyrocube assembly is placed into a press and pressurized under appropriate pressure (such as about 40–68 Kbar) and for an appropriate although brief duration to precompress the diamond and prepare it for sintering. No heat is necessary for this step.

g. Prepare Heater Assembly

In order to sinter the assembled and loaded diamond feedstock described above into polycrystalline diamond, both heat and pressure are required. Heat is provided electrically as the part undergoes pressure in a press. A prior art heater assembly is used to provide the required heat.

A refractory metal can containing loaded and precompressed diamond feedstock is placed into a heater assembly. Salt domes are used to encase the can. The salt domes used are preferably white salt (NaCl) that is precompressed to at least about 90–95% of theoretical density. This density of the salt is desired to preserve high pressures of the sintering system and to maintain geometrical stability of the manufactured part. The salt domes and can are placed into a graphite heater tube assembly. The salt and graphite components of the heater assembly are preferably baked in a vacuum oven at greater than 100 degrees Celsius and at a vacuum of at least 23 torr for about 1 hour in order to eliminate adsorbed water prior to loading in the heater assembly. Other materials which may be used in construction of a heater assembly include solid or foil graphite, amorphous carbon, pyrolitic carbon, refractory metals and high electrical resistant metals.

Once electrical power is supplied to the heater tube, it will generate heat required for polycrystalline diamond formation in the high pressure/high temperature pressing operation.

h. Preparation of Pressure Assembly for Sintering

Once a heater assembly has been prepared, it is placed into a pressure assembly for sintering in a press under high pressure and high temperature. A cubic press or a belt press may be used for this purpose, with the pressure assembly differing somewhat depending on the type of press used. The pressure assembly is intended to receive pressure from a press and transfer it to the diamond feedstock so that sintering of the diamond may occur under isostatic conditions.

If a cubic press is used, then a cube of suitable pressure transfer media such as pyrophillite will contain the heater assembly. Cell pressure medium would be used if sintering were to take place in a belt press. Salt may be used as a pressure transfer media between the cube and the heater assembly. Thermocouples may be used on the cube to monitor temperature during sintering. The cube with the heater assembly inside of it is considered a pressure assembly, and is place into a press a press for sintering.

i. Sintering of Feedstock into Polycrystalline Diamond

Figure 8B:
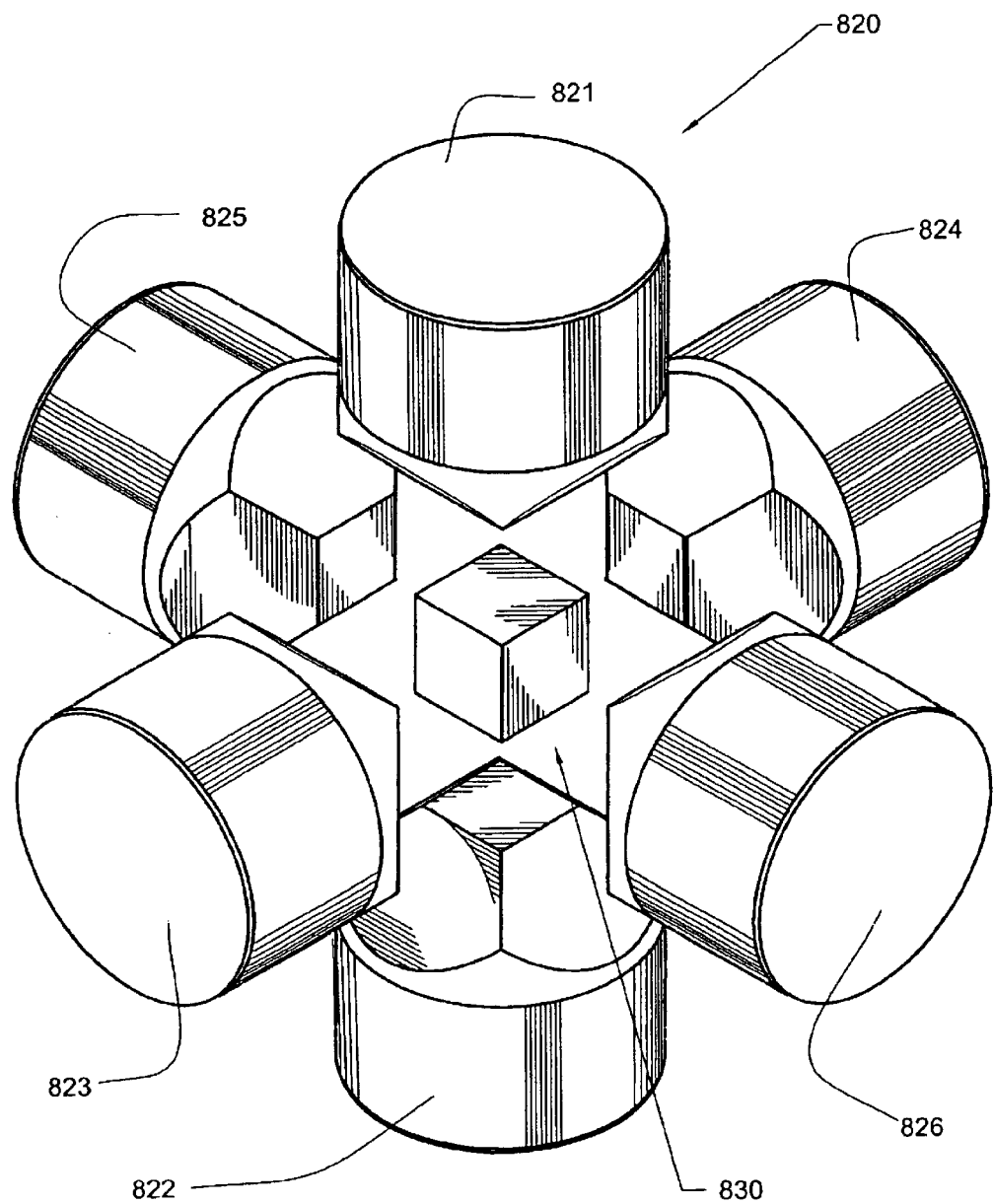
FIG. 8B depicts the anvil arrangement of a high pressure/high temperature press cubic press and a pressure cube on which it would exert pressure in order to sinter diamond.

The pressure assembly described above containing a refractory metal can that has diamond feedstock loaded and precompressed within is placed into an appropriate press. The type of press preferably used at the time of the invention is a cubic press (i.e., the press has six anvil faces) for transmitting high pressure to the assembly along 3 axes from six different directions. Alternatively, a belt press and a cylindrical cell can be used to obtain similar results. Referring to FIG. 8B, a representation of the 6 anvils of a cubic press 820 is provided. The anvils 821, 822, 823, 824, 825 and 826 are situated around a pressure assembly 830.

To prepare for sintering, the entire pressure assembly is loaded into a cubic press and initially pressurized to about 40–68 Kbars. The pressure to be used depends on the product to be manufactured and must be determined empirically. Then electrical power is added to the pressure assembly in order to reach a temperature preferably in the range of less than about 1145 or 1200 to more than about 1500 degrees Celsius. Preferably about 5800 watts of electrical power is available at two opposing anvil faces, creating the current flow required for the heater assembly to generate the desired level of heat. Once the desired temperature is reached, the pressure assembly is subjected to pressure of about 1 million pounds per square inch at the anvil face. The components of the pressure assembly transmit pressure to the diamond feedstock. These conditions are maintained for preferably about 3–12 minutes, but could be from less than 1 minute to more than 30 minutes. The sintering of polycrystalline diamond compacts takes place in an isostatic environment where the pressure transfer components are permitted only to change in volume but are not permitted to otherwise deform. Once the sintering cycle is complete, about a 90 second cool down period is allowed, and then pressure is removed. The polycrystalline diamond compact is then removed for finishing.

Removal of a sintered polycrystalline diamond compact having a curved, compound or complex shape from a pressure assembly is simple due to the differences in material properties between diamond and the surrounding metals in preferred embodiments of the invention. This is generally referred to as the mold release system of the invention.

One or more of the following component processes is incorporated into the mold release system:

1) An intermediate layer of material between the polycrystalline diamond compact part and the mould that prevents bonding of the polycrystalline diamond compact to the mould surface.
2) A mold material that does not bond to the polycrystalline diamond compact under the conditions of synthesis.
3) A mold material that, in the final stages of, or at the conclusion of, the polycrystalline diamond compact synthesis cycle either contracts away from the polycrystalline diamond compact in the case of a net concave polycrystalline diamond compact geometry, or expands away from the polycrystalline diamond compact in the case of a net convex polycrystalline diamond compact geometry.
4) The mold shape can also act, simultaneously as a source of sweep metal useful in the polycrystalline diamond compact synthesis process.

As an example, below is a discussion of use of a mold release system in manufacturing a polycrystalline diamond compact by employing a negative shape of the desired geometry to produce hemispherical cups. The mold surface contracts away from the final net concave geometry, the mold surface acts as a source of solvent-catalyst metal for the polycrystalline diamond compact synthesis process, and the mold surface has poor bonding properties to polycrystalline diamond compacts.

In the case of forming concave hemispherical cups such as are used for articulating surfaces in ball and socket joints, two different methods have been employed. In the first method, one, a mold consisting of a cobalt chrome (ASTM F-799) ball is used as a substrate around which a layer of polycrystalline diamond compact feedstock material is placed, contained by an outer can. A separator ring composed of a material such as mica or compressed hexagonal boron nitride (HBN) is positioned at the hemisphere of the mold ball to allow separation of the two concave hemispherical polycrystalline diamond compact parts at the conclusion of the synthesis process. During the polycrystalline diamond compact synthesis process, the cobalt-chrome ball expands in size due to the increase in temperature intrinsic to the process. It also can supply solvent-catalyst sweep metal to the polycrystalline diamond compact synthesis process.

After the polycrystalline diamond compact shell has formed around the mold ball, the ball separates from the two hemispherical polycrystalline diamond compact cups as it contracts on cooling and pressure reduction. The forces of the shrinking CoCr ball will exceed the bond strength of diamond to the CoCr, providing a fairly clean separation and a smooth polycrystalline diamond cup adjacent a detached spherical CoCr ball.

As an alternative, it is possible to use an intermediate layer of material between the polycrystalline diamond compact part and the mold surface. The intermediate material should be a material which contracts away from the final net concave polycrystalline diamond compact geometry to achieve mold separation with the polycrystalline diamond compact.

The second mold release method for use in forming a hemispherical cup is similar to the first method. However, in the second method, the mold is a cobalt-cemented tungsten carbide ball or sphere that has been coated with a thin layer of hexagonal boron nitride. During the polycrystalline diamond compact synthesis process, the tungsten carbide ball expands in size due to the increase in temperature intrinsic to the process. After the polycrystalline diamond compact shell has formed around the mold ball, the mold ball separates from the two hemispherical polycrystalline diamond compact cups as it contracts on cooling. The hexagonal boron nitride prevents bonding between the polycrystalline diamond compact layer and the tungsten carbide ball and a clean separation is achieved.

j. Removal of Solvent-Catalyst Metal from PCD

If desired, the solvent-catalyst metal remaining in interstitial spaces of the sintered polycrystalline diamond may be removed. Such removal is accomplished by chemical leaching as is known in the art. After solvent-catalyst metal has been removed from the interstitial spaces in the diamond table, the diamond table will have greater stability at high temperatures. This is because there is no catalyst for the diamond to react with and break down. Removal of solvent-catalyst metal from interstitial spaces in the diamond may also be desirable if the solvent-catalyst material is not biocompatible.

After leaching solvent-catalyst metal from the diamond table, it may be replaced by another metal, metal or metal compound in order to form thermally stable diamond that is stronger than leached polycrystalline diamond. If it is intended to weld synthetic diamond or a polycrystalline diamond compact to a substrate or to another surface such as by inertia welding, it may be desirable to use thermally stable diamond due to its resistance to heat generated by the welding process.

3. Finishing Methods and Apparatuses

Once a polycrystalline diamond compact has been sintered, a mechanical finishing process is preferably employed to prepare the final product. The preferred finishing steps explained below are described with respect to finishing a polycrystalline diamond compact, but they could be used to finish any other bearing surface or any other type of component.

Prior to the invention herein, the synthetic diamond industry was faced with the problem of finishing flat surfaces and thin edges of diamond compacts. Methods for removal of large amounts of diamond from spherical surfaces or finishing those surfaces to high degrees of accuracy for sphericity, size and surface finish had not been developed in the prior art.

a. Finishing of Superhard Cylindrical and Flat Forms.

In order to provide a greater perspective on the most preferred finishing techniques for curved and spherical superhard surfaces, a description of other finishing techniques is provided.

1.) Lapping.

A wet slurry of diamond grit on cast iron or copper rotating plates are used to remove material on larger flat surfaces (e.g., up to about 70 mm. in diameter). End coated cylinders of size ranging from about 3 mm to about 70 mm may also be lapped to create flat surfaces. Lapping is generally slow and not dimensionally controllable for depth and layer thickness, although flatness and surface finishes can be held to very close tolerances.

2.) Grinding.

Diamond impregnated grinding wheels are used to shape cylindrical and flat surfaces. Grinding wheels are usually resin bonded in a variety of different shapes depending on the type of material removal required (i.e., cylindrical centerless grinding or edge grinding). Polycrystalline diamond compacts are difficult to grind, and large polycrystalline diamond compact surfaces are nearly impossible to grind. Consequently, it is desirable to keep grinding to a minimum, and grinding is usually confined to a narrow edge or perimeter or to the sharpening of a sized PDC end-coated cylinder or machine tool insert.

3.) Electro Spark Discharge Grinding (EDG).

Rough machining of polycrystalline diamond compact may be accomplished with electro spark discharge grinding ("EDG") on large diameter (e.g., up to about 70 mm.) flat surfaces. This technology typically involves the use of a rotating carbon wheel with a positive electrical current running against a polycrystalline diamond compact flat surface with a negative electrical potential. The automatic controls of the EDG machine maintain proper electrical erosion of the polycrystalline diamond compact material by controlling variables such as spark frequency, voltage and others. EDG is typically a more efficient method for removing larger volumes of diamond than lapping or grinding. After EDG, the surface must be finish lapped or ground to remove what is referred to as the heat affected area or re-cast layer left by EDG.

4.) Wire Electrical Discharge Machining (WEDM).

WEDM is used to cut superlard parts of various shapes and sizes from larger cylinders or flat pieces. Typically, cutting tips and inserts for machine tools and re-shaping cutters for oil well drilling bits represent the greatest use for WEDM in PDC finishing.

5.) Polishing.

Polishing superhard surfaces to very high tolerances may be accomplished by diamond impregnated high speed polishing machines. The combination of high speed and high friction temperatures tends to burnish a PDC surface finished by this method, while maintaining high degrees of flatness, thereby producing a mirror-like appearance with precise dimensional accuracy.

b. Finishing A Spherical Geometry.

Finishing a spherical surface (concave spherical or convex spherical) presents a greater problem than finishing a flat surface or the rounded edge of a cylinder. The total surface area of a sphere to be finished compared to the total surface area of a round end of a cylinder of like radius is four (4) times greater, resulting in the need to remove four (4) times the amount of polycrystalline diamond compact material. The nature of a spherical surface makes traditional processing techniques such as lapping, grinding and others unusable because they are adapted to flat and cylindrical surfaces. The contact point on a sphere should be point contact that is tangential to the edge of the sphere, resulting in a smaller amount of material removed per unit of time, and a proportional increase in finishing time required. Also, the design and types of processing equipment and tooling required for finishing spherical objects must be more accurate and must function to closer tolerances than those for other shapes. Spherical finishing equipment also requires greater degrees of adjustment for positioning the workpiece and tool ingress and egress.

The following are steps that may be performed in order to finish a spherical, rounded or arcuate surface.

1.) Rough Machining.

It is preferred to initially rough out the dimensions of the surface using a specialized electrical discharge machining apparatus. Referring to FIG. 9, roughing a polycrystalline diamond compact sphere 903 is depicted. A rotator 902 is provided that is continuously rotatable about its longitudinal axis (the z axis depicted). The sphere 903 to be roughed is attached to a spindle of the rotator 902. An electrode 901 is provided with a contact end 901A that is shaped to accommodate the part to be roughed. In this case the contact end 901A has a partially spherical shape. The electrode 901 is rotated continuously about its longitudinal axis (the y axis depicted). Angular orientation of the longitudinal axis y of the electrode 901 with respect to the longitudinal axis z of the rotator 902 at a desired angle β is adjusted to cause the electrode 901 to remove material from the entire spherical surface of the ball 903 as desired.

Thus, the electrode 901 and the sphere 903 are rotating about different axes. Adjustment of the axes can be used to achieve near perfect spherical movement of the part to be roughed. Consequently, a nearly perfect spherical part results from this process. This method produces polycrystalline diamond compact spherical surfaces with a high degree of sphericity and cut to very close tolerances. By controlling the amount of current introduced to the erosion process, the depth and amount of the heat affected zone can be minimized. In the case of a polycrystalline diamond compact, the heat affected zone can be kept to about 3 to 5 microns in depth and is easily removed by grinding and polishing with diamond impregnated grinding and polishing wheels.

Referring to FIG. 10, roughing a convex spherical polycrystalline diamond compact 1003 such as an acetablular cup is depicted. A rotator 1002 is provided that is continuously rotatable about its longitudinal axis (the z axis depicted). The part 1003 to be roughed is attached to a spindle of the rotator 1002. An electrode 1001 is provided with a contact end 1001A that is shaped to accommodate the part to be roughed. The electrode 1001 is continuously rotatable about its longitudinal axis (the y axis depicted). Angular orientation of the longitudinal axis y of the electrode 1001 with respect to the longitudinal axis z of the rotator 1002 at a desired angle β is adjusted to cause the electrode 1001 to remove material from the entire spherical surface of the cup 1003 as desired.

In some embodiments of the invention, multiple electro discharge machine electrodes will be used in succession in order to machine a part. A battery of electro discharge machines may be employed to carry this out in assembly line fashion.

2.) Finish Grinding and Polishing.

Once the spherical surface (whether concave or convex) has been rough machined as described above or by other methods, finish grinding and polishing of a part can take place. Grinding is intended to remove the heat affected zone in the polycrystalline diamond compact material left behind by electrodes. Use of the same rotational geometry as depicted in FIGS. 9 and 10 allows sphericity of the part to be maintained while improving its surface finish characteristics.

Referring to FIG. 11, it can be seen that a rotator 1101 holds a part to be finished 1103, in this case a convex sphere, by use of a spindle. The rotator 1101 is rotated continuously about its longitudinal axis (the z axis). A grinding or polishing wheel 1102 is rotated continuously about its longitudinal axis (the x axis). The moving part 1103 is contacted with the moving grinding or polishing wheel 1102. The angular orientation β of the rotator 1101 with respect to the grinding or polishing wheel 1102 may be adjusted and oscillated to effect grinding or polishing of the part (ball or socket) across its entire surface and to maintain sphericity.

Referring to FIG. 12, it can be seen that a rotator 1201 holds a part to be finished 1203, in this case a convex spherical cup, by use of a spindle. The rotator 1201 is rotated continuously about its longitudinal axis (the z axis). A grinding or polishing wheel 1202 is provided that is continuously rotatable about its longitudinal axis (the x axis). The moving part 1203 is contacted with the moving grinding or polishing wheel 1202. The angular orientation β of the rotator 1201 with respect to the grinding or polishing wheel 1202 may be adjusted and oscillated if required to effect grinding or polishing of the part across the spherical portion of it surface.

In the preferred embodiment of the invention, grinding utilizes a grit size ranging from 100 to 150 according to standard ANSI B74.16-1971 and polishing utilizes a grit size ranging from 240 to 1500, although grit size may be selected according to the user's preference. Wheel speed for grinding should be adjusted by the user to achieve a favorable material removal rate, depending on grit size and the material being ground. A small amount of experimentation can be used to determine appropriate wheel speed for grinding.

As desired in the invention, a diamond abrasive hollow grill may be used for polishing diamond or superhard bearing surfaces. A diamond abrasive hollow grill includes a hollow tube with a diamond matrix of metal, ceramic and resin (polymer) is found.

If a diamond surface is being polished, then the wheel speed for polishing preferably will be adjusted to cause a temperature increase or heat buildup on the diamond surface. This heat buildup will cause burnishing of the diamond crystals to create a very smooth and mirror-like low friction surface. Actual material removal during polishing of diamond is not as important as removal sub-micron sized asperities in the surface by a high temperature burnishing action of diamond particles rubbing against each other. A surface speed of 6000 feet per minute minimum is generally required together with a high degree of pressure to carry out burnishing. Surface speeds of 4000 to 10,000 feet per minute are believed to be the most desirable range. Depending on pressure applied to the diamond being polished, polishing may be carried out at from about 500 linear feet per minute and 20,000 linear feet per minute.

Pressure must be applied to the workpiece in order to raise the temperature of the part being polished and thus to achieve the most desired mirror-like polish, but temperature should not be increased to the point that it causes complete degradation of the resin bond that holds the diamond polishing wheel matrix together, or resin will be deposited on the diamond. Excessive heat will also unnecessarily degrade the surface of the diamond.

Maintaining a constant flow of coolant (such as water) across the diamond surface being polished, maintaining an appropriate wheel speed such as 6000 linear feet per minute, applying sufficient pressure against the diamond to cause heat buildup but not so much as to degrade the wheel or damage the diamond, and timing the polishing appropriately are all important and must all be determined and adjusted according to the particular equipment being used and the particular part being polished. Generally the surface temperature of the diamond being polished should not be permitted to rise above 800 degrees Celsius or excessive degradation of the diamond will occur. Desirable surface finishing of the diamond, called burnishing, generally occurs between 650 and 750 degrees Celsius.

During polishing it is important to achieve a surface finish that has the lowest possible coefficient of friction, thereby providing a low friction and long-lasting articulation surface. Preferably, once a diamond or other superhard surface is formed in a prosthetic joint, the surface is then polished to an Ra value of 0.3 to 0.005 microns. Acceptable polishing will include an Ra value in the range of 0.5 to 0.005 microns or less. The parts of the joint may be polished individually before assembly or as a unit after assembly. Other methods of polishing polycrystalline diamond compacts and other superhard materials could be adapted to work with the articulation surfaces of the invented joints, with the objective being to achieve a smooth surface, preferably with an Ra value of 0.01–0.005 microns.

In order to select two matching prosthetic joint halves for shipment and implantation in a patient, it is preferred that precise measurement of the opposing bearing surfaces be taken at 98.6 degrees Fahrenheit (normal body temperature) in order to match joint halves with appropriate dimensions.

Structures manufactured according to the principles of the invention set forth above will provide strong and durable low friction bearing surfaces for a variety of uses including prosthetic joints.

While the present invention has been described and illustrated in conjunction with a number of specific embodiments, those skilled in the art will appreciate that variations and modifications may be made without departing from the principles of the invention as illustrated herein and as claimed. The present invention may be embodied in other specific forms without departing from its spirit or essential characteristics. The described embodiments are to be considered in all respects as only illustrative, and not restrictive. The scope of the invention is, therefore, indicated by the appended claims, rather than by the foregoing description. All changes that come within the meaning and range of equivalency of the claims are to be embraced within their scope.

We claim:

1. A femoral head comprising:

a sintered polycrystalline diamond compact, a substrate located on said polycrystalline diamond compact, solvent-catalyst metal located in said substrate, a diamond table sintered to said substrate, a gradient transition zone between said substrate and said diamond table in said polycrystalline diamond compact, said gradient transition zone having a substrate side and a diamond table side, said gradient transition zone having both solvent-catalyst metal and diamond therein, and said gradient transition zone exhibiting a transition of ratios of percentage content of solvent-catalyst metal to diamond from one side of said gradient transition zone to another such that at a first point in said gradient transition zone near said substrate side, the ratio of percentage content of solvent-catalyst metal to diamond is greater than it is at a second point in said gradient transition zone closer to said diamond side than said first point, chemical bonds between said diamond table and said substrate which tend to secure said diamond table to said substrate, and a sintered polycrystalline diamond load bearing and articulation surface on said polycrystalline diamond compact, said sintered polycrystalline diamond load bearing and articulation surface including polycrystalline diamond, said sintered polycrystalline diamond load bearing and articulation surface being formed to present a shape that is at least partially convex spherical;

wherein diamond in said sintered polycrystalline diamond compact has a coefficient of thermal expansion $CTE_{Cd}$, and wherein said substrate has a coefficient of thermal expansion $CTE_{sub}$, and wherein $CTE_{Cd}$ is not equal to $CTE_{sub}$, wherein said diamond in said polycrystalline diamond compact has a modulus $M_{Cd}$, and wherein said substrate in said polycrystalline diamond compact has a modulus $M_{sub}$, and wherein $M_{Cd}$ is not equal to $M_{sub}$.

2. A head as recited in claim 1 further comprising a mechanical grip between said diamond table and said substrate, said mechanical grip tending to secure said diamond table to said substrate.

3. A head as recited in claim 1 further comprising interstitial spaces in said diamond table.

4. A head as recited in claim 3 further comprising solvent-catalyst metal located in said diamond table interstitial spaces.

5. A head as recited in claim 1 further comprising a residual stress field in said polycrystalline diamond compact that tends to enhance the strength of said polycrystalline diamond compact.

6. A head as recited in claim 1 further comprising a crystalline diamond structure in said diamond table.

7. A head as recited in claim 1 wherein said polycrystalline diamond compact is polished to an Ra value of between about 0.5 to about 0.005 microns.

8. A head as recited in claim 1 wherein said substrate includes a plurality of metals.

9. A head as recited in claim 1 wherein said substrate includes a metal alloy selected from the group consisting of titanium, titanium aluminum and vanadium, titanium molybdenum hafnium, titanium and nitinol, cobalt chrome, cobalt chrome molybdenum, cobalt chrome tungsten, cobalt chrome cemented tungsten carbide, cobalt chrome cemented chrome carbide, fused silicon carbide and stainless steel.

10. A head as recited in claim 1 further comprising a first substrate layer and a second substrate layer.

11. A head as recited in claim 10 wherein said first substrate layer includes at least one metal not found in said second substrate layer.

12. A head as recited in claim 10 further comprising a barrier layer between said first and second substrate layers.

13. A head as recited in claim 1 wherein in said polycrystalline diamond compact diamond table, at least two different sizes of diamond crystals are found.

14. A head as recited in claim 1 further comprising substrate surface topographical features on said substrate.

15. A head as recited in claim 1 wherein said sintered polycrystalline diamond load bearing and articulation surface has an Ra value of between about 0.5 to about 0.005 microns.

16. A head as recited in claim 1 wherein said sintered polycrystalline diamond load bearing and articulation surface is burnished.

17. A femoral head comprising:
a metal substrate,
a diamond table,
said substrate and said diamond table forming a sintered polycrystalline diamond compact,
a zone between said substrate and said diamond table that has a composition gradient of decreasing solvent-catalyst metal content across said zone,
chemical bonds in said zone, said chemical bonds including diamond-to-diamond bonds in said diamond table, diamond-to-metal bonds in said gradient transition zone, and metal-to-metal bonds in said solvent-catalyst metal,
at least some of said bonds being sp3 carbon bonds,
a mechanical grip between said diamond table and said substrate which tends to secure said diamond table to said substrate,
said mechanical grip being achieved at least in part by residual stresses between said substrate and said diamond table,
interstitial spaces in said diamond table,
solvent-catalyst metal present in said interstitial spaces, and
a non-planar sintered polycrystalline diamond load bearing and articulation surface formed by said diamond table,
said non-planar sintered polycrystalline diamond load bearing and articulation surface serving to permit articulation of the femoral head in a human body.

18. A femoral head as recited in claim 17 wherein sintered diamond in said diamond table has a coefficient of thermal expansion $CTE_{Cd}$, and wherein said substrate has a coefficient of thermal expansion $CTE_{sub}$, and wherein $CTE_{Cd}$ is not equal to $CTE_{sub}$.

19. A femoral head as recited in claim 17 wherein said sintered diamond in said diamond table has a modulus $M_{Cd}$, and wherein said substrate has a modulus $M_{sub}$, and wherein $M_{Cd}$ is not equal to $M_{sub}$.

20. A femoral head as recited in claim 17 further comprising a residual stress field that tends to enhance the strength of attachment of said diamond table to said substrate.

21. A femoral head as recited in claim 17 further comprising substrate surface topographical features on said substrate.

22. A femoral head as recited in claim 17 wherein said substrate includes a metal alloy with at least one femoral head of said metal alloy being selected from the group consisting of titanium, aluminum, vanadium, molybdenum, hafnium, nitinol, cobalt, chrome, molybdenum, tungsten, cemented tungsten carbide, cemented chrome carbide, fused silicon carbide, nickel, tantalum, and stainless steel.

23. A femoral head as recited in claim 17 wherein diamond table comprises diamond feedstock that has diamond particles that have a dimension in the range of less than about 1 nanometer to more than about 100 microns.

24. A femoral head as recited in claim 17 wherein said sintered polycrystalline diamond load bearing and articulation surfaces is a continuous diamond surface.

25. A femoral head as recited in claim 17 wherein said sintered polycrystalline diamond load bearing and articulation surface is a discontinuous diamond surface.

26. A femoral head as recited in claim 17 wherein said sintered polycrystalline diamond load bearing and articulation surface is a segmented diamond surface.

27. A femoral head as recited in claim 17 wherein a lip is present on said substrate in order to mechanically interlock said diamond table to said substrate.

28. A femoral head as recited in claim 17 further comprising CoCr solvent-catalyst metal in said diamond table interstitial spaces.

29. A femoral head as recited in claim 17 further comprising a continuous gradient in said diamond table.

30. A femoral head as recited in claim 17 further comprising an incremental gradient in said diamond table.

31. A femoral head as recited in claim 30 wherein said incremental gradient includes a plurality of strata in said diamond table, a first of said strata having characteristics which differ from those of a second strata.

32. A femoral head as recited in claim 31 wherein said differing characteristics of said strata are selected from the group consisting of diamond particle size, diamond particle distribution, and solvent-catalyst metal content.

33. A femoral head as recited in claim 17 further comprising an interface gradient.

34. A femoral head as recited in claim 17 wherein said diamond table has a thickness of from less than about 1 micron to more than about 3000 microns.

35. A femoral head comprising:
   a substrate,
   a diamond table sintered to said substrate,
   said substrate and diamond table forming a sintered polycrystalline diamond compact,
   a zone that includes both sintered diamond and substrate, said zone having a composition gradient of solvent-catalyst metal content to diamond content, said gradient being selected from the group consisting of interface gradient, continuous gradient and incremental gradient,
   chemical bonds in the femoral head, said chemical bonds including diamond-to-diamond bonds in said diamond table, diamond-to-metal bonds in said zone, and metal-to-metal bonds in said solvent-catalyst metal,
   a mechanical grip between said diamond table and said substrate which tends to secure said diamond table to said substrate, and
   a non-planar load bearing and articulation surface formed by said diamond table.

36. A femoral head as recited in claim 35 wherein at least some of said bonds are sp3 carbon bonds.

37. A femoral head as recited in claim 35 wherein said diamond table includes a plurality of strata such that a first of said strata having characteristics which differ from those of a second strata.

38. A femoral head as recited in claim 37 wherein said differing characteristics are selected from the group consisting of diamond particle size, diamond particle distribution, and solvent-catalyst metal content.

39. A femoral head as recited in claim 35 wherein said diamond table has been formed using CoCr as a solvent-catalyst metal.

40. A femoral head as recited in claim 35 wherein said diamond table presents a non-planar sintered polycrystalline diamond load bearing and articulation surface.

41. A femoral head as recited in claim 35 further comprising interstitial spaces located in said diamond table, and solvent-catalyst metal located in said interstitial spaces.

42. A femoral head as recited in claim 35 further comprising interstitial spaces in said diamond table; wherein said interstitial spaces are at least partially filled with a metal.

43. A femoral head as recited in claim 42 wherein said interstitial spaces are filled with solvent-catalyst metal.

* * * * *